US012595273B2

(12) United States Patent
Vankayalapati et al.

(10) Patent No.: US 12,595,273 B2
(45) Date of Patent: Apr. 7, 2026

(54) PHOSPHONATE CONJUGATES AND USES THEREOF

(71) Applicants: The Translational Genomics Research Institute, Phoenix, AZ (US); University of Utah Research Foundation, Salt Lake City, UT (US)

(72) Inventors: Hariprasad Vankayalapati, Draper, UT (US); Sunil Sharma, Phoenix, AZ (US); Alana L. Welm, Park City, UT (US)

( * ) Notice: Subject to any disclaimer, the term of this patent is extended or adjusted under 35 U.S.C. 154(b) by 878 days.

(21) Appl. No.: 17/422,689

(22) PCT Filed: Jan. 15, 2020

(86) PCT No.: PCT/US2020/013618
§ 371 (c)(1),
(2) Date: Jul. 13, 2021

(87) PCT Pub. No.: WO2020/150307
PCT Pub. Date: Jul. 23, 2020

(65) Prior Publication Data

US 2022/0119425 A1 Apr. 21, 2022

Related U.S. Application Data

(60) Provisional application No. 62/792,725, filed on Jan. 15, 2019.

(51) Int. Cl.
*C07F 9/09* (2006.01)
*C07D 213/73* (2006.01)
*C07F 9/38* (2006.01)

(52) U.S. Cl.
CPC .............. *C07F 9/09* (2013.01); *C07D 213/73* (2013.01); *C07F 9/38* (2013.01)

(58) Field of Classification Search
None
See application file for complete search history.

(56) References Cited

U.S. PATENT DOCUMENTS

| | | | |
|---|---|---|---|
| 6,214,812 B1 | 4/2001 | Karpeisky et al. | |
| 2005/0153990 A1 | 7/2005 | Watkins | |

FOREIGN PATENT DOCUMENTS

| | | |
|---|---|---|
| WO | 2008/058229 A1 | 5/2008 |
| WO | 2013/078295 A2 | 5/2013 |

OTHER PUBLICATIONS

Schroeder et al. Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily. J. Med. Chem. 2009, 52, 5, 1251-1254 (Year: 2009).*

Farrell et al. Bisphosphonate conjugation for bone specific drug targeting. Bone Reports, 2018, 9, 47-60 (Year: 2018).*

Schroeder et al. J. Med. Chem. 2009, 52, 5, 1251-1254 (Year: 2009).*

Farrell et al. Bone Reports, 2018, 9, 47-60 (Year: 2018).*

Uludag, et al. Bisphosphonate Conjugation to Proteins as a Means to Impart Bone Affinity. Biotechnol Prog 2000; 16(2):258-267.

Schroeder, G. M., et al. Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem 2009; 52(5):1251-1254.

Braun, S., et al. Lack of effect of adjuvant chemotherapy on the elimination of single dormant tumor cells in bone marrow of high-risk breast cancer patients. Journal of Clinical Oncology 2000; 18(1):80-86.

Braun, S., et al. A pooled analysis of bone marrow micrometastasis in breast cancer. N Engl J Med 2005; 353 (8):793-802.

Naumov, G. N., et al. Ineffectiveness of doxorubicin treatment on solitary dormant mammary carcinoma cells or late- developing metastases. Breast Cancer Research and Treatment 2003; 82(3):199-206.

Janni, W., et al. Persistence of a disseminated tumor cells in the bone marrow of breast cancer patients predicts increased risk for relapse—a European pooled analysis. Clinical Cancer Research 2011: 17(9):2967-2976.

Diel, I. J., et al. Treatment of metastatic bone disease in breast cancer: bisphosphates. Clin Breast Cancer 2000; 1(1):43-51.

Coleman, R. E. Clinical features of metastatic bone disease and risk of skeletal morbidity. Clinical Cancer Research 2006; 12(20 Pt 2):6243s-6249s.

Coleman, R. E., et al. Possible survival benefits from zoledronic acid treatment in patients with bone metastases from solid tumours and poor prognostic features—an exploratory analysis of placebo-controlled trials. J Bone Oncol 2013; 2(2):70-76.

Kommalapati, A., et al. Evaluation and management of skeletal disease in cancer care. Crit Rev Oncol Hematol 2017; 120:217-226.

Guise, T. A. The vicious cycle of bone metastases. J Musculoskelet Neuronal Interact 2002; 2(6):570-572.

Mundy, G. R. Metastasis to bone: causes, consequences and therapeutics opportunities. Nature Reviews Cancer 2002; 2(8):584-593.

Engblom, C., et al. Osteoblasts remotely supply lung tumors with cancer-promoting SiglecF<sup>high</sup> neutrophils. Science 2017; 358(6367).

Early Breast Cancer Trialists' Collaborative Group. Adjuvant bisphosphonate treatment in early breast cancer: meta-analyses of individual patient data from randomized trials. Lancet 2015; 386(10001):1353-1361.

(Continued)

*Primary Examiner* — Clinton A Brooks
*Assistant Examiner* — Nicola Maria Bauer
(74) *Attorney, Agent, or Firm* — Wood, Phillips, Katz, Clark & Mortimer

(57) ABSTRACT

Phosphonate conjugates, preferably, bisphosphonate conjugates: methods of inhibiting Ron receptor tyrosine kinase and methods of treatment of bone destruction due to cancer or other conditions utilizing the provided phosphonate conjugates.

12 Claims, 3 Drawing Sheets

(56) References Cited

OTHER PUBLICATIONS

Clemons, M., et al. Bone-targeted agents and skeletal-related events in breast cancer patients with bone metastases: the state of the art. Curr Oncol 2012; 19(5):259-268.
Gul, G., et al. A comprehensive review of denosumab for bone metastasis in patients with solid tumors. Curr Med Res Opin 2016; 32(1):133-145.
Eyob, H., et al. Inhibition of ron kinase blocks conversion of micrometastases to overt metastases by boosting antitumor immunity. Cancer Discovery 2013; 3(7):751-760.
Welm, A. L., et al. The macrophage stimulating protein pathway promotes metastasis in a mouse model for breast cancer and predicts poor prognosis in humans. Proceedings of the National Academy of Sciences of the United States of America 2007; 104(18):7570-7575.
Andrade, K., et al. RON kinase: A target for treatment of cancer-induced bone destruction and osteoporosis. Science Translational Medicine 2017; 9(374):eaai9338.
Eyob, H., et al. RON promotes the metastatic spread of breast carcinomas by subverting antitumor immune responses. Oncoimmunology 2013; 2(9):e25670.
Nanney, L. B., et al. Proteolytic cleavage and activation of pro-macrophage-stimulating protein and upregulation of its receptor in tissue injury. The Journal of Investigative Dermatology 1998; 111(4):573-581.
Brunelleschi, S., et al. Macrophage stimulating protein (MSP) evokes superoxide anion production by human macrophages of different origin. British Journal of Pharmacology 2001; 134(6):1285-1295.
Iwama, A., et al. Terminal differentiation of murine resident peritoneal macrophages is characterized by expression of the STK protein tyrosine kinase, a receptor for macrophage-stimulating protein. Blood 1995; 86(9):3394-3403.
Nikolaidis, N. M., et al. Ron receptor tyrosine kinase negatively regulates TNFalpha production in alveolar macrophages by inhibiting NR-kappaB activity and Adam17 production. Shock 2010; 33(2):197-204.
Nikolaidis, N. M., et al. Ron receptor deficient alveolar myeloid cells exacerbate LPS-induced acute lung injury in the murine lung. Innate Immunity 2011; 17(6):499-507.
Yu, S., et al. The Ron Receptor Tyrosine Kinase Regulates Macrophage Heterogeneity and Plays a Protective Role in Diet-Induced Obesity, Atherosclerosis, and Hepatosteatosis. Journal of Immunology 2016; 197(1):256-265.
Gurusamy, D., et al. Myeloid-specific expression of Ron receptor kinase promotes prostate tumor growth. Cancer Research 2013; 73(6):1752-1763.
Sharda, D. R., et al. Regulation of macrophage arginase expression and tumor growth by the Ron receptor tyronise kinase. Journal of Immunology 2011; 187(5):2181-2192.
Davies, L. C., et al. A quantifiable proliferative burst of tissue macrophages restores homeostatic macrophage populations after acute inflammation. European Journal of Immunology 2011; 41(8):2155-2164.
Lahmar, Q., et al. Tissue resident versus monocyte-derived macrophages in the tumor microenvironment. Biochimica et biophysica acta (BBA)—Reviews on Cancer 2016; 1865(1):23-34.
Kimura, Y., et al. The innate immune receptor Dectin-2 mediates the phagocytosis of cancer cells by Kupffer cells for the suppression of liver metastasis. Proceedings of the National Academy of Sciences of the United States of America 2016; 113(49):14097-14102.
Headley, M. B., et al. Visualization of immediate immune responses to pioneer metastatic cells in the lung. Nature 2016; 531(7595):513-517.
Sharma, S. K., et al. Pulmonary alveolar macrophages contribute to the premetastatic niche by suppressing antitumor T cell responses in the lungs. Journal of Immunology 2015; 194(11):5529-5538.
Kurihara, N., et al. Macrophage-stimulating protein (MSP) and its receptor, RON, stimulate human osteoclast activity but not proliferation: effect of MSP distinct from that of hepatocyte growth factor. Exp Hematol 1998; 26(11):1080-1085.
Lee, E. S., et al. RON receptor tyrosine kinase, a negative regulator of inflammation, inhibits HIV-1 transcription in monocytes/macrophages and is decreased in brain tissue from patients with AIDS. Journal of Immunology 2004; 173(11):6864-6872.
Gunella, G., et al. Macrophage-stimulating protein differently affects human alveolar macrophages from smoker and non-smoker patients: evaluation of respiratory burst, cytokine release and NF-kappaB pathway. British Journal of Pharmacology 2006; 148(4):478-489.
Chaudhuri, A., et al. Host genetic background impacts modulation of the TLR4 pathway by RON in tissue-associated macrophages. Immunology and Cell Biology 2013; 91(7):451-460.
Wang, X., et al. The ron receptor tyrosine kinase: a key regulator of inflammation and cancer progression. Critical Reviews in Immunology 2013; 33(6):549-574.
Li, H., et al. Cross talk between the bone and immune systems: osteoclasts function as antigen-presenting cells and activate CD4+ and CD8+ T cells. Blood 2010; 116(2):210-217.
Kiesel, J.R., et al. Cross-presentation by osteoclasts induces FoxP3 in CD8+ T cells. Journal of Immunology 2009; 182(9):5477-5487.
Ibanez, L., et al. Inflammatory Osteoclasts Prime TNFalpha-Producing CD4(+) T Cells and Express CX3 CR1. J Bone Miner Res 2016; 31(10):1899-1908.
Grassi, F., et al. T cell suppression by osteoclasts in vitro. Journal of Cellular Physiology 2011; 226(4):982-990.
Russell, R. G. Bisphosphonates: the first 40 years. Bone 2011; 49(1):2-19.
Coleman, R. E. Emerging strategies in bone health management for the adjuvant patient. Seminars in Oncology 2007; 34(6 Suppl 4):S11-S16.
Daubine, F., et al. Antitumor effects of clinical dosing regimens of bisphosphonates in experimental breast cancer bone metastasis. Journal of the National Cancer Institute 2007; 99(4):322-330.
Zheng, Y., et al. Inhibition of bone resorption, rather than direct cytotoxicity, mediates the anti-tumour actions of ibandronate and osteoprotegerin in a murine model of breast cancer bone metastasis. Bone 2007; 40(2):471-478.
Clezardin, P., et al. Bisphosphonates and cancer-induced bone disease: beyond their antiresorptive activity. Cancer Research 2005; 65(12):4971-4974.
Green, J.R. Bisphosphonates: preclinical review. The Oncologist 2004; 9 Suppl 4:3-13.
Senaratne, S. G., et al. Bisphosphonates induce apoptosis in human breast cancer cell lines. British Journal of Cancer 2000; 82(8):1459-1468.
Clezardin P., et al. In vitro and in vivo antitumor effects of bisphosphonates. Curr Med Chem 2003; 10(2):173-180.
Reinholz, G. G., et al. Distinct mechanisms of bisphosphonate action between osteoblasts and breast cancer cells: identity of a potent new bisphosphonate analogue. Breast Cancer Research and Treatment 2002; 71(3):257-268.
Clezardin, P. The antitumor potential of bisphosphonates. Seminars in Oncology 2002; 29(6 Suppl 21):33-42.
Green, J. R., et al. Preclinical pharmacology of CGP 42'446, a new, potent, heterocyclic bisphosphonate compound. J Bone Miner Res 1994; 9(5):745-751.
Manolagas, S. C., et al. The role of estrogen and androgen receptors in bone health and disease. Nat Rev Endocrinol 2013; 9(12):699-712.
Sabatino, R., et al. Macrophage depletion by free bisphosphonates and zoledronate-loaded red blood cells. PloS One 2014; 9(6):e101260.
Roelofs, A. J., et al. Bisphosphonates: molecular mechanisms of action and effects on bone cells, monocytes and macrophages. Current Pharmaceutical Design 2010; 16(27):2950-2960.
Junankar, S., et al. Real-time intravital imaging establishes tumor-associated macrophages as the extraskeletal target of bisphosphonate action in cancer. Cancer Discovery 2015; 5(1):35-42.
Goyette, P., et al. Gene-centric association mapping of chromosome 3p implicates MST1 in IBD pathogenesis. Mucosal Immunol 2008; 1(2):131-138.

(56) References Cited

OTHER PUBLICATIONS

Beckly, J. B., et al. Two-stage candidate gene study of chromosome 3p demonstrates an association between nonsynonymous variants in the MST1R gene and Crohn's disease. Inflamm Bowel Dis 2008; 14(4):500-507.
Kauder, S, E., et al. Functional consequences of the macrophage stimulating protein 689C inflammatory bowel disease risk allele. PloS One 2013; 8(12):e83958.
Kulkarni, R. M., et al. Ron receptor signaling is protective against DSS induced colitis in mice. American Journal of Physiology Gastrointestinal and Liver Physiology 2014; 306(12):G1065-G1074.
Kretschmann, K. L., et al. The macrophage stimulating protein/Ron pathway as a potential therapeutic target to impede multiple mechanisms involved in breast cancer progression. Current Drug Targets 2010; 11(9):1157-1168.
Liu, X., et al. Short-form Ron promotes spontaneous breast cancer metastasis through interactions with phosphoinositide 3-kinase. Genes & Cancer 2011; 2(7):753-762.
Cunha, S., et al. The RON receptor tyrosine kinase promotes metastasis by triggering MBD4-dependent DNA methylation reprogramming. Cell Reports 2014; 6(1):141-154.
Kretschmann, K. L., et al. Mouse models of breast cancer metastasis to bone. Cancer Metastasis Reviews 2012; 31(3-4):579-583.
Faham, N., et al. RON Signaling Is a Key Mediator of Tumor Progression in Many Human Cancers. Cold Spring Harb Symp Quant Biol 2016; 81:177.
Welm, A. L., et al. MET and MYC cooperate in mammary tumorigenesis. Proceedings of the National Academy of Sciences of the United States of America 2005; 102(12):4324-4329.
Welm, B. E., et al. Lentiviral transduction of stem cells for genetic analysis of mammary development and breast cancer. Cell Stem Cell 2008; 2(1):90-102.
DeRose, Y. S. W. G., et al. Tumor grafts derived from women with breast cancer authentically reflect tumor pathology, growth, metastasis and disease outcomes. Nature Medicine 2011; 17(11):1514-1520.
Sikora, M. J., et al. Invasive lobular carcinoma cell lines are characterized by unique estrogen-mediated gene expression patterns and altered tamoxifen response. Cancer Research 2014; 74(5):1463-1474.
Al-Ejeh, F., et al. Treatment of triple-negative breast cancer using anti-EGFR-directed radioimmunotherapy combined with radiosensitizing chemotherapy and PARP inhibitor. Journal of Nuclear Medicine 2013; 54(6):913-921.
DeRose, Y. S., et al. Patient derived models of human breast cancer: protocols for in vitro and in vivo applications in tumor biology and translational medicine. Current Protocols in Pharmacology 2013; Chapter 14:Unit 14.23.
Lum, D. H., et al. Overview of human primary tumorgraft models: comparisons with traditional oncology preclinical models and the clinical relevance and utility of primary tumorgrafts in basic and translational oncology research. Current Protocols in Pharmacology 2012; 59:14.22.1-14.22.9.
Kim, S. W. A., et al. A dominant mutant allele of the ING4 tumor suppressor found in human cancer cells exacerbates MYC-initiated mouse mammary tumorigenesis. Cancer Research 2010; 70(12):5155-5162.
Larrieu-Lahargue, F., et al. Netrin-4 induces lymphangiogenesis in vivo. Blood 2010; 115(26):5418-5426.
Waltz, S. E., et al. Ron-mediated cytoplasmic signaling is dispensable for viability but is required to limit inflammatory responses. The Journal of Clinical Investigation 2001; 108(4):567-576.
Clausen, B. E., et al. Conditional gene targeting in macrophages and granulocytes using LysMcre mice. Transgenic Research 1999; 8(4):265-277.
Chiu, W. S., et al. Transgenic mice that express Cre recombinase in osteoclasts. Genesis 2004; 39(3):178-185.
Guy, C.T., et al. Induction of mammary tumors by expression of polyomavirus middle T oncogene: a transgenic mouse model for metastatic disease. Molecular and Cellular Biology 1992; 12(3):954-961.
Guy, C. T., et al. Expression of the neuprotooncogene in the mammary epithelium of transgenic mice induces metastatic disease. Proceedings of the National Academy of Sciences of the United States of America 1992; 89(22):10578-10582.
Zhu, X., et al. Bone-targeted therapy for metastatic breast cancer—Where do we go from here? A commentary from the Bonus 8 meeting. J Bone Oncol 2014; 3(1):1-4.
Kurihara, N., et al. Macrophage-stimulating protein activates STK receptor tyrosine kinase on osteoclasts and facilitates bone resorption by osteoclast-like cells. Blood 1996; 87(9):3704-3710.
Yang, G., et al. Functional grouping of osteoclast genes revealed through microarray analysis. Biochemical and Biophysical Research Communications 2008; 366(2):352-359.
Knutson, K. L., et al. IL-2 immunotoxin therapy modulates tumor-associated regulatory T cells and leads to lasting immune-mediated rejection of breast cancers in neu-transgenic mice. Journal of Immunology 2006; 177(1):84-91.
Lukacher, A. E., et al. Resistance to polyoma virus-induced tumors correlates with CTL recognition of an immunodominant H-2Dk-restricted epitope in the middle T protein. Journal of Immunology 1998; 160(4):1724-1734.
Kemball, C. C., et al. Late priming and variability of epitope-specific CD8+ T cell responses during a persistent virus infection. Journal of Immunology 2005; 174(12):7950-7960.
Ercolini, A.M., et al. Identification and characterization of the immunodominant rat HER-2/neu MHC class I epitope presented by spontaneous mammary tumors from HER-2/neu-transgenic mice. Journal of Immunology 2003; 170(8):4273-4280.
De Vries, C. R., et al. The addition of recombinant vaccinia HER2/neu to oncolytic vaccinia-GMCSF given into the tumor microenvironment overcomes MDSC-mediated immune escape and systemic anergy. Cancer Gene Ther 2015; 22(3):154-162.
Hortobagyi, G. N. Unmet needs in metastatic bone disease and its complications: is progress possible? Seminars in Oncology 2001; 28(2 Suppl 6):1-3.
Reinholz, M. M., et al. A promising approach for treatment of tumor-induced bone diseases: utilizing bisphosphonate derivatives of nucleoside antimetabolites. Bone 2010; 47(1):12-22.
Zinnen, S., et al. Phase 1 study of the bone-targeting cytotoxic conjugate, etidronate-cytosine arabinoside (MBC-11), in cancer patients with bone metastases. Journal of Clinical Oncology 2017; 35(15_suppl):2589, Abstract only.
Yan, S.B., et al. LY2801653 is an orally bioavailable multi-kinase inhibitor with potent activity against MET, MST1R, and other oncoproteins, and displays anti-tumor activities in mouse xenograft models. Investigational New Drugs 2013; 31(4):833-844.
Kimmel, D. B. Mechanism of action, pharmacokinetic and pharmacodynamic profile, and clinical applications of nitrogen-containing bisphosphonates. J Dent Res 2007; 86(11):1022-1033.
Zhao, X., et al. Dosing of zoledronic acid with its anti-tumor effects in breast cancer. J Bone Oncol 2015; 4(3):98-101.
Kinders, R., et al. Phase 0 clinical trials in cancer drug development: from FDA guidance to clinical practice. Mol Interv 2007; 7(6):325-334.
Murgo, A. J., et al. Designing phase 0 cancer clinical trials. Clinical cancer Research 2008; 14(12):3675-3682.
Lipton, A., et al. Extended efficacy and safety of denosumab in breast cancer patients with bone metastases not receiving prior bisphosphonate therapy. Clinical cancer Research 2008; 14(20):6690-6696.
Rubinstein, L.V., et al. The statistics of phase 0 trials. Stat Med 2010; 29(10):1072-1076.
Coleman, R. E., et al. Metastasis and bone loss: Advancing treatment and prevention. Cancer Treat Rev 2010; 36(8):615-620.
Coleman, R. E. Future directions in the treatment and prevention of bone metastases. Am J Clin Oncol 2002; 25(6 Suppl 1):S32-S38.
Melton, L. J., et al. Fracture risk with multiple myeloma: A population-based study. J Bone Miner Res 2005; 20 (3):487-493.

(56) References Cited

OTHER PUBLICATIONS

Guise, T. A., et al. Cancer and bone 1998; Endocr Rev 1998; 19(1):18-54.
Weilbaecher, K. N., et al. Cancer to bone: A fatal attraction. Nat Rev Cancer 2011; 11(6):411-425.
Gralow, J. R., et al. NCCN Task Force Report: Bone health in cancer care. J Natl Compr Canc Netw 2009; 7 (Suppl. 3):S1-S32.
Lipton, A., et al. Superiority of denosumab to zoledronic acid for prevention of skeletal-related events: A combined analysis of 3 pivotal, randomised, phase 3 trials. Eur J Cancer 2012; 48(16):3082-3092.
Stopeck, A. T., et al. Denosumab compared with zoledronic acid for the treatment of bone metastases in patients with advanced breast cancer: A randomized, double-blind study. J Clin Oncol 2010; 28(35):5132-5139.
Kurata, T., et al. Efficacy and safety of denosumab for the treatment of bone metastases in patients with advanced cancer. Jpn J Clin Oncol 2012; 42(8):663-669.
Hageman, K., et al. The role of denosumab for prevention of skeletal-related complications in multiple myeloma. Ann Pharmacother 2013; 47(7-8):1069-1074.
Waning, D. L., et al. Excess TGF-b mediates muscle weakness associated with bone metastases in mice. Nat Med 2015; 21(11):1262-1271.
Wang, M. H., et al. The murine stk gene product, a transmembrane protein tyrosine kinase, is a receptor for macrophage-stimulating protein. Proc Natl Acad Sci U.S.A. 1995; 92(9):3933-3937.
Akiyama, M., et al. Impact of docosahexaenoic acid on gene expression during osteoclastogenesis in vitro—A comprehensive analysis. Nutrients 2013; 5(8):3151-3162.
Gaudino, G., et al. The proto-oncogene RON is involved in development of epithelial, bone and neuro-endocrine tissues. Oncogene 1995; 11(12):2627-2637.
Zinser, G. M., et al. Mammary-specific Ron receptor overexpression induces highly metastatic mammary tumors associated with b-catenin activation. Cancer Res 2006; 66(24):11967-11974.
Takayanagi, H. New developments in osteoimmunology. Nat Rev Rheumatol 2012; 8(11):684-689.
Correll, P. H., et al. Deregulated inflammatory response in mice lacking the STK/RON receptor tyrosine kinase. Genes Funct 1997; 1(1):69-83.
Steinig, A. G., et al. Novel 6-aminofuro[3,2-c]pyridines as potent, orally efficacious inhibitors of cMET and RON kinases. Bioorg Med Chem Lett 2013; 23(15):4381-4387.
Cummings, S. R., et al. Denosumab for prevention of fractures in postmenopausal women with osteoporosis. N Engl J Med 2009; 361:756-765.
Papapoulos, S., et al. Five years of denosumab exposure in women with postmenopausal osteoporosis: Results from the first two years of the FREEDOM extension. J Bone Miner Res 2012; 27(3):694-701.
Canon, J. R., et al. Inhibition of RANKL blocks skeletal tumor progression and improves survival in a mouse model of breast cancer bone metastasis. Clin Exp Metastasis 2008; 25(2):119-129.
Holland, P. M., et al. Combined therapy with the RANKL inhibitor RANK-Fc and rhApo2L/TRAIL/dulanermin reduces bone lesions and skeletal tumor burden in a model of breast cancer skeletal metastasis. Cancer Biol Ther 2010; 9(7):539-550.
Azim Jr., H. A., et al. RANK-ligand (RANKL) expression in young breast cancer patients and during pregnancy. Breast Cancer Res 2015; 17:24.
Huang, L., et al. Tumour cells produce receptor activator of NF-kB ligand (RANKL) in skeletal metastases. J Clin Pathol 2002; 55(11):877-878.
Sethi, N., et al. Tumor-derived JAGGED1 promotes osteolytic bone metastasis of breast cancer by engaging notch signaling in bone cells. Cancer Cell 2011; 19(2):192-205.
Forrester, E., et al. Effect of conditional knockout of the type II TGF-b receptor gene in mammary epithelia on mammary gland development and polyomavirus middle T antigen induced tumor formation and metastasis. Cancer Res 2005; 65(6):2296-2302.
Soriano, P., et al. Targeted disruption of the c-src proto-oncogene leads to osteopetrosis in mice. Cell 1991; 64(4):693-702.
Boyce, B. F., et al. Requirement of pp60c-src expression for osteoclasts to form ruffled borders and resorb bone in mice. J Clin Invest 1992; 90(4):1622-1627.
Izawa, T., et al. c-Src links a RANK/avb3 integrin complex to the osteoclast cytoskeleton. Mol Cell Biol 2012; 32(14):2943-2953.
Lin, P. H., et al. Transformation of mouse cells by wild-type mouse c-Src. Oncogene 1995; 10(2):401-405.
Mayo Clinic Medical Laboratories. Test ID: CTX, Beta-CrossLaps (Beta-CTx), Serum. Aug. 25, 2017. Access online:https://web.archive.org/web/20170825161233/http://www.mayomedicallaboratories.com/test-catalog/Clinical+and+Interpretive/83175.
Aslan Pharmaceuticals. Aslan Pharmaceuticals announces positive phase 1 results with ASLAN002. Mar. 16, 2015. Accessed online Aug. 17, 2021 at: http://aslanpharma.com/2015/03/16/aslan-announces-positive-phase-1-results-with-aslan002/.
Moiseeva, E. P., et al. EGFR and Src are involved in indole-3-carbinolinduced death and cell cycle arrest of human breast cancer cells. Carcinogenesis 2007; 28(2):435-445.
Mainou, B. A., et al. Src kinase mediates productive endocytic sorting of reovirus during cell entry. J Virol 2011; 85(7):3203-3213.
Moon, H. G., et al. Matrix protein CCN1 induced by bacterial DNA and CpG ODN limits lung inflammation and contributes to innate immune homeostasis. Mucosal Immunol 2015; 8(2):243-253.
Kabos, P., et al. Patient-derived luminal breast cancer xenografts retain hormone receptor heterogeneity and help define unique estrogen-dependent gene signatures. Breast Cancer Res Treat 2012: 135(2):415-432.
Kim, H. J., et al. Fyn promotes proliferation, differentiation, survival and function of osteoclast lineage cells. J Cell Biochem 2010; 111(5):1107-1113.
Horne, W. C., et al. Osteoclasts express high levels of pp60c-src in association with intracellular membranes. J Cell Biol 1992; 119(4):1003-1013.
Verollet, C., et al. Hck contributes to bone homeostasis by controlling the recruitment of osteoclast precursors. FASEB J 2013; 27(9):3608-3618.
Kim, H. J., et al. The Src family kinase, Lyn, suppresses osteoclastogenesis in vitro and in vivo. Proc Natl Acad Sci U.S.A. 2009; 106:2325-2330.
Yoon, S. H., et al. Lyn inhibits osteoclast differentiation by interfering with PLCg1-mediated Ca2+ signaling. FEBS Lett 2009; 583(7):1164-1170.
Parfitt, A. M., et al. Bone histomorphometry: Standardization of nomenclature, symbols, and units: Report of the ASBMR Histomorphometry Nomenclature Committee. J Bone Miner Res 1987; 2(6):595-610.
Suda, T., et al. Receptor tyrosine kinases involved in hematopoietic progenitor cells. Leukemia 1997; 11 (Suppl. 3):451-453.

* cited by examiner

10-dose $IC_{50s}$ for Compound 10, Compound 11 & BMS-777607

| | BMS-777607 | Compound 10 | Compound 12 |
|---|---|---|---|
| IC50 | 0.02895 | 0.5466 | 0.1287 |

10-dose $IC_{50s}$ for Compound 11, Compound 12 & BMS-777607

| | BMS-777607 | Compound 11 | Compound 12 |
|---|---|---|---|
| IC50 | 0.01507 | 1.274 | 0.06056 |

10-dose $IC_{50s}$ for Compound 12, Compound 13 & BMS-77760

| | BMS-777607 | Compound 12 | Compound 13 |
|---|---|---|---|
| IC50 | 0.01112 | 0.05812 | 2.427 |

PHOSPHONATE CONJUGATES AND USES THEREOF

STATEMENT REGARDING FEDERALLY SPONSORED RESEARCH OR DEVELOPMENT

This invention was made with government support under grant numbers W81XWH-18-1-0617 and W81XWH-18-1-0616 awarded by the United States Department of Defense, Congressionally Directed Medical Research Programs, Breast Cancer Research Program. The government has certain rights in the invention.

BACKGROUND

Cancer, and in particular, metastatic cancer remains one of the most challenging diseases to treat. Many cancers have the propensity to disseminate to distant organs, even before diagnosis of the primary tumor, where it can remain in a clinically undetectable state for many years. Eventual growth of these disseminated tumor cells (DTCs) into metastases, also known as distant recurrence, occurs in 20-30% of patients. Because metastatic cancer is often not curable, metastases are the overwhelming cause of breast cancer mortality.

DTCs are detectable in the bone marrow; where they can undergo dormancy and reawakening. Because of difficulties in tissue sampling, it is unknown how often DTCs exist in other tissues, and/or whether bone marrow DTCs migrate and give rise to metastases in other sites. However, it is clear that bone metastases are a common site of recurrence for many types of cancer. Because skeletal disease has profound systemic effects, it is thought that bone metastases can influence cancer progression in other sites. Bone metastases are often osteolytic due to activation of bone-resorbing resident macrophages known as osteoclasts. Osteoclasts are the key players in a "vicious cycle" whereby tumor-derived factors stimulate osteoclasts to release systemic tumor-promoting factors from the bone matrix and from the activated osteoclasts themselves. In this way, a feed-forward loop is created between tumor cells and osteoclasts, which leads to increased tumor growth and osteolysis. Importantly, several of these factors have recently been shown to have long-ranging systemic effects, promoting tumor growth and metastatic seeding not just locally, but across the body. Furthermore, published data are accumulating that show that osteoclasts can have a potent effect on immune responses in cancer.

Current treatment strategies for bone metastasis include inhibiting osteoclast function with bisphosphonates and targeting the RANKL/RANK signaling pathway in osteoclasts using denosumab. However, many patients have cancer progression and associated morbidities despite these treatments, and new strategies are needed.

In breast cancer patients, the inventors previously found that macrophage-stimulating protein (MSP) and its receptor, Ron (receptor originated from nantes) tyrosine kinase, are associated with an increased metastasis to bone and other sites, and a decreased overall survival. In mice, MSP over-expression in mammary tumors is sufficient to promote spontaneous metastasis from the mammary gland to the bone, lung, and other sites. Importantly, this depends on Ron signaling in the host, not in the tumor. MSP-driven bone metastases are osteolytic in nature, recapitulating the most common type of bone lesion in metastatic breast cancer patients. The inventors' work recently revealed that Ron functions in a novel pathway for osteoclast activation in breast cancer, through a mechanism that is independent of the well-characterized RANKL/RANK pathway and converges on Src activation. The inventors have previously shown that Ron inhibition can block osteolytic bone turnover in human cancer patients. Furthermore, MSP is over-expressed in several other types of advanced cancers that metastasize to bone and cause osteolytic disease, such as lung cancer and multiple myeloma.

Using mouse models, the inventors previously discovered that the Ron receptor tyrosine kinase is a key mediator of breast and lung cancer outgrowth at metastatic sites. Although Ron can play a role in the tumor cells themselves, the inventors found that the critical role for Ron is in the host microenvironment. Ron functions in various types of resident macrophages to indirectly support survival of tumor cells and to dampen the immune response, thereby facilitating metastatic outgrowth. The main host cells expressing Ron are osteoclasts, as well as a few other resident macrophages (e.g. peritoneal macrophages).

It is therefore important to develop novel Ron inhibitors that can be used to inhibit Ron tyrosine kinase and treat diseases where MSP and Ron tyrosine kinase plays a role, including cancer, and more specifically breast cancer, lung cancer, and multiple myeloma, and also including cancer metastases that arise in bone.

Furthermore, the inventors previously showed that Ron tyrosine kinase plays a role in bone loss due to osteoporosis, so Ron inhibitors can also be used to inhibit non-cancer diseases of bone such as osteoporosis. More than 40 million Americans develop osteoporosis, a condition of bone loss and skeletal weakness. Osteoporosis largely affects post-menopausal women because of low estrogen levels. Approximately 50% of women over the age of 50 experience an osteoporosis-related fracture. Mechanisms of bone loss in the condition of osteoporosis are very similar to the pathologies that occur in metastatic cancers that cause osteolysis: we discovered that Ron tyrosine kinase is involved in both cancer-related and osteoporosis-related bone destruction.

BRIEF SUMMARY OF THE INVENTION

The invention, in one aspect, relates to compounds useful as inhibitors of Ron tyrosine kinase. In a further aspect, the disclosed compounds, or a pharmaceutically acceptable salt, hydrate, solvate, or polymorph thereof, are modulators of Ron activity. The invention also provides methods of making these compounds, pharmaceutical compositions comprising these compounds, and methods of treating disorders associated with a Ron pathway using these compounds.

In one embodiment, the invention is directed to a conjugate of Compound A and a phosphonate, preferably a bisphosphonate (diphosphonic acid).

Compound A has the following structural formula:

Compound A

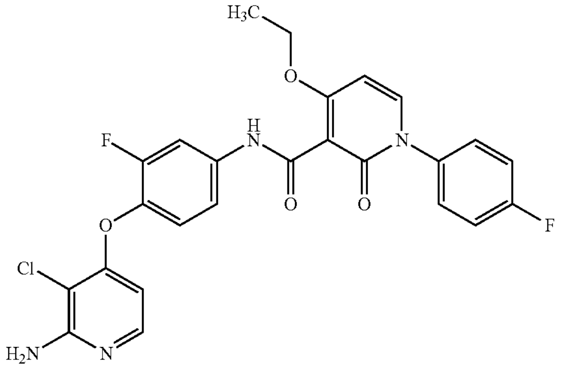

Compound A can be made by the methods described in this application below.

Thus, in one embodiment, the invention is directed to a conjugate of Compound A and a phosphonate (preferably, a bisphosphonate, bis(phosphonic acid), dihydrogen phosphate, methyl phosphonic acid), wherein a phosphonate is directly joined to Compound A at the 2-amino-3-chloropyridin (Site 1), 4-ethoxy (Site 2) and 4-fluorophenyl (Site 3) respectively on a published clinical agent (US 2007-936984, WO 2008058229, J. Med. Chem., 2009, 52 (5), pp 1251-1254); N-(4-((2-amino-3-chloropyridin-4-yl)oxy)-3-fluorophenyl)-4-ethoxy-1-(4-fluorophenyl)-2-oxo-1,2-dihydropyridine-3-carboxamide (BMS-777607) as shown below:

Compound A

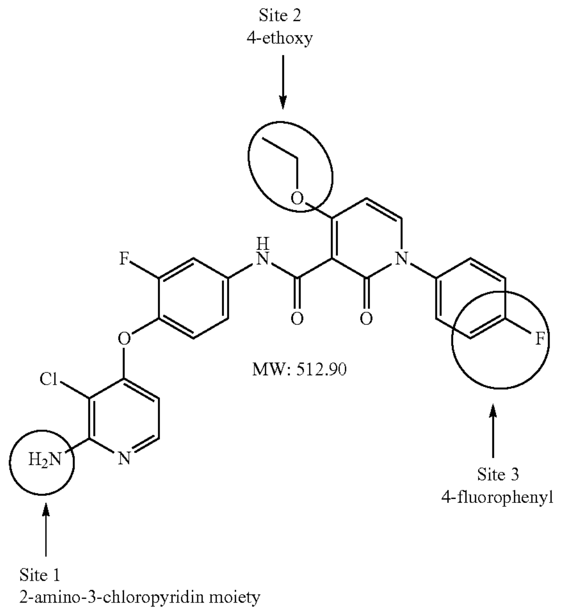

In one embodiment, the invention is directed to a compound of the following structural Formula 1:

Formula 1

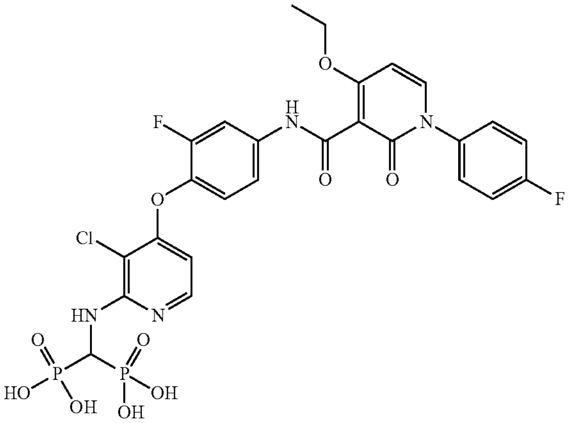

or a pharmaceutically acceptable salt, isomer, hydrate, solvate, or polymorph thereof.

The compound can also be referred to as (3-chloro-4-(4-(4-ethoxy-1-4-fluorophenyl)-2-oxo-1,2-dihydropyridine-3-carboxamido)-2-fluorophenoxy)pyridin-2-yl)amino)methylene)bis(phosphoric acid).

The invention also provides the following bisphosphonate, bis(phosphonic acid), dihydrogen phosphate, methyl phosphonic acid conjugates of Compound A or Formula 1:

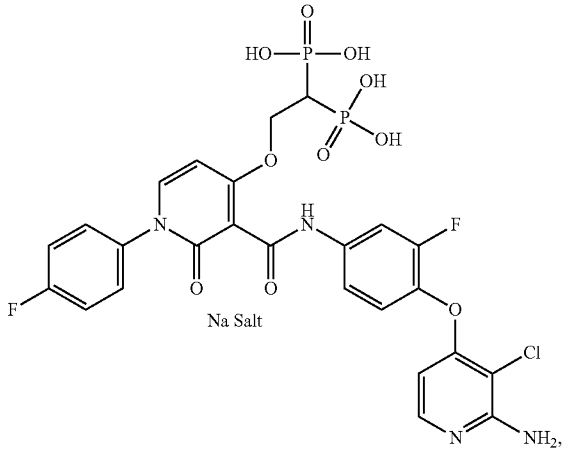

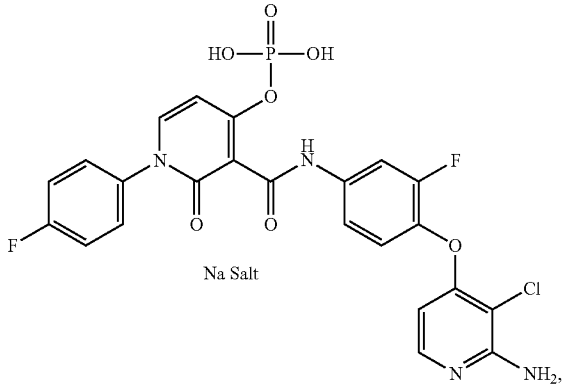

-continued
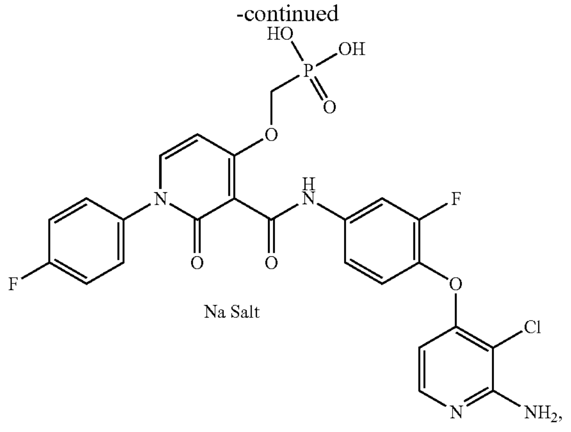
Na Salt
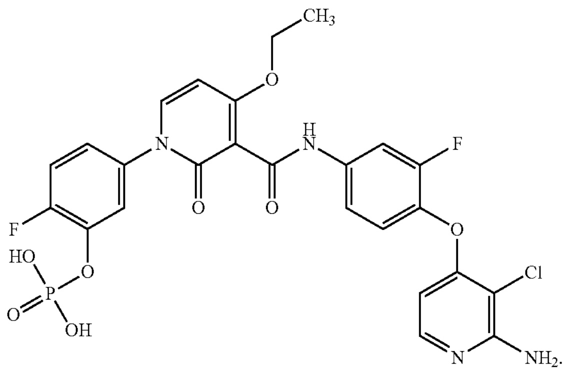
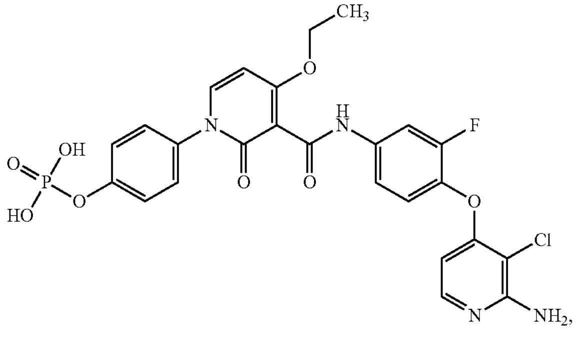
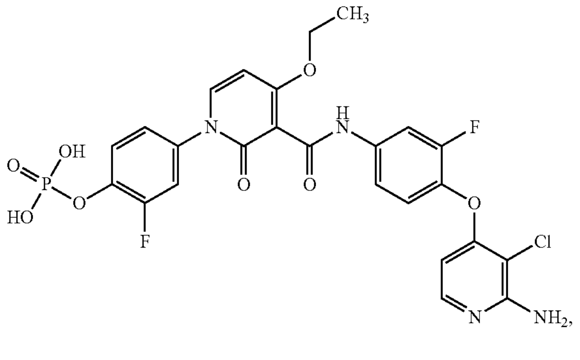
-continued
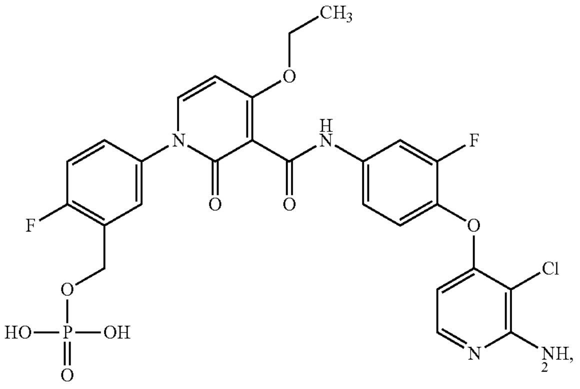
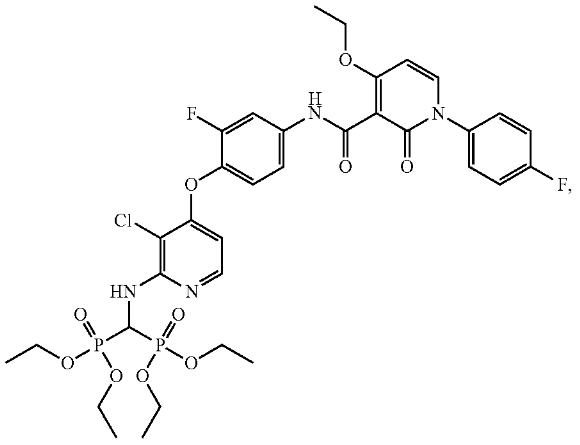
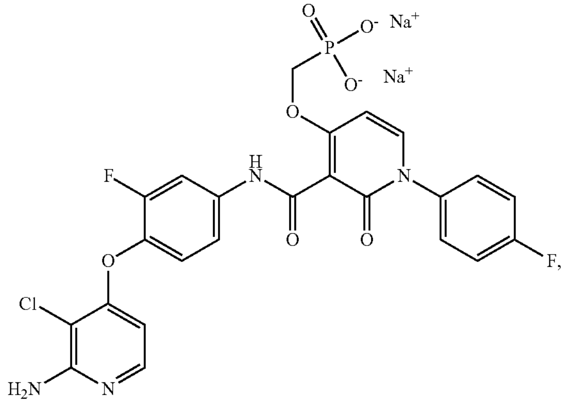
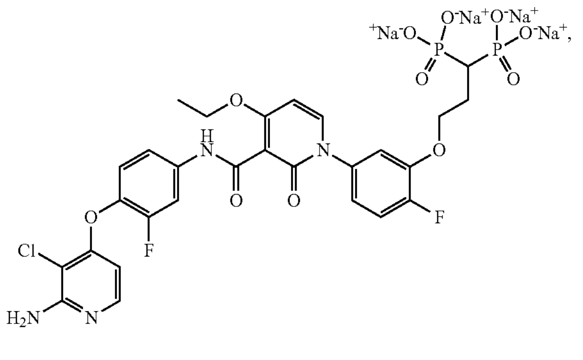

-continued

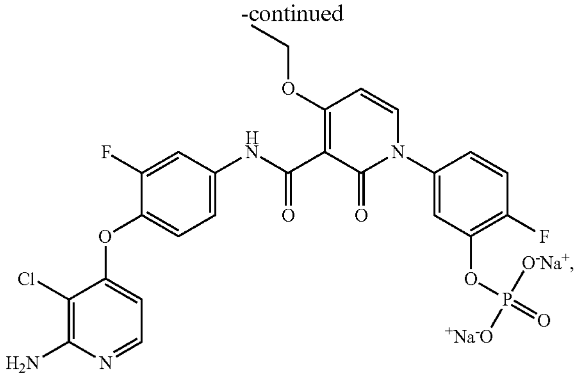

,

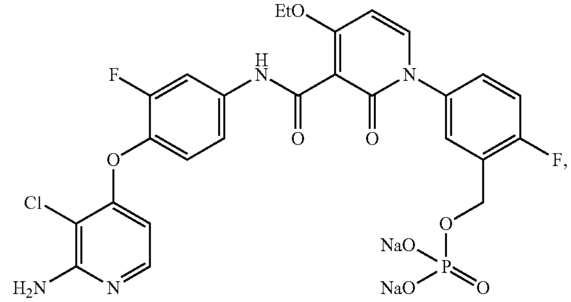

,

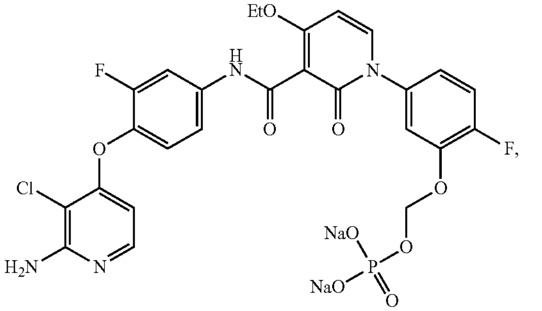

, and

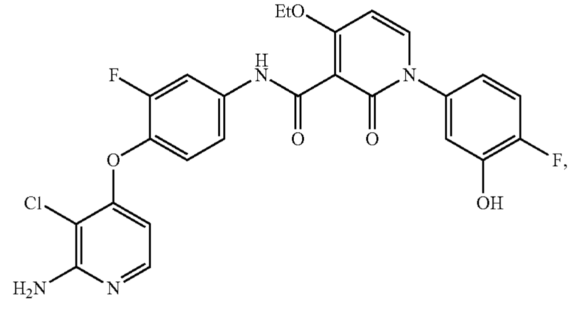

, as well as pharmaceutically acceptable salts, isomers, hydrates, solvates, and polymorphs thereof.

Also disclosed are pharmaceutical compositions comprising, a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with a Ron tyrosine kinase in a mammal comprising the step of administering to the mammal a therapeutically effective amount of a disclosed compound, or a pharmaceutically acceptable salt, isomer, hydrate, solvate, or polymorph thereof.

Also disclosed are methods for inhibition of Ron tyrosine kinase activity in a mammal comprising the step of administering to the mammal a therapeutically effective amount of least one disclosed compound, or a pharmaceutically acceptable salt, isomer hydrate, solvate, or polymorph thereof.

Also disclosed are methods for inhibiting Ron tyrosine kinase activity in at least one cell, comprising the step of contacting the at least one cell with an effective amount of least one disclosed compound, or a pharmaceutically acceptable salt, isomer, hydrate, solvate, or polymorph thereof.

In some embodiments, the invention provides methods of treatment of disorders of uncontrolled cellular proliferation, e.g. various cancers. In a still further aspect, the disorder of uncontrolled cellular proliferation is associated with a Ron tyrosine kinase.

In some embodiments, the invention provides methods of treatment of bone loss disorders, including but not limited to osteoporosis and osteoarthritis.

In yet another aspect, the compounds of the invention may be useful for the treatment of other bone disorders, including but not limited to, bone loss, osteoporosis and osteoarthritis.

Also disclosed are pharmaceutical compositions comprising a pharmaceutically acceptable carrier and an effective amount of a disclosed compound, or a pharmaceutically acceptable salt, isomer, hydrate, solvate, or polymorph thereof.

Also disclosed are methods for manufacturing a medicament comprising, combining at least one disclosed compound or at least one disclosed product with a pharmaceutically acceptable carrier or diluent. In a further aspect, the invention relates to the use of a disclosed compound in the manufacture of a medicament for the treatment of a disorder associated with a Ron tyrosine kinase activity. In a still further aspect, the invention relates to the uses of disclosed compounds in the manufacture of a medicament for the treatment of a a disorder of uncontrolled cellular proliferation.

Also disclosed are uses of a disclosed compound or a disclosed product in the manufacture of a medicament for the treatment of a disorder associated with a Ron tyrosine kinase activity in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect.

DESCRIPTION

A. Definitions

Figure 1:
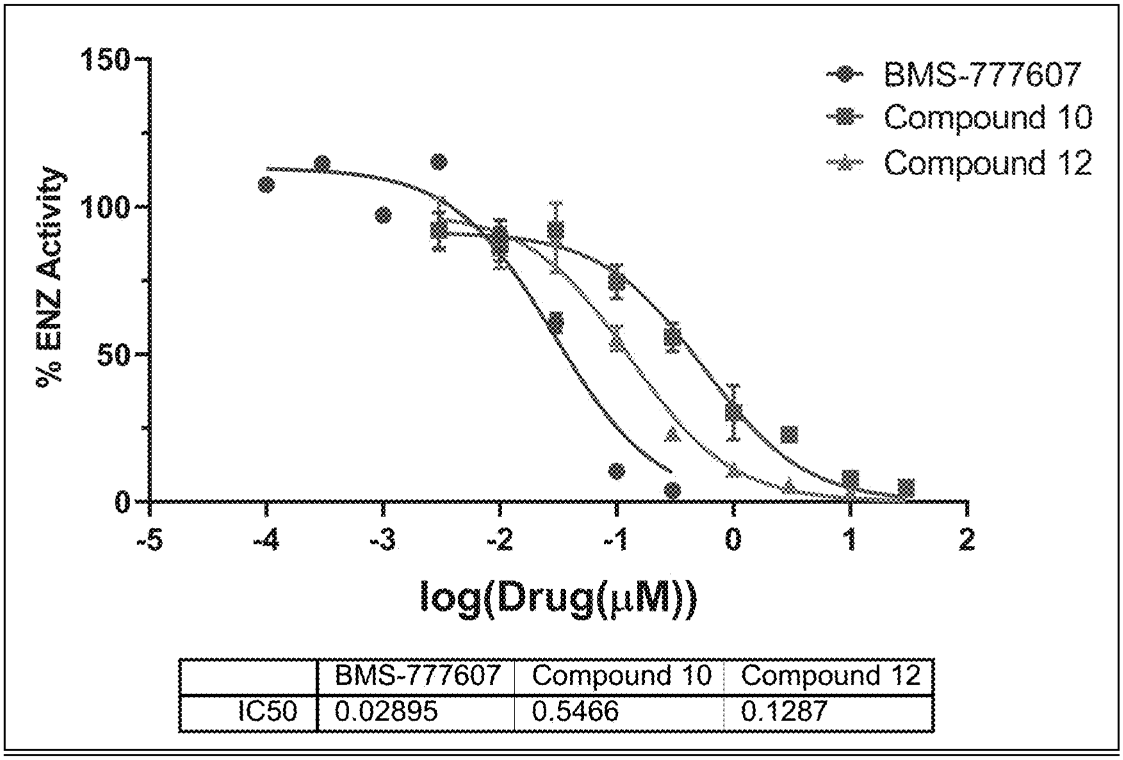
FIG. 1 is a RON kinase inhibition chart for BMS-777607 (a reference compound), Compound 10 and Compound 12.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "Ron" refers to Ron (receptor originated from nantes) tyrosine kinase.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a Ron tyrosine kinase activity prior to the administering step. In some aspects of the disclosed methods, the subject has been diagnosed with a need for inhibition of a Ron tyrosine kinase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder: preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it: (ii) inhibiting the disease, i.e., arresting its development: or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit Ron tyrosine kinase. As a further example, "diagnosed with a need for inhibition of a Ron tyrosine kinase" refers to having been subjected to a physical examination by a person of skill, for example, a physician, and found to have a condition characterized by a Ron tyrosine kinase activity. Such a diagnosis can be in reference to a disorder, such as a disorder of uncontrolled cellular proliferation, cancer and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a Ron tyrosine activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically: that is, administered to treat an existing disease or condition. In further various aspects, a preparation can be administered prophylactically: that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly: i.e., by interacting with the target itself, or indirectly: i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder: the specific composition employed: the age, body weight, general health, sex, and diet of the patient: the time of administration: the route of administration; the rate of excretion of the specific compound employed: the duration of the treatment: drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount": that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and/or (+) and (−) are employed to designate the sign of rotation of plane-polarized light by the compound, with (−) or/meaning that the compound is levorotatory. A compound prefixed with (+) or dis dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and(S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or(S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

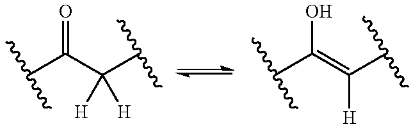

keto form enol form

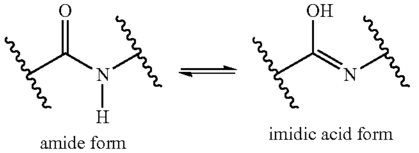

amide form imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

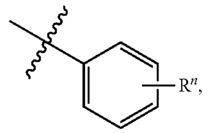

which is understood to be equivalent to a formula:

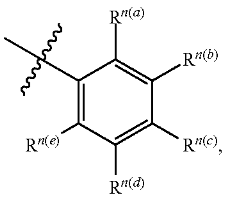

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions, including Compound A and bisphosphonates, are either available from commercial suppliers such as Sigma-Aldrich Chemical Co., (Milwaukee, WI.), Acros Organics (Morris Plains, NJ), Fisher Scientific (Pittsburgh, PA.), or Sigma (St. Louis, MO.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989): *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow: plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of Ron tyrosine kinase. Moreover, in one aspect, the compounds of the invention are useful in the treatment of disorders of uncontrolled cellular proliferation. In a still further aspect, the disorder of uncontrolled cellular proliferation is associated with a Ron tyrosine kinase.

In yet another aspect, the compounds of the invention may be useful for the treatment of other bone disorders, including but not limited to, bone loss, osteoporosis and osteoarthritis.

In a further aspect, the disorder of uncontrolled cellular proliferation is a cancer or a tumor.

In a further aspect, the cancer is breast cancer, lung cancer, or multiple myeloma. In yet another aspect, the cancer is metastatic cancer.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a conjugate of Compound A and bisphosphonate (diphosphonic acid).

Compound A has the following structural formula:

Compound A

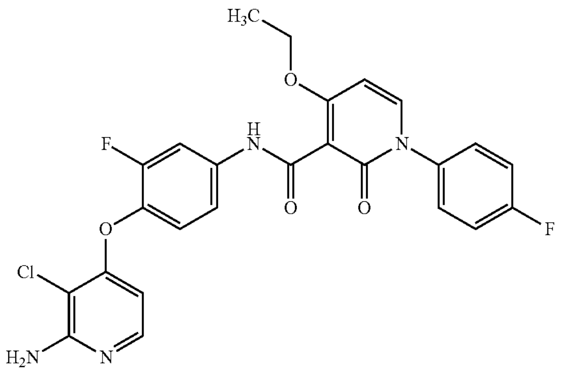

Thus, in one embodiment, the invention is directed to a conjugate of Compound A and a bisphosphonate, wherein a bisphosphonate is directly joined to Compound A at Site 1, Site 2 or Site 3 as shown below:

Compound A

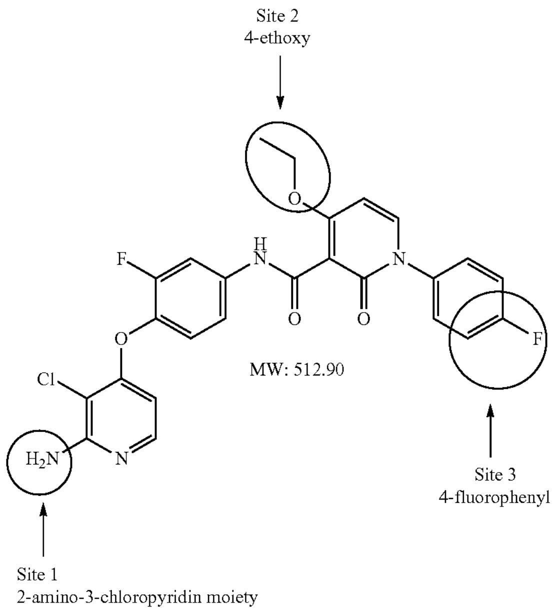

In one embodiment, the invention provides the following bisphosphonate, bis(phosphonic acid), dihydrogen phosphate, methyl phosphonic acid conjugates of Compound A:

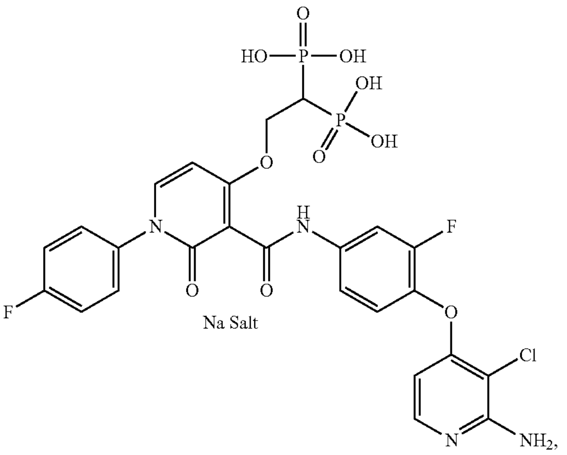

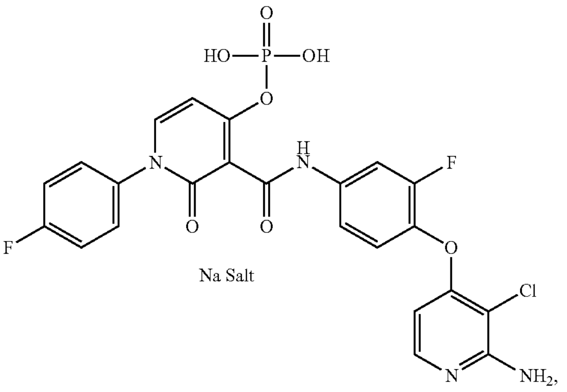

-continued
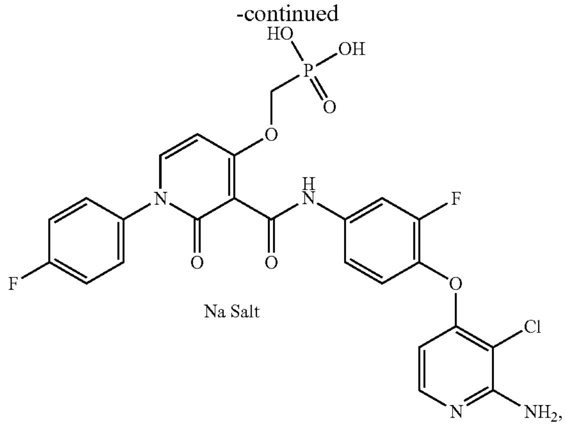
Na Salt
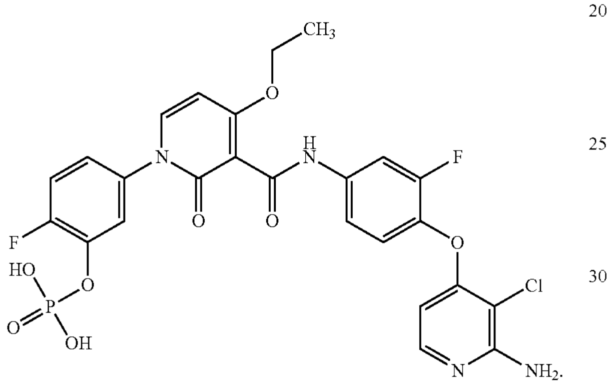
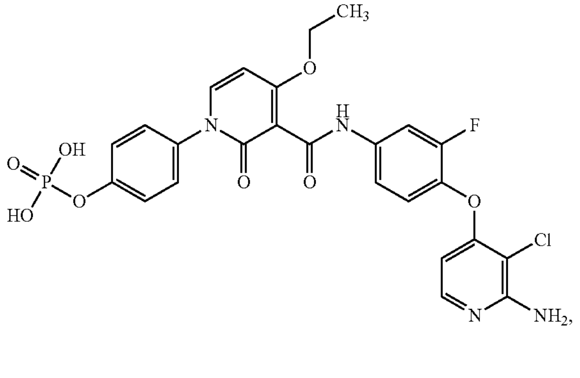
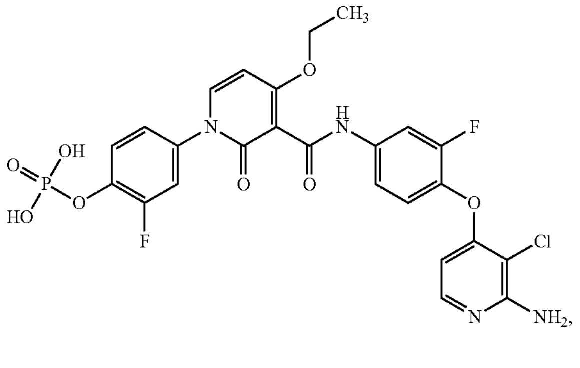
-continued
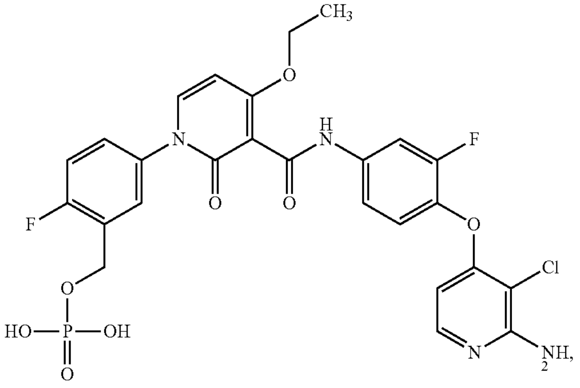
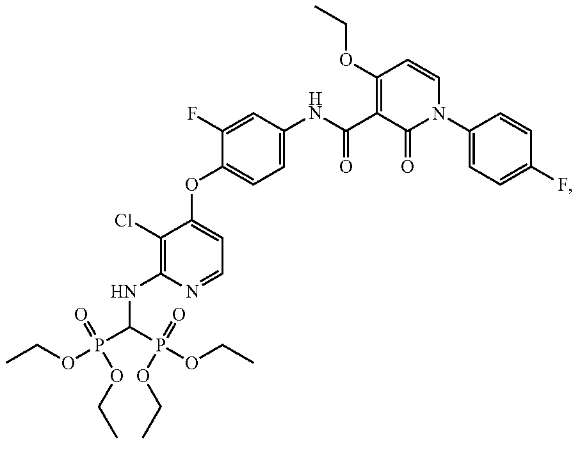
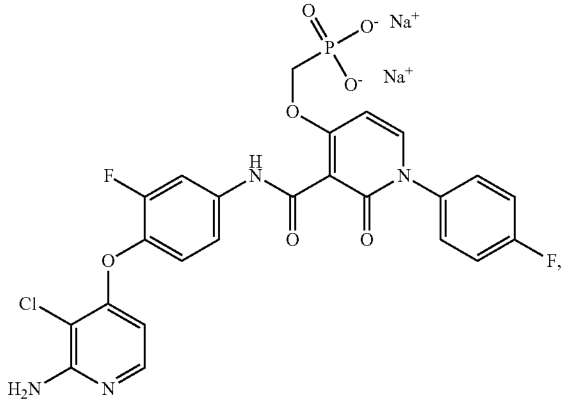
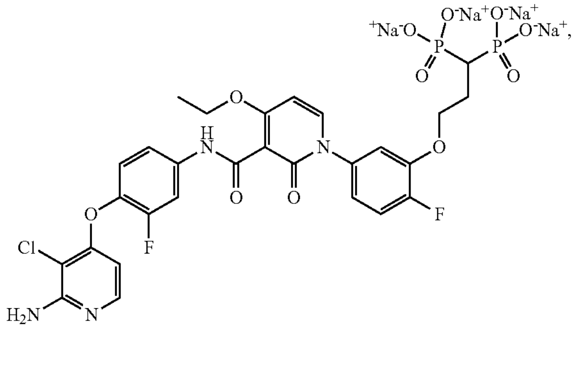

-continued

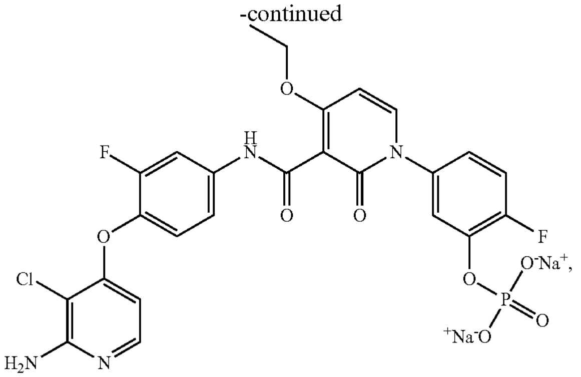

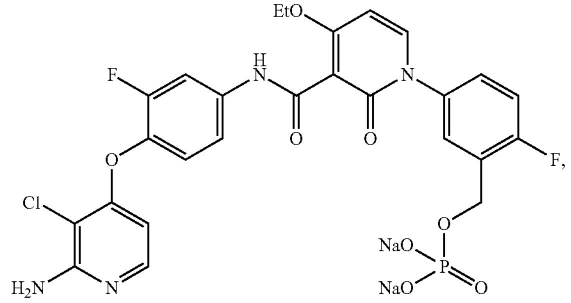

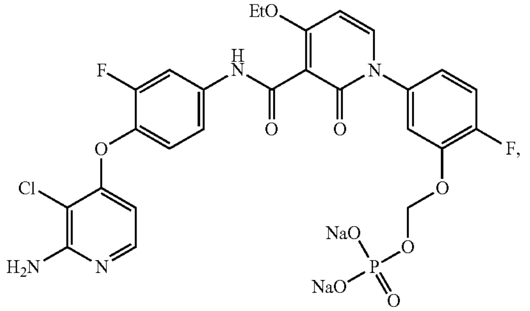

and

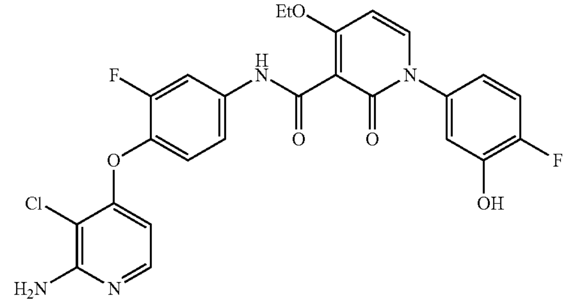

and pharmaceutically acceptable salts, isomers, hydrates, solvates, and polymorphs thereof.

The invention also provides a pharmaceutical composition comprising a therapeutically effective amount of any of a compound of the invention and a pharmaceutically acceptable carrier.

The invention also provides a method for the treatment of a disorder of uncontrolled cellular proliferation in a mammal, the method comprising the step of administering to the mammal an effective amount of any of the compounds of the invention.

The invention also provides a method for inhibiting Ron tyrosine kinase activity in a mammal, the method comprising the step of administering to the mammal an effective amount of any of the compounds of the invention.

In one aspect, the disclosed compounds are selective for Ron. In a further aspect, selective inhibition of Ron tyrosine kinase activity is determined using an enzyme assay.

In one aspect, the disclosed compounds and products of disclosed methods of making inhibit cell growth. In a still further aspect, the disclosed compounds and products of disclosed methods inhibit cell growth in an in vitro assay system. In an even further aspect, the in vitro assay system makes use of a cell-line derived from a from cancer or tumor selected from breast cancer, ovarian cancer, testicular cancer, lung cancer, liver cancer, prostate cancer, pancreatic cancer and a sarcoma. In a yet further aspect, the cell-line is derived from a human source. In a still further aspect, the cell-line is selected from AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG. In one aspect, the disclosed compounds exhibit inhibition of cell growth activity in an in vitro cell-based assay with an $IC_{50}$ of less than about 500 μM, of less than about 250 μM, less than about 100 μM, less than about 50 μM, less than about 10 μM, less than about 1 μM, less than about 500 nM, of less than about 100 nM, of less than about 10 nM, and of less than about 1 nM.

In one aspect, the disclosed compounds and products of disclosed methods of making inhibit cell migration. In a still further aspect, the disclosed compounds and products of disclosed methods inhibit cell migration in an in vitro assay system. In an even further aspect, the in vitro assay system makes use of a cell-line derived from a from cancer or tumor selected from breast cancer, ovarian cancer, testicular cancer, lung cancer, liver cancer, prostate cancer, pancreatic cancer and a sarcoma. In a yet further aspect, the cell-line is derived from a human source. In a still further aspect, the cell-line is selected from AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG. In one aspect, the disclosed compounds exhibit inhibition of cell migration in an in vitro cell-based assay with an $IC_{50}$ of less than about 300 μM, less than about 100 μM, less than about 50 μM, less than about 10 μM, less than about 1 μM, less than about 500 nM, or of less than about 100 nM.

C. Methods of Making the Compounds

In one aspect, the invention relates to methods of making compounds useful as inhibitors of Ron tyrosine kinase activity. In a further aspect, the products of disclosed methods of making are modulators of Ron activity.

In one aspect, the invention relates to methods of making compounds useful as inhibitors of Ron tyrosine kinase, which can be useful in the treatment of disorders of uncontrolled cellular proliferation.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Where reaction conditions and amounts of ingredients are not stated, it is believed that it is within a skill in the art to determine them.

Table 1 lists some of the compounds of the invention:

TABLE 1

| RON Kinase Inhibitors | Chemical Structure | Chemical Name |
|---|---|---|
| Compound 1 | 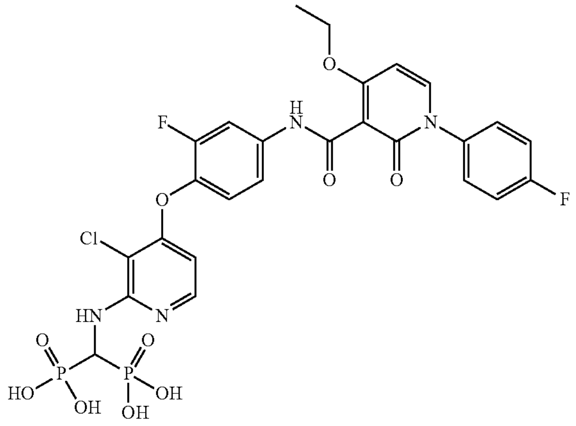 [SMILES: CCOc1ccn(-c2ccc(F)cc2)c(=O)c1C(=O)Nc1ccc(Oc2ccnc(NC(P(=O)(O)O)P(=O)(O)O)c2Cl)c(F)c1] | (((3-chloro-4-(4-(4-ethoxy-1-(4-fluorophenyl)-2-oxo-1,2-dihydropyridine-3-carboxamido)-2-fluorophenoxy)pyridin-2-yl)amino)methylene)diphosphonic acid |
| Compound 2 | 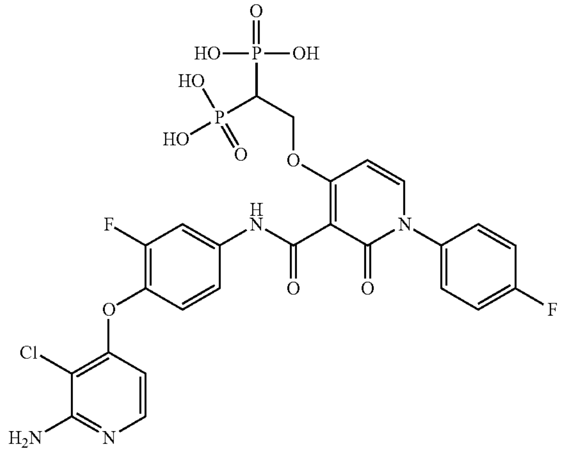 Na Salt | (2-((3-((4-((2-amino-3-chloropyridin-4-yl)oxy)-3-fluorophenyl)carbamoyl)-1-(4-fluorophenyl)-2-oxo-1,2-dihydropyridin-4-yl)oxy)ethane-1,1-diyl)diphosphonic acid |
| Compound 3 | 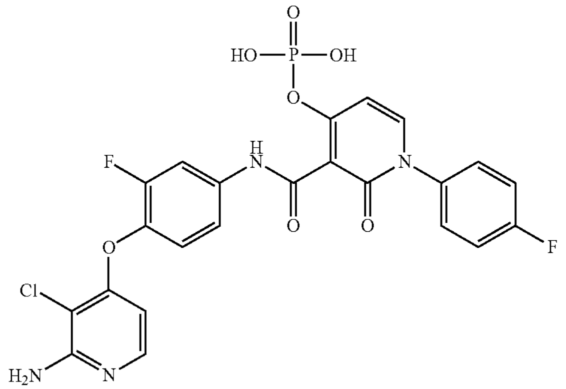 Na Salt | 3-((4-((2-amino-3-chloropyridin-4-yl)oxy)-3-fluorophenyl)carbamoyl)-1-(4-fluorophenyl)-2-oxo-1,2-dihydropyridin-4-yl dihydrogen phosphate |

TABLE 1-continued

| RON Kinase Inhibitors | Chemical Structure | Chemical Name |
|---|---|---|
| Compound 4 | 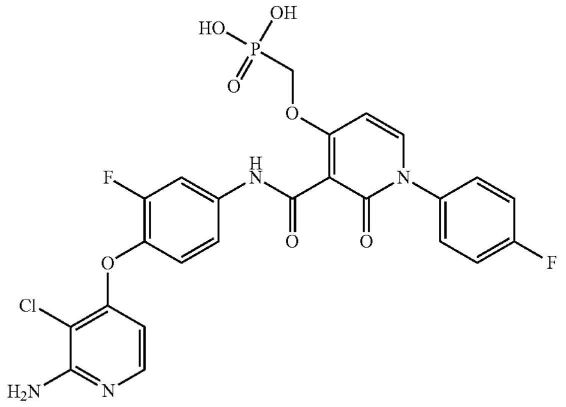 Na Salt | (((3-((4-((2-amino-3-chloropyridin-4-yl)oxy)-3-fluorophenyl)carbamoyl)-1-(4-fluorophenyl)-2-oxo-1,2-dihydropyridin-4-yl)-oxy)methyl)phosphonic acid |
| Compound 5 | 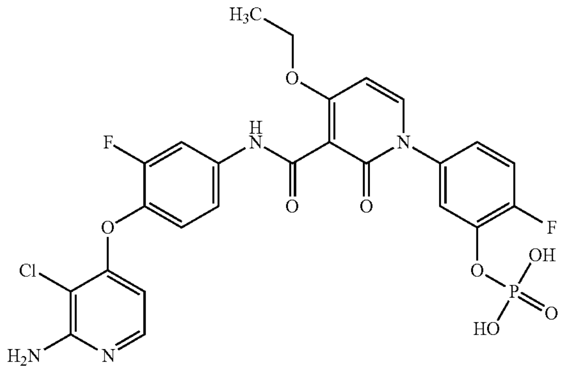 [SMILES: CCOc1ccn(-c2ccc(F)c(OP(=O)(O)O)c2)c(=O)c1C(=O)Nc1ccc(Oc2ccnc(N)c2Cl)c(F)c1] | 5-(3-((4-((2-amino-3-chloropyridin-4-yl)oxy)-3-fluorophenyl)carbamoyl)-4-ethoxy-2-oxopyridin-1(2H)-yl)-2-fluorophenyl dihydrogen phosphate |
| Compound 6 | 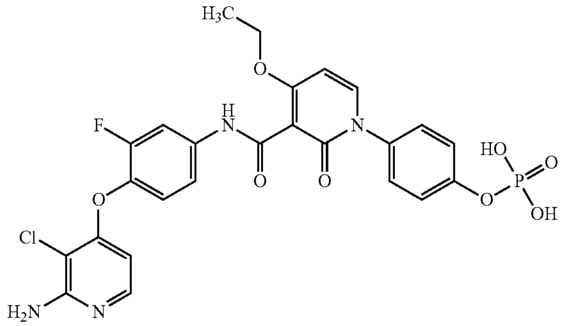 [SMILES: CCOc1ccn(-c2ccc(OP(=O)(O)O)cc2)c(=O)c1C(=O)Nc1ccc(Oc2ccnc(N)c2Cl)c(F)c1] | 4-(3-((4-((2-amino-3-chloropyridin-4-yl)oxy)-3-fluorophenyl)carbamoyl)-4-ethoxy-2-oxopyridin-1(2H)-yl)phenyl dihydrogen phosphate |
| Compound 7 | 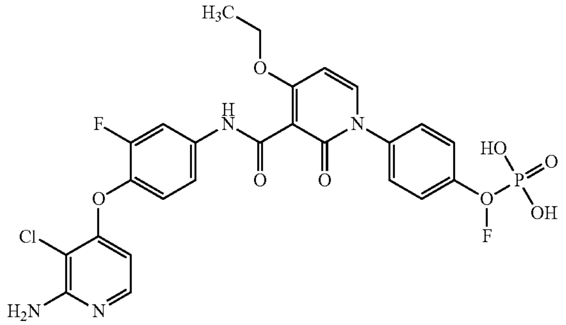 | 4-(3-((4-((2-amino-3-chloropyridin-4-yl)oxy)-3-fluorophenyl)carbamoyl)-4-ethoxy-2-oxopyridin-1(2H)-yl)-2-fluorophenyl dihydrogen phosphate |

TABLE 1-continued

| RON Kinase Inhibitors | Chemical Structure | Chemical Name |
|---|---|---|
| Compound 8 | 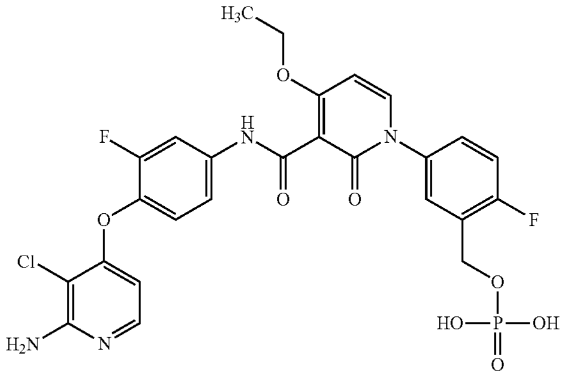 [SMILES: CCOc1ccn(-c2ccc(F)c(COP(=O)(O)O)c2)c(=O)c1C(=O)Nc1ccc(Oc2ccnc(N)c2Cl)c(F)c1] | 5-(3-((4-((2-amino-3-chloropyridin-4-yl)oxy)-3-fluorophenyl)carbamoyl)-4-ethoxy-2-oxopyridin-1(2H)-yl)-2-fluorobenzyl dihydrogen phosphate |
| Compound 9 | 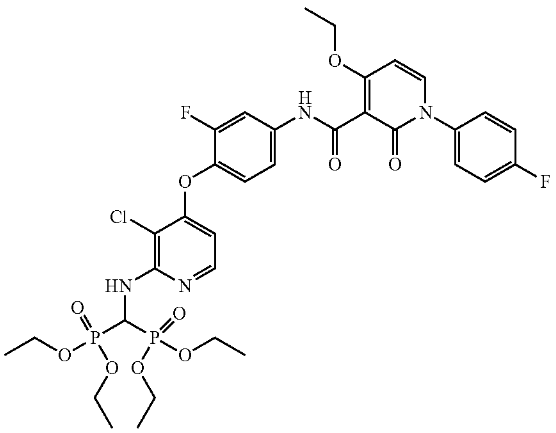 MW 799.17 | tetraethyl (((3-chloro-4-(4-(4-ethoxy-1-(4-fluoro-phenyl)-2-oxo-1,2-dihydro-pyridine-3-carboxamido)-2-fluorophenoxy)pyridin-2-yl)amino)methylene)bis-(phosphonate) |
| Compound 10 | 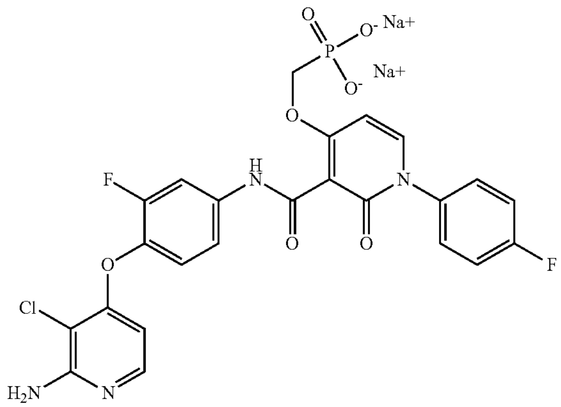 100 mg Synthesized | (((3-((4-((2-amino-3-chloropyridin-4-yl)oxy)-3-fluorophenyl)carbamoyl)-1-(4-fluorophenyl)-2-oxo-1,2-dihydropyridin-4-yl)-oxy)methyl)phosphonate |

TABLE 1-continued

| RON Kinase Inhibitors | Chemical Structure | Chemical Name |
|---|---|---|
| Compound 11 | 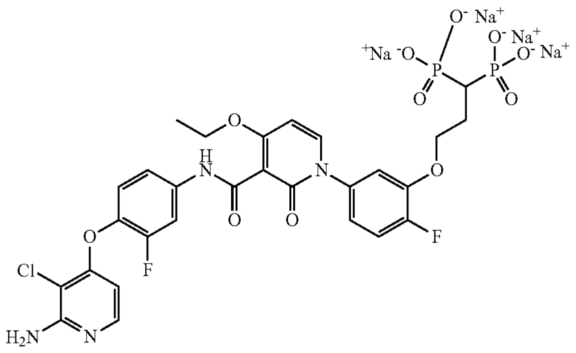 10 mg Synthesized | sodium (3-(5-(3-((4-((2-amino-3-chloropyridin-4-yl)oxy)-3-fluorophenyl)-carbamoyl)-4-ethoxy-2-oxopyridin-1(2H)-yl)-2-fluorophenoxy)propane-1,1-diyl)bis(phosphonate) |
| Compound 12 | 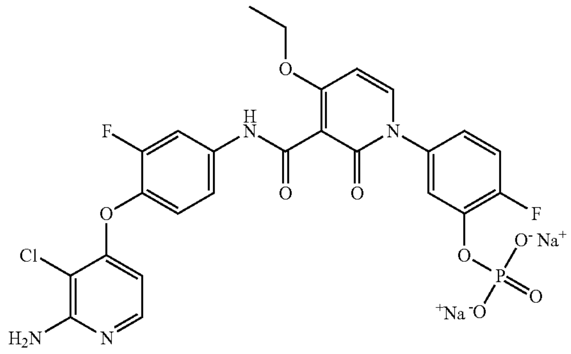 500 mg Scale synthesized | sodium 5-(3-((4-((2-amino-3-chloropyridin-4-yl)oxy)-3-fluorophenyl)carbamoyl)-4-ethoxy-2-oxopyridin-1(2H)-yl)-2-fluorophenyl phosphate |
| Compound 13 | 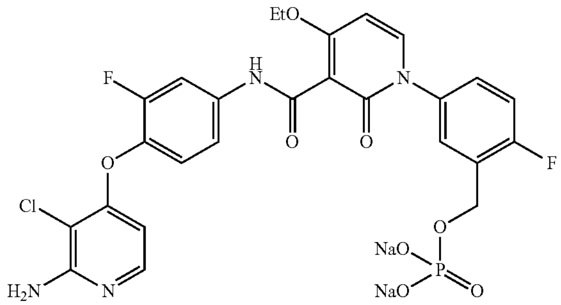 14 mg synthesized | sodium 5-(3-((4-((2-amino-3-chloropyridin-4-yl)oxy)-3-fluorophenyl)carbamoyl)-4-ethoxy-2-oxopyridin-1(2H)-yl)-2-fluorobenzyl phosphate |
| Compound 14 | 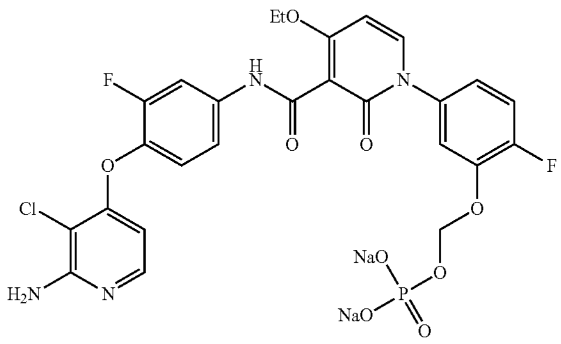 | sodium (5-(3-((4-((2-amino-3-chloropyridin-4-yl)oxy)-3-fluorophenyl)-carbamoyl)-4-ethoxy-2-oxopyridin-1(2H)-yl)-2-fluorophenoxy)methyl phosphate |

TABLE 1-continued

| RON Kinase Inhibitors | Chemical Structure | Chemical Name |
|---|---|---|
| Compound 15 | 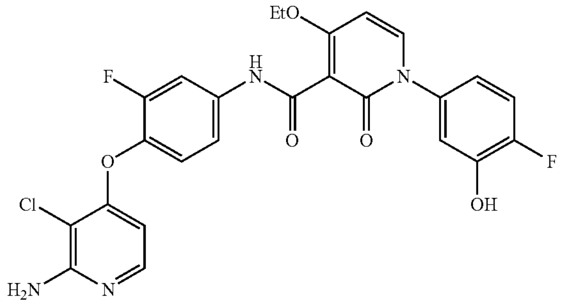 [SMILES: CCOc1ccn(-c2ccc(F)c(O)c2)c(=O)c1C(=O)Nc1ccc(Oc2ccnc(N)c2Cl)c(F)c1] | N-(4-((2-amino-3-chloro-pyridin-4-yl)oxy)-3-fluoro-phenyl)-4-ethoxy-1-(4-fluoro-3-hydroxyphenyl)-2-oxo-1,2-dihydropyridine-3-carboxamide |
| BMS-777607 Reference compound | 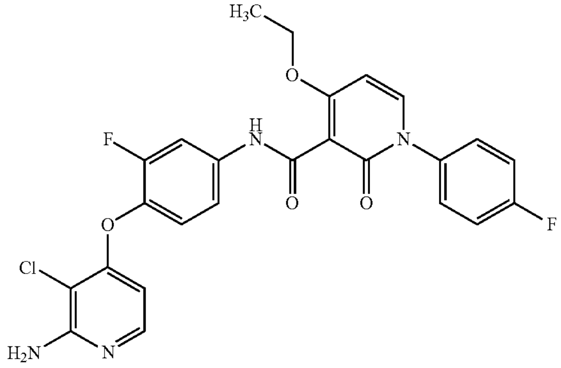 BMS-777607 2 grams Synthesized | |

The inventive compounds may be prepared, for example, utilizing the following general schemes:

Synthesis Scheme for Intermediate A

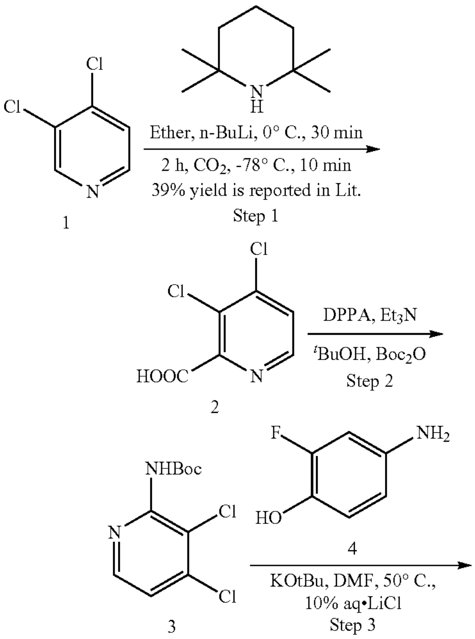

-continued

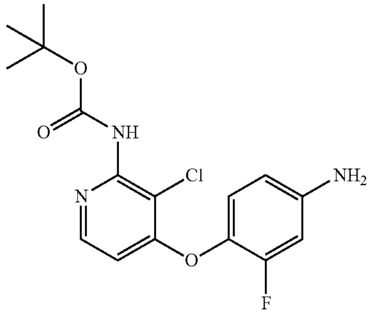

A
Tor targets 1-3

Synthesis Scheme for Intermediate B

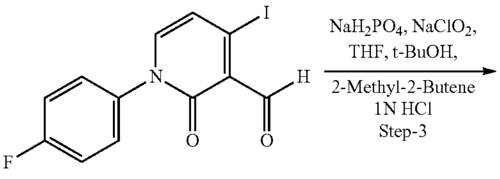

3

-continued
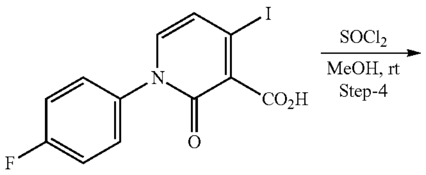
4
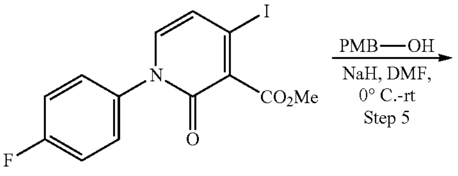
5
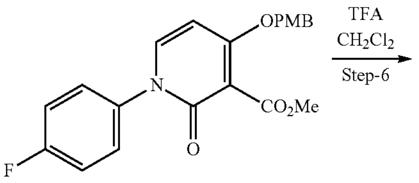
6
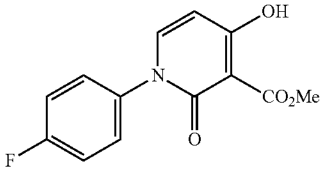
B
Schemes for the Synthesis of Phosphorous Reagent
Synthesis of Bromomethyl Diisopropylphosphate
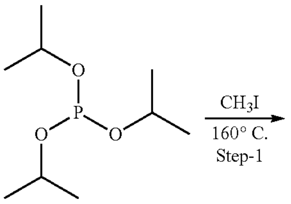
1
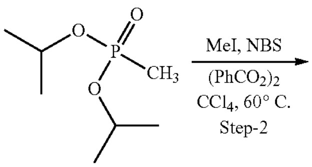
2
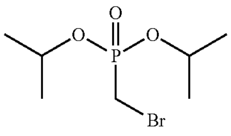
3
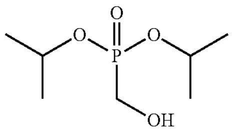
4
Synthesis of Diisopropyl Chlorophosphate
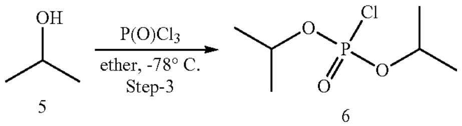
5
6
Synthesis of tetraethyl (2-hydroxyethane-1,1-diyl)bis(phosphonate)
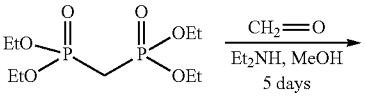
7
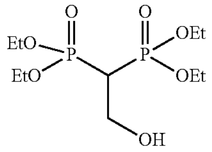
8
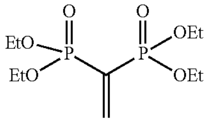
9
Synthesis Scheme for Compound 2
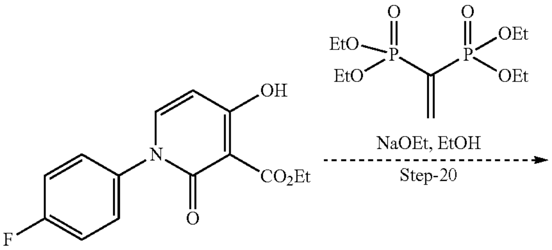
B
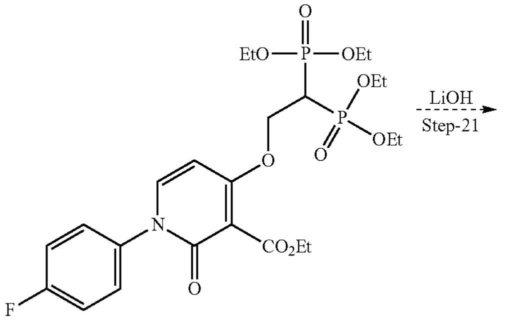
16

-continued
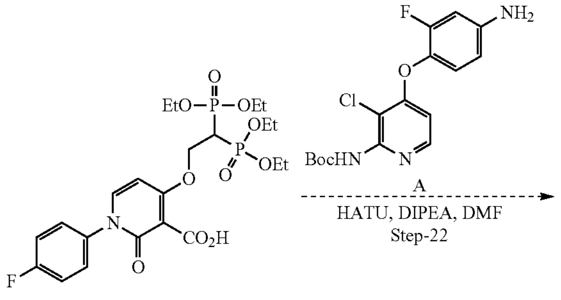
Int B1
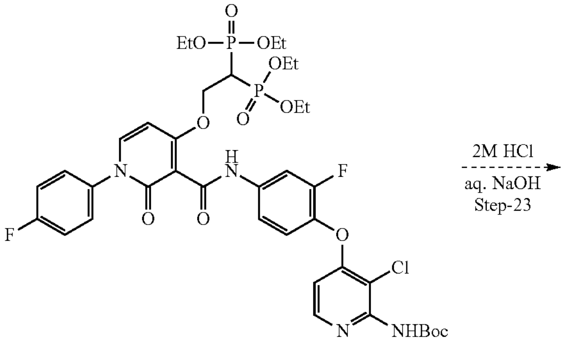
17
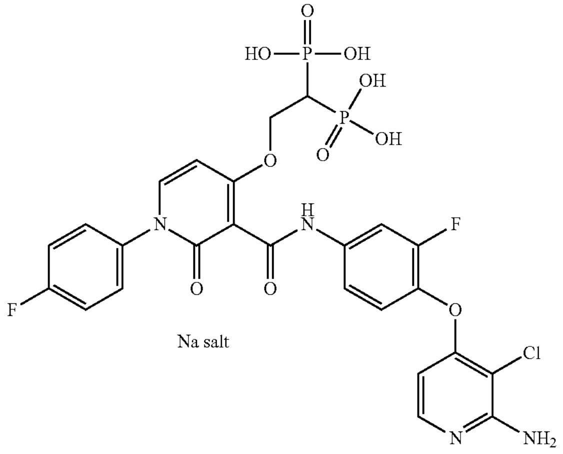
Compound 2
Synthesis Scheme for Compound 3
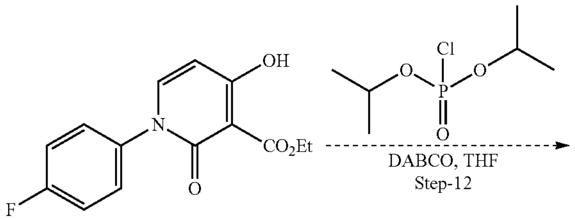
B
-continued
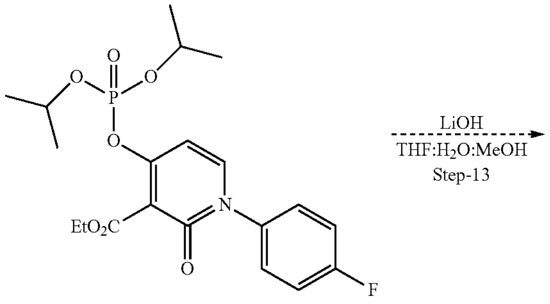
12
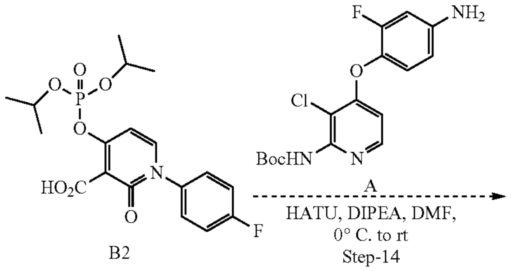
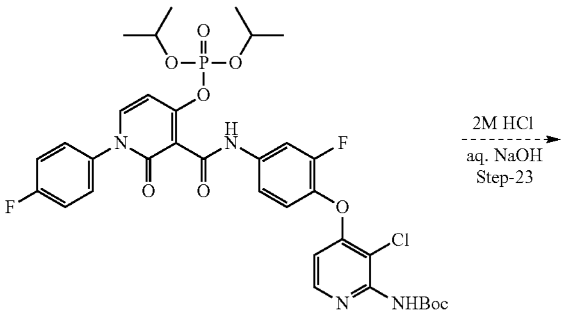
13
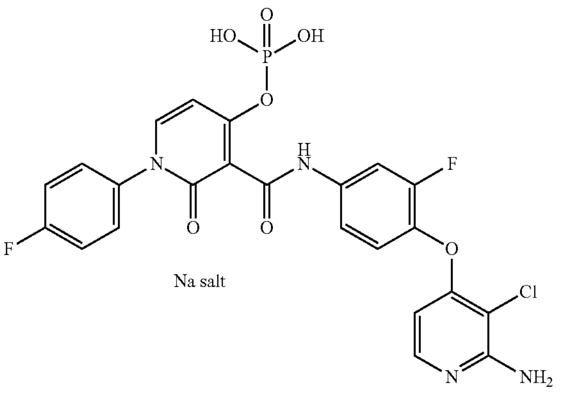
Compound 3

Synthesis Scheme for Compound 4
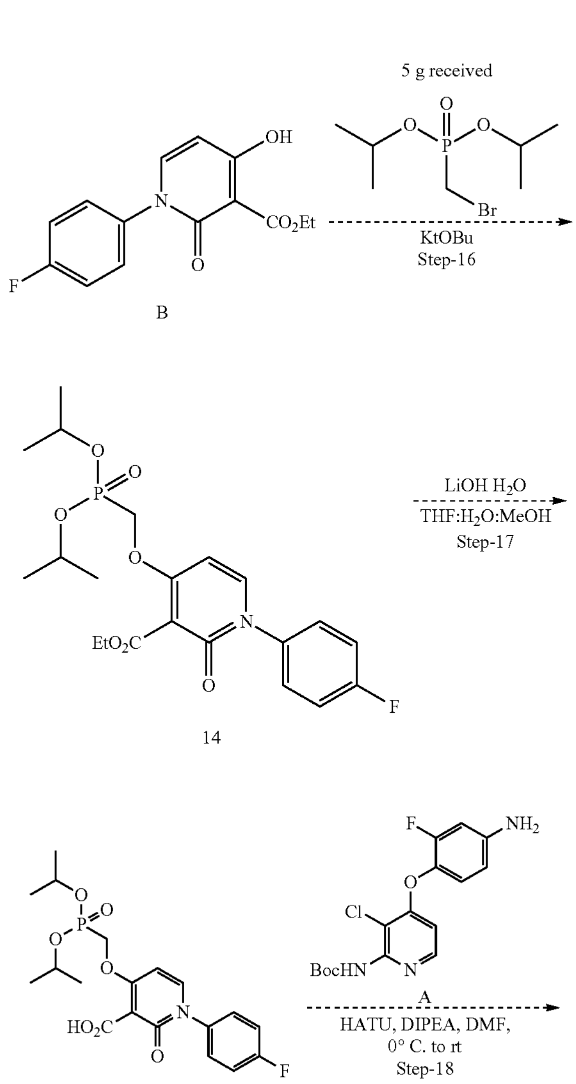
B
14
B3
A
-continued
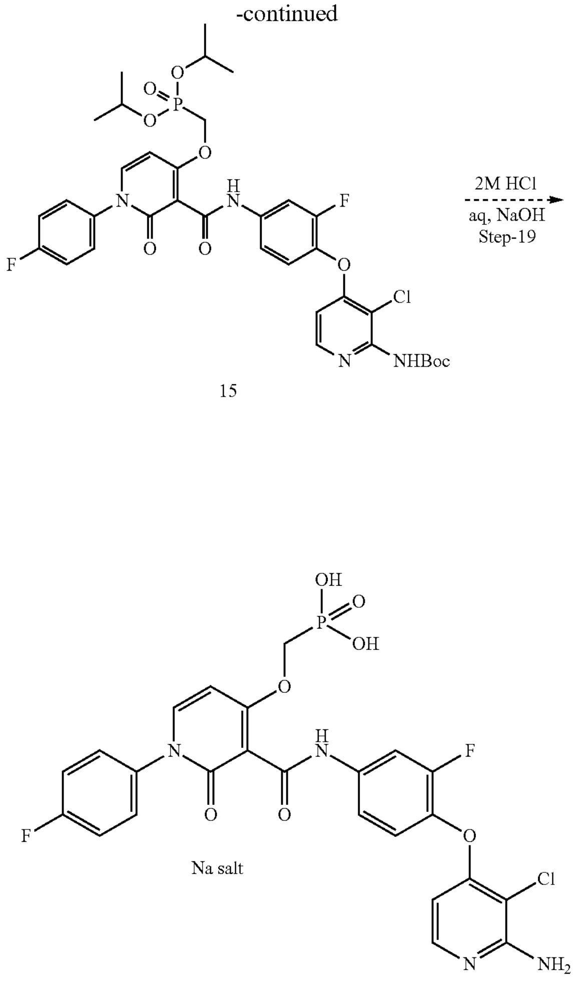
15
Compound 4
Scheme 1: Synthesis of Compound 1 (((3-chloro-4-(4-(4-ethoxy-1-(4-fluorophenyl)-2-oxo-1,2-dihydropyridine-3-carboxamido)-2-fluorophenoxy)pyridin-2-yl)amino)methylene)bis(phosphoric acid)
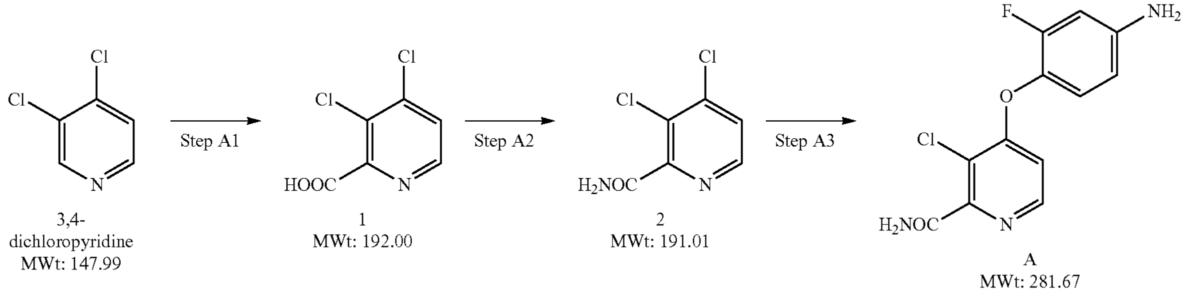
3,4-dichloropyridine MWt: 147.99
1 MWt: 192.00
2 MWt: 191.01
A MWt: 281.67

-continued
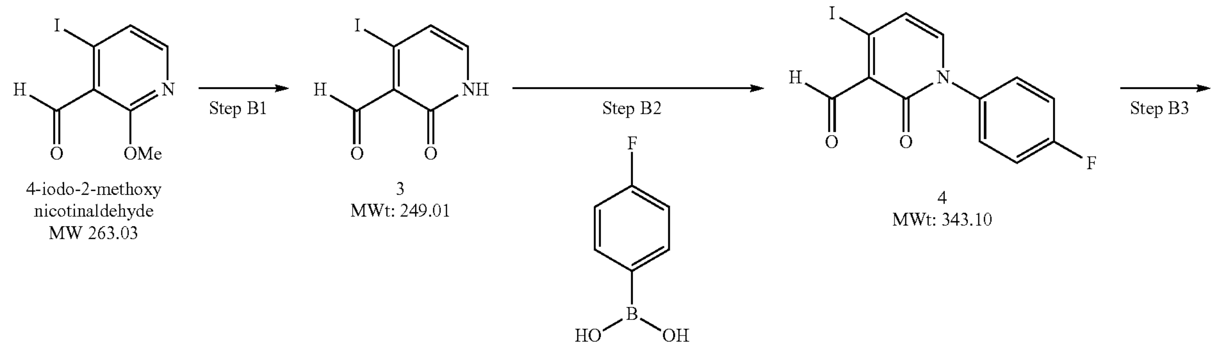
4-iodo-2-methoxy nicotinaldehyde MW 263.03
3 MWt: 249.01
(4-Fluorophenyl)boronic acid
4 MWt: 343.10
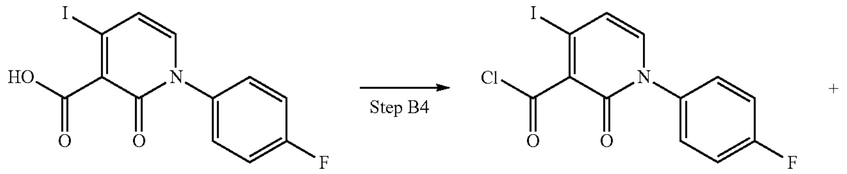
5 MWt: 359.09
B MWt: 377.54
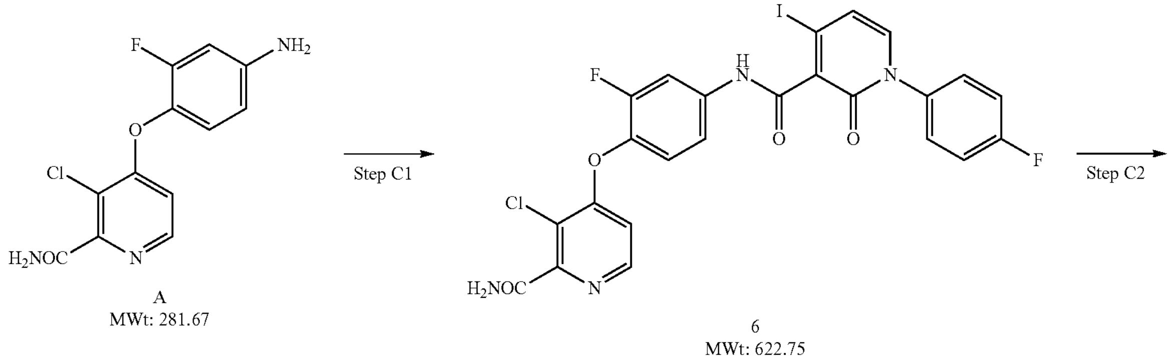
A MWt: 281.67
6 MWt: 622.75
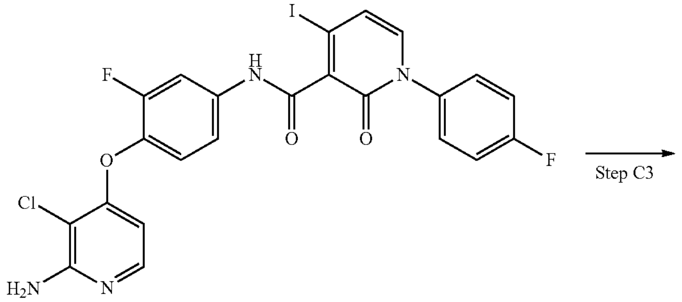
7 MWt: 594.74

-continued
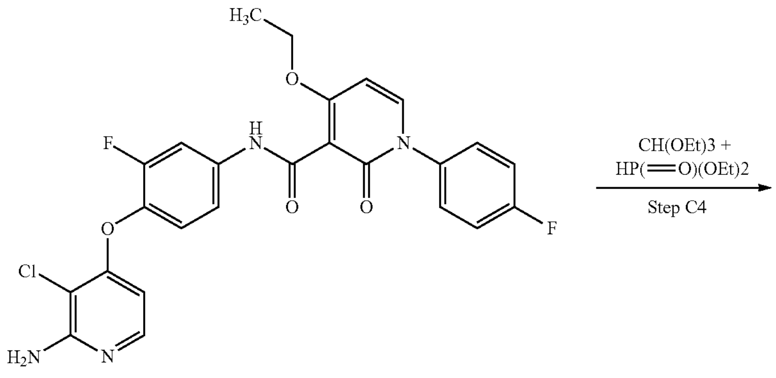
8
MWt: 512.89
Compound A
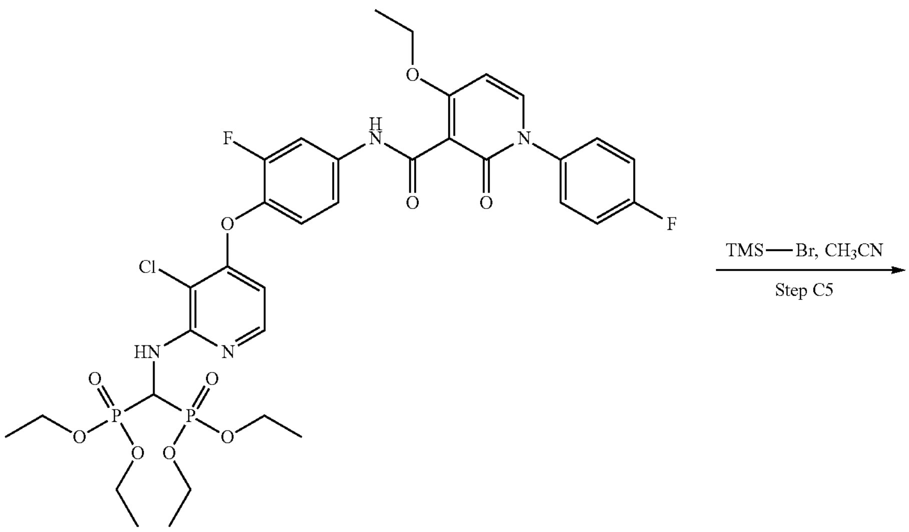
9
MWt: 799.10
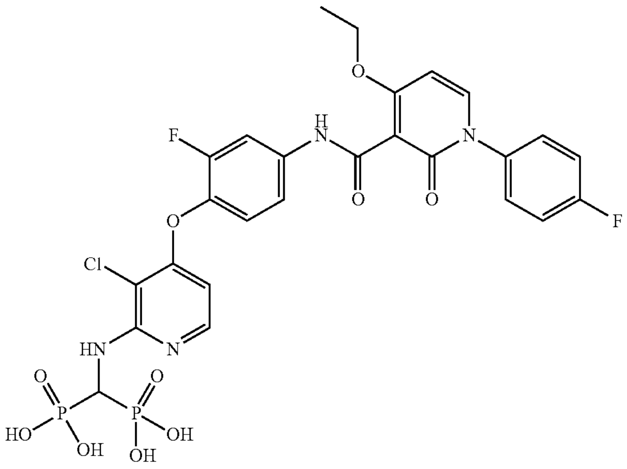
MWt: 686.88
Compound A-bisphosphonate (compound 1)

Preparation of 3,4-dichloropicolinic acid (Step-A1)

1

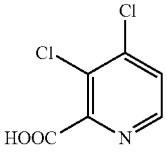

To a stirred solution of 2,2,4,4,-tetramethylpiperdine (12.61 mL, 74.3 mmol) in Diethyl ether (70 mL) was added n-BuLi (46.4 mL, 74.3 mmol) at 0° C., stirred for 30 min. The reaction mixture was cooled to −78° C., added 3,4-dichloropyridine (10 g, 67.5 mmol) in ether (10 mL). The reaction mixture was stirred at −78° C. for 2 h. Then $CO_2$ gas was bubbled into the reaction mixture at −78° C. for 10 min, allowed to warm to RT. The progress of the reaction was monitored by TLC. After completion of reaction, the reaction mixture was quenched with saturated ammonium chloride (50 mL), stirred at RT for 10 min. The reaction mixture was diluted with water (200 mL), extracted with ethyl acetate (2×100 mL). The aqueous layer was acidified with 1N HCl, extracted with ethyl acetate (2×100 mL). Organic layer was dried over anhydrous $Na_2SO_4$, concentrated under reduced pressure to get the title Compound-A1 (5 g, 39% Yield) as off white solid.

$^1$H NMR (DMSO-$d_6$, 400 MHz) δ 8.52 (d, 1H, J=5.2 Hz), 7.88 (d, 1H, J=5.2 Hz):

MS(ESI$^+$) m/z 191.95 (M+H)$^+$.

Preparation of 3,4-dichloropicolinamide (Step-A2)

2

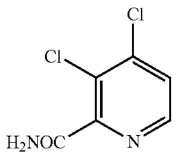

A mixture of 3,4-dichloropicolinic acid (5 g, 18 mmol) in thionyl chloride (20 mL) was stirred at 80° C. for 1 h. The reaction was concentrated in vacuum to remove excess thionyl chloride. The acid chloride in diethyl ether (20 mL) was added to ammonium hydroxide (50 mL) at 0° C. The progress of the reaction was monitored by TLC. After completion of reaction, solid was collected by vacuum filtration, washed with water. The solid was triturated with diethyl ether to get compound-A2 (2.5 g, 50%) as a brown solid.

$^1$H NMR (DMSO-$d_6$, 400 MHz) δ 8.48 (d, 1H, J=5.2 Hz), 8.07 (br s, 1H), 7.82 (d, 1H, J=5.2 Hz), 7.80 (br s, 1H).

MS(ESI$^+$) m/z 190.96 (M+H)$^+$.

Preparation of 4-(4-Amino-2-fluorophenoxy)-3-chloropicolinamide (Step-A2)

A

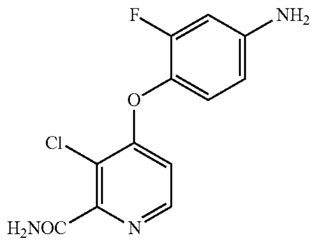

To a stirred solution of 4-amino-2-fluorophenol (468 mg, 3.68 mmol) in DMF (5 mL) was added potassium tert-butoxide (442 mg, 3.945 mmol) at RT, stirred at room temperature for 30 min. Then 3,4-dichloropicolinamide (500 mg, 2.63 mmol) was added to the reaction mixture, stirred at 50° C. for 2.5 h. The progress of the reaction was monitored by TLC. After completion of reaction, the mixture was diluted with 10 mL of ethyl acetate and washed with saturated aqueous sodium bicarbonate solution (10 mL). The aqueous layer was back-extracted with (10 mL) ethyl acetate. The combined organic layers were washed with 10% aqueous lithium chloride solution (10 mL), dried over anhydrous sodium sulfate, and concentrated in vacuum crude as a brown solid. The solid was suspended in ethyl acetate, filtered and washed with diethyl ether to get compound-A2 (350 g, 48%) as a tan solid $^1$H NMR (DMSO-$d_6$, 400 MHz) δ 8.30 (d, 1H, J=5.6 Hz), 8.00 (br s, 1H), 7.70 (br s, 1H), 7.02 (t, 1H, J=9.0 Hz), 6.79 (d, 1H, J=5.44 Hz), 6.53 (dd, 2H, J=10.92 Hz, J=2.2 Hz), 6.54 (dd, 2H, J=6.89 Hz, J=1.77 Hz), (M+H$^+$): 282.12

Preparation of 4-iodo-2-oxo-1,2-dihydropyridine-3-carbaldehyde (Step-B1)

Compound-3

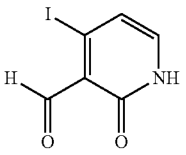

To a stirred solution of 4-iodo-2-methoxynicotinaldehyde (5 g, 19.01 mmol) in Acetonitrile (100 mL) was added Sodium iodide (8.54 g, 57.03 mmol) followed by Chlorotrimethyl silane (7.2 mL, 57.03 mmol) at RT, the reaction mixture was stirred at RT for 2 h. The Progress of the reaction was monitored by TLC. After completion of reaction, the reaction mixture was concentrated under reduced pressure. The crude product was suspended in ethyl acetate, water, and saturated aqueous sodium bicarbonate, (1:1:1) then filtered to give a dark brown solid. This solid triturated with acetonitrile to get the title compound-3 (3.0 g, 65% Yield) as yellow solid.

$^1$H NMR (DMSO-$d_6$, 400 MHz) δ 12.50 (br s, 1H), 9.91 (s, 1H), 7.37 (d, 1H, J=6.63 Hz), 6.85 (d, 1H, J=6.63 Hz). MS(ESI$^+$) m/z 249.95 (M+H)$^+$.

Preparation of 1-(4-fluorophenyl)-4-iodo-2-oxo-1,2-dihydropyridine-3-carbaldehyde (Step-B2)

Compound-4

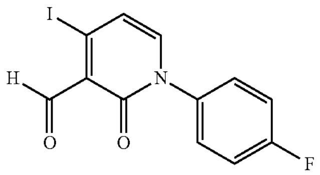

To a stirred solution of compound-3 (5 g, 20.08 mmol) and (4-Fluorophenyl) boronic acid (8.43 g, 60.24 mmol) in toluene (250 mL) was added Cu(II) OAc (7.29 g, 40.16 mmol) Myristic acid (18.33 g, 80.32 mmol) and 2,6-Lutidine (17.2 g, 160.64 mmol) at RT and stirred for 24 h at RT. After 24h an additional of 2.0 g of (4-Fluorophenyl) boronic acid was added and stirred for 72 h at RT. The progress of the reaction was monitored by TLC. After completion of reaction, the reaction mixture was concentrated under vacuum. This crude was suspended in 10% MeOH/Ethyl acetate and filtered through celite plug and washed with ethyl acetate and filtrate was concentrated under vacuum, and suspended in ethyl acetate and water stirred for 5 min and filtered through a celite plug and washed with ethyl acetate and the filtrate was washed with 1N HCl solution, organic layer was dried over anhydrous $Na_2SO_4$, concentrated under reduced pressure to get crude compound. The crude compound was triturated with ethyl acetate to afford the title compound-4 (3.25 g, 47% % Yield) as pale yellow solid.

$^1$H NMR (DMSO-$d_6$, 400 MHz) δ 9.96 (s, 1H), 7.68 (d, 1H, J=7.2 Hz), 7.55-7.52 (m, 2H), 7.37 (t, 2H, J=8.7 Hz), 7.00 (d, 1H, J=7.08 Hz);

Preparation of 1-(4-fluorophenyl)-4-iodo-2-oxo-1,2-dihydropyridine-3-carboxylic acid (Step-B3)

Compound-5

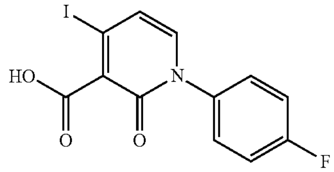

To a stirred solution of compound-4 (500 mg, 1.45 mmol) in THF:t-BuOH:water (1.75 mL) was added sodium phosphate monobasic (568.5 mg, 3.642 mmol) and cool to 0° C., was added 2-methyl 2-butene (2M in THF) (2.3 mL) over a period of 5 min. was added sodium chlorite at same temperature, the reaction mixture was stirred at RT for 2 h. The progress of the reaction was monitored by TLC. The reaction mixture was quenched with 1N HCl precipitated solid was filtered and washed with water dried under vacuum to get the crude title compound-5 (250 mg, 45% Yield) as pale yellow solid.

Rf: 0.2, mobile phase: 10% Methanol in Dichloromethane.

$^1$H NMR (DMSO-$d_6$, 400 MHz) δ 13.33 (s, 1H), 7.50-7.45 (m, 3H), 7.37 (t, 2H, J=8.7 Hz), 6.79 (d, 1H, J=7.2 Hz);

MS(ESI$^+$) m/z: 360.00.

Preparation of 1-(4-fluorophenyl)-4-iodo-2-oxo-1,2-dihydropyridine-3-carbonyl chloride (Step-B4)

Int-B

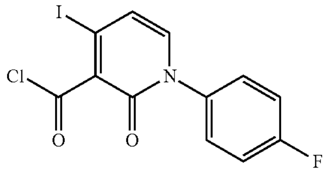

To a stirred solution of compound-3 (2.1 g, 5.84 mmol) in toluene (3.36 mL) was added Thionyl chloride (5.67 mL, 2.7 Vol). The reaction mixture was stirred at RT for 2 h. The progress of the reaction was monitored by TLC. The reaction mixture was evaporated under reduced pressure, and co-distilled with toluene (2×5 mL) and dried under reduced pressure to afford the title Int-B (2.2 g, 95% Yield) as pale yellow solid. Without analysis, proceed to next step.

Preparation of 3-chloro-4-(2-fluoro-4-(1-(4-fluorophenyl)-4-iodo-2-oxo-1,2-dihydropyridine-3-carboxamido) phenoxy) picolinamide (Step-C1)

Compound-6

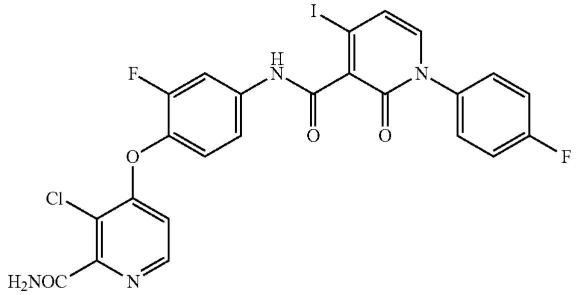

To a stirred solution of 4-(4-amino-2-fluorophenoxy)-3-chloropicolinamide (1.47 g, 5.25 mmol) in THF (30 mL) was added DIPEA (1.13 g, 8.77 mmol) at 0° C. The reaction mixture was stirred at RT for 30 min at 0° C. Then added compound-4 (2.2 g, 5.8 mmol) at 0° C., the reaction mixture was stirred at RT for 2h The progress of the reaction was monitored by TLC. The reaction mixture was quenched with saturated sodium bicarbonate solution and extracted with ethyl acetate (2×50 mL), and washed with brine solution dried over anhydrous $Na_2SO_4$, and evaporated under reduced pressure to get the title compound-6 (2.4 g, 66% Yield as light brown solid. $^1$H NMR (DMSO-$d_6$, 400 MHz) δ 10.86 (s, 1H), 8.31 (d, 1H, J=5.5 Hz), 8.04 (s, 1H), 7.90 (d, 1H, J=12.6 Hz), 7.75 (s, 1H), 7.55 (d, 1H, J=7.1 Hz), 7.53-7.43 (m, 4H), 7.39-7.25 (m, 3H), 6.87-6.84 (m, 2H)

LCMS: purity 97.25%

MS(ESI$^+$) m/z 623.14 (M+H)$^+$.

Preparation of N-(4-((2-amino-3-chloropyridin-4-yl)oxy)-3-fluorophenyl)-1-(4-fluorophenyl)-4-iodo-2-oxo-1,2-dihydropyridine-3-carboxamide (Step-C2)

Compound-7

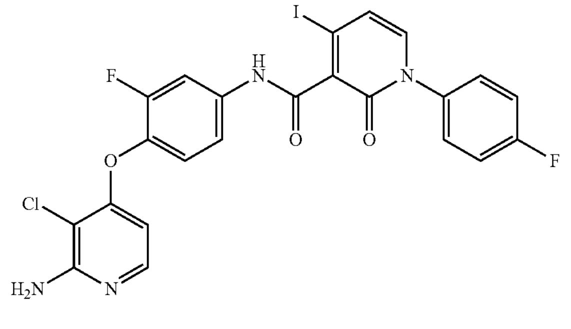

To a stirred solution of Compound-6 (500 mg, 0.803 mmol) in ethyl acetate (4 mL), acetonitrile (4 mL) and water (2m L) at 0° C., was added iodobenzene diacetate (323.6 mg, 1 mmol), The reaction mixture was stirred at RT for 2h, The progress of the reaction was monitored by TLC. The reaction mixture was quenched with saturated sodium bicarbonate solution and extracted with ethyl acetate (2×50 mL), and washed with brine solution dried over anhydrous $Na_2SO_4$, and evaporated under reduced pressure to get the title compound-7 (250 mg, 52%) as brown solid.

$^1$H NMR (DMSO-$d_6$, 400 MHz) δ 10.79 (s, 1H), 7.84 (dd, 1H, J=7.6, 2.2 Hz), 7.73 (d, 1H, J=6.3 Hz), 7.54 (d, 1H, J=7.1 Hz), 7.50-7.41 (m, 3H), 7.39-7.30 (m, 3H), 6.85 (d, 1H, J=7.15 Hz), 6.39 (br s, 2H), 5.94 (d, 1H, J=5.5 Hz).

MS(ESI$^+$) m/z 595.20 (M+H)$^+$.

Preparation of N-(4-((2-amino-3-chloropyridin-4-yl)oxy)-3-fluorophenyl)-4-ethoxy-1-(4-fluorophenyl)-2-oxo-1,2-dihydropyridine-3-carboxamide (Step-C3)

Compound-8

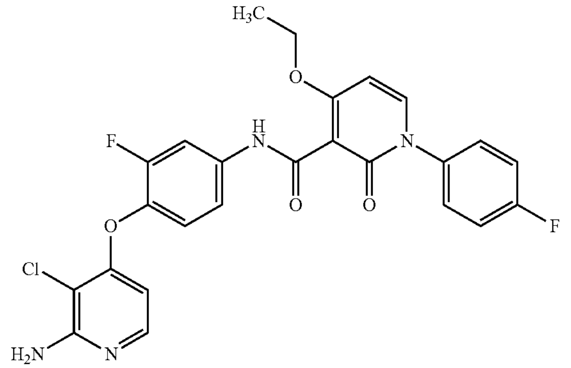

Sodium hydride (4.5 mg, mmol) was added to a solution of ethanol (0.34 mL) and THF (0.34 mL) under nitrogen atmosphere, the resulting mixture was stirred at RT for 10 min. the sodium ethoxide solution was then added to a mixture of Compound-7 (50 mg, mmol), The reaction mixture was stirred at RT for 1 h. The progress of the reaction was monitored by TLC. The reaction mixture was extracted with ethyl acetate (2×20 mL), and washed with brine solution dried over anhydrous $Na_2SO_4$, and evaporated under reduced pressure to get the title compound-8 (30 g, 68%) as light brown solid.

$^1$H NMR (DMSO-$d_6$, 400 MHz) δ 10.54 (s, 1H), 7.87-7.83 (m, 2H), 7.73 (d, 1H, J=5.6 Hz), 7.54 (d, 1H, J=7.1 Hz), 7.46-7.41 (m, 3H), 7.37-7.33 (m, 2H), 7.31 (t, 1H, J=9 Hz), 6.51 (d, 1H, J=7.8 Hz), 6.38 (br s, 2H), 5.92 (d, 1H, J=5.6 Hz), 4.26-4.21 (m, 1H, J=7.1 Hz), 1.28 (t, 1H, J=6.9 Hz)

MS(ESI$^+$) m/z 513.23 (M+H)$^+$.

Preparation of tetraethyl (((3-chloro-4-(4-(4-ethoxy-1-(4-fluorophenyl)-2-oxo-1,2-dihydropyridine-3-carboxamido)-2-fluorophenoxy)pyridin-2-yl)amino)methylene)bis(phosphonate) (Step-C4)

Compound-9

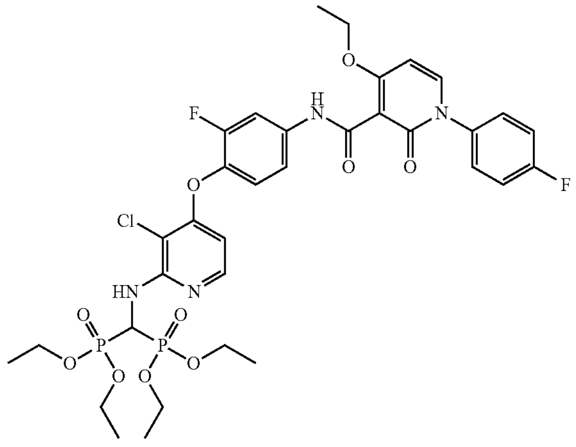

To a stirred solution of N-(4-((2-amino-3-chloropyridin-4-yl)oxy)-3-fluorophenyl)-4-ethoxy-1-(4-fluorophenyl)-2-oxo-1,2-dihydropyridine-3-carboxamide (100 mg, 0.195 mmol) in toluene (2 mL) were added Diethyl phosphate (161 mg, 1.171 mmol) and triethyl orthoformate (34 mg, 0.234 mmol) at RT. The reaction mixture was stirred at 120° C. for 16 h. The progress of the reaction was monitored by TLC. After completion of reaction, the reaction mixture was diluted with DCM (10 mL) and was washed with saturated $NaHCO_3$ solution (5 mL), brine (5 mL) and dried over anhydrous $Na_2SO_4$, concentrated under reduced pressure to get crude compound. The crude compound was purified by preparative TLC by using 7% methanol in ethyl acetate to get title compound-9 (25 mg, 16% Yield) as off white solid.

Rf: 0.4, mobile Phase: 10% methanol in ethyl acetate.

$^1$H NMR (400 MHz, $CDCl_3$) δ 1.25 (s, 15H), 1.56 (s, 4H), 1.58 (s, 2H), 2.04 (s, 2H), 4.11-4.20 (m, 8H), 4.33 (q, 2H), 5.47-5.66 (m, 2H), 6.03-6.04 (d, J=5.58 Hz, 1H), 6.36 (d, J=7.87 Hz, 1H), 7.04 (t, J=8.75 Hz, 1H), 7.21-7.26 (m, 4H), 7.34-7.37 (m, 2H), 7.50 (d, J=7.84 Hz, 1H), 7.82 (d, J=5.72 Hz, 1H), 7.88 (dd, $J_{1,3}$=12.5 Hz, $J_{2,4}$=12.5 Hz 1H), 11.62 (s, 1H).

LC-MS m/z (M+H): 799.17

Preparation of (((3-chloro-4-(4-(4-ethoxy-1-(4-fluorophenyl)-2-oxo-1,2-dihydropyridine-3-carboxamido)-2-fluorophenoxy)pyridin-2-yl)amino)methylene) diphosphonic acid (Step-C5)

Compound 1

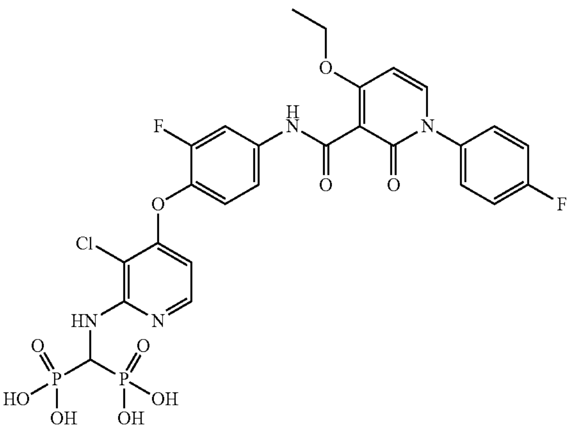

To a stirred solution of tetraethyl (((3-chloro-4-(4-(4-ethoxy-1-(4-fluorophenyl)-2-oxo-1,2-dihydropyridine-3-carboxamido)-2-fluorophenoxy)pyridin-2-yl) amino)methylene)bis(phosphonate) (2×75 mg, 0.0939 mmol) in Acetonitrile (2 mL) was added dropwise TMS-Br (129.5 mg, 0.8458 mmol) in Acetonitrile (1 mL) at 0° C. The reaction mixture was stirred at RT for 36 h. The progress of the reaction was monitored by TLC and LCMS. After completion of reaction, the reaction mixture was concentrated under reduced pressure to get crude compound. The crude compound was purified by Prep-HPLC and lyophilized to get title compound Compound 1 (30 mg, 23% Yield) as off white solid.

Rf: 0.1, Mobile Phase: 10% methanol in DCM.

$^1$H NMR (400 MHz, DMSO) δ 1.28 (t, J=6.93 Hz, 3H), 1.89 (s, 2H), 4.21-426 (m, 3H), 4.5-4.61 (m, 2H), 5.53-5.55 (m, 1H), 5.92-5.93 (d, J=5.75 Hz, 1H), 6.48-6.50 (d, J=7.92 Hz, 1H), 7.26-7.30 (t, J=8.9 Hz, 1H), 7.33-7.37 (t, J=8.75 Hz, 2H), 7.41-7.46 (m, 3H), 7.77-7.78 (d, J=5.73 Hz, 1H), 7.83-7.87 (m, 2H), 10.54 (s, 1H).

LC-MS m/z (M+H): 687.00

Synthesis of Compound 10

Scheme: Synthesis of Sodium (((3-((4-((2-amino-3-chloropyridin-4-yl)oxy)-3-fluorophenyl)carbamoyl)-1-(4-fluorophenyl)-2-oxo-1,2-dihydropyridin-4-yl) oxy)methyl)phosphonate (Compound 10)

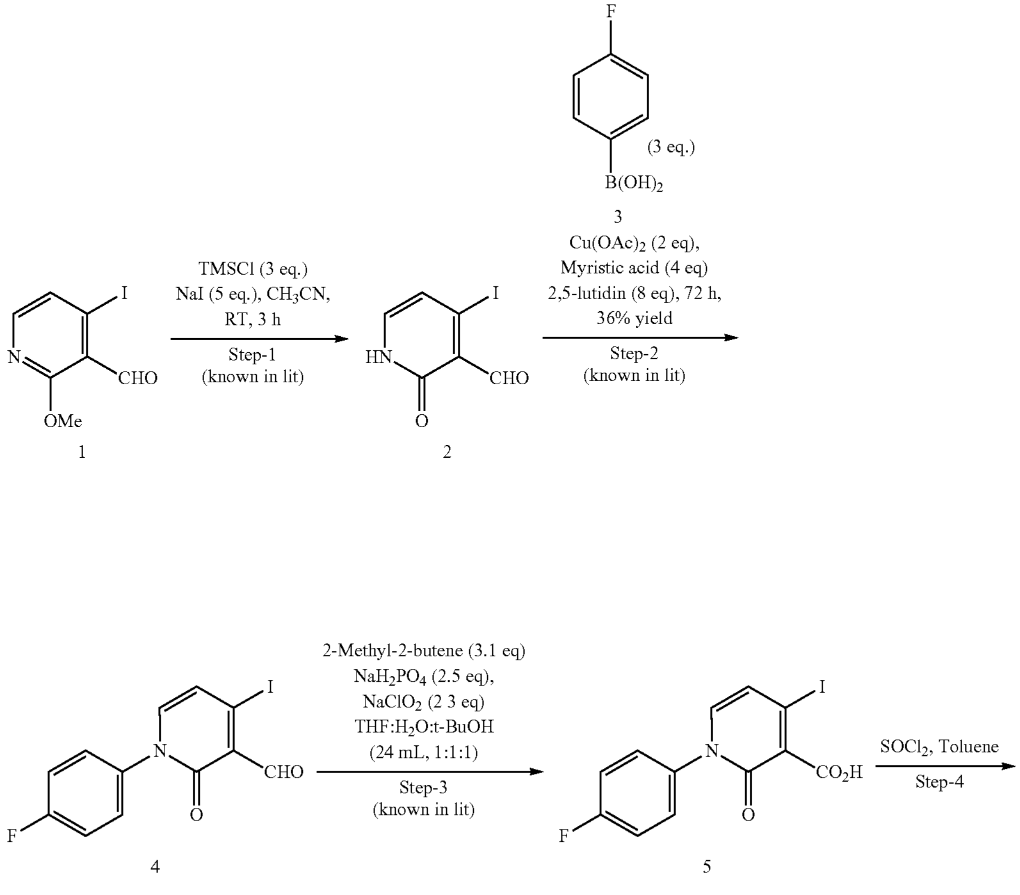

-continued
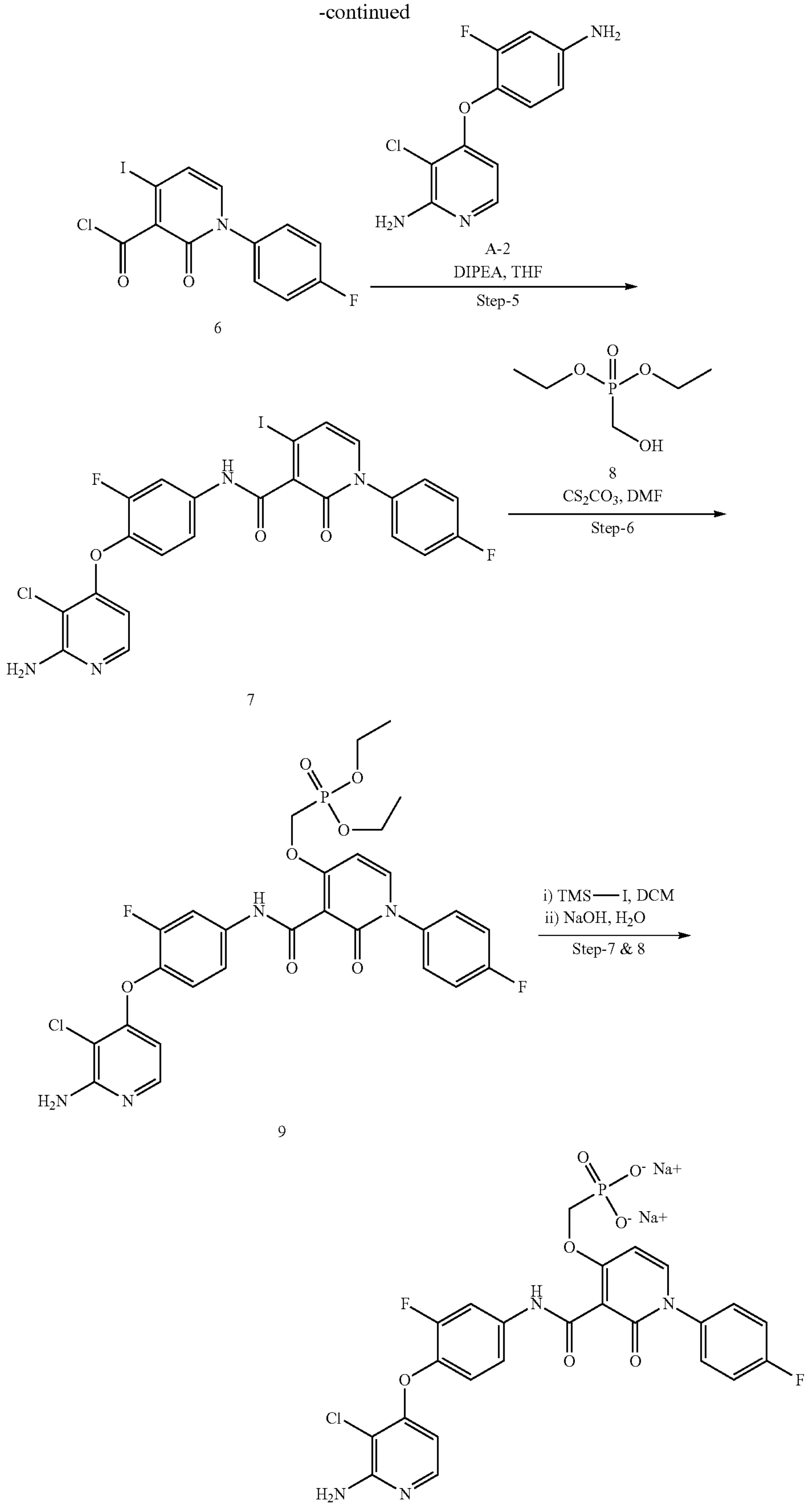
Compound 10

Step-1, 2 & 3 were reported in the article (*J. Med. Chem.* 2009, 52. 1251-1254), the contents of which are hereby incorporated by reference in their entirety.

Preparation of 11-(4-fluorophenyl)-4-iodo-2-oxo-1, 2-dihydropyridine-3-carbonyl chloride (Cpd-6, Step-4)

6

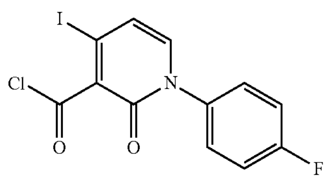

To a stirred solution of Compound-5 (2.1 g, 5.84 mmol) in toluene (10 mL) was added Thionyl chloride (5.67 mL, 2.7 Vol). The reaction mixture was stirred at RT for 2 h and 50° C. for 1 h. The progress of the reaction was monitored by TLC. The reaction mixture was evaporated under reduced pressure, and co-distilled with toluene (2×5 mL) and dried under reduced pressure to afford the title Compound-6 (2.0 g, 90.9% Yield) as a pale yellow solid. Without analysis, proceed to next step.

Preparation of N-(4-((2-amino-3-chloropyridin-4-yl) oxy)-3-fluorophenyl)-1-(4-fluorophenyl)-4-iodo-2-oxo-1,2-dihydropyridine-3-carboxamide (Cpd-7, Step-5)

7

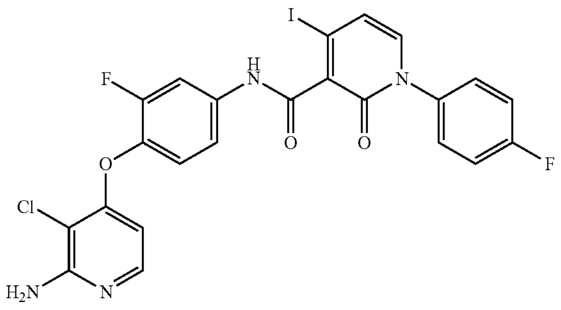

To a stirred solution of Cpd-6 (2.0 g, 5.29 mmol) in THF (30 mL) was added DIPEA (4.62 mL, 26.49 mmol) at 0° C. The reaction mixture was stirred at RT for 30 min at 0° C. Then added Compound-A2 (1.07 g, 4.23 mmol) at 0° C., the reaction mixture was stirred at RT for 2 h. The Progress of the reaction was monitored by TLC. The reaction mixture was quenched with saturated sodium bicarbonate solution and extracted with ethyl acetate (3×100 mL), and combined organic layer was washed with brine solution (2×50 mL), dried over anhydrous $Na_2SO_4$, and evaporated under reduced pressure to get the title Compound-7 (1.6 g, 50.79% Yield) as light brown solid.

Rf: 0.5, Mobile Phase: 5% methanol in DCM.

$^1H$ NMR (400 MHz, DMSO-$d_6$) δ 10.81 (s, 1H), 7.84 (dd, J=7.6, 2.2 Hz, 1H), 7.73 (d, J=5.6 Hz, 1H), 7.54 (d, J=7.1 Hz, 1H), 7.50-7.41 (m, 2H), 7.45-7.29 (m, 4H), 6.85 (d, J=7.2 Hz, 1H), 6.41 (br s, 2H), 5.94 (d, J=5.6 Hz, 1H).

LC-MS m/z (M+H): 594.6

Preparation of diethyl (((3-((4-((2-amino-3-chloro-pyridin-4-yl)oxy)-3-fluorophenyl)carbamoyl)-1-(4-fluorophenyl)-2-oxo-1,2-dihydropyridin-4-yl)oxy) methyl)phosphonate (Cpd-9, Step-6)

9

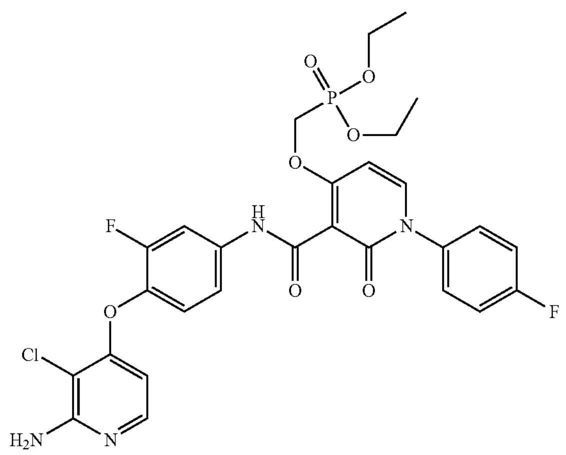

To a stirred solution of Compound-8 (566 mg, 3.36 mmol) in DMF (5 mL) was added $CS_2CO_3$ (1.64 g, 5.04 mmol) at 0° C. under nitrogen atmosphere, the resulting reaction mixture was stirred at 0° C. for 30 min. Then Compound-7 (1.0 g, 1.683 mmol) in DMF (5 mL) was added drop wise to reaction mixture at 0° C. The reaction mixture was stirred at RT for 2 h. The progress of the reaction was monitored by TLC. The reaction mixture was quenched with ice cold water and extracted with ethyl acetate (3×100 mL), and combined organic layer was washed with brine solution (50 mL), dried over anhydrous $Na_2SO_4$, and evaporated under reduced pressure to get the title Compound-9 (700 mg, 70%) as light brown solid.

Rf: 0.3, Mobile Phase: 5% methanol in DCM $^1H$ NMR (400 MHz, DMSO-$d_6$) δ 10.62 (s, 1H), 7.92 (d, J=8 Hz, 1H), 7.86 (d, J=12.4 Hz, 1H), 7.73 (d, J=5.6 Hz, 1H), 7.50-7.28 (m, 6H), 6.62 (d, J=8.4 Hz, 1H), 6.42 (s, 2H), 5.86 (br s, 1H), 4.69 (d, J=10.0 Hz, 2H), 4.1-3.98 (m, 4H), 1.13 (t, J=6.8 Hz, 6H).

LC-MS m/z (M+H): 634.7

Preparation of (((3-((4-((2-amino-3-chloropyridin-4-yl)oxy)-3-fluorophenyl)carbamoyl)-1-(4-fluorophenyl)-2-oxo-1,2-dihydropyridin-4-yl)oxy)methyl) phosphonic acid (Cpd-10, Step-7)

Compound 10

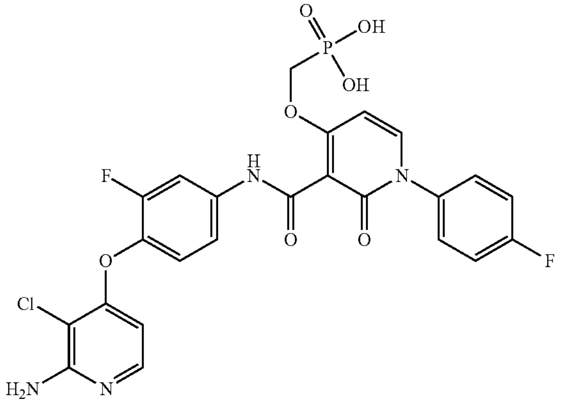

To a stirred solution of compound-9 (350 mg, 0.55 mmol) in DCM (30 mL) was added drop wise TMS-I (0.78 mL, 5.51 mmol) in DCM (2 mL) at 0° C. The reaction mixture was stirred at RT for 1 h. The progress of the reaction was monitored by TLC and LCMS. After completion of reaction, the reaction mixture was concentrated under reduced pressure to get crude compound. The crude compound was purified by Prep-HPLC and pure fractions were lyophilized to get title Compound 10 (140 mg, 44% Yield) as off white solid.

Rf: 0.1, Mobile Phase: 10% methanol in DCM.

$^1$H NMR (400 MHz, DMSO-$d_6$) δ 10.74 (s, 1H), 7.87 (dd, J=2.4, 13.1 Hz, 1H), 7.82 (d, J=7.6 Hz, 1H), 7.72 (d, J=5.6 Hz, 1H), 7.51-7.39 (m, 3H), 7.32 (t, J=8.8 Hz, 2H), 7.30-7.23 (m, 1H), 6.59 (d, J=8.0 Hz, 1H), 6.40 (s, 2H), 5.92 (d, J=5.6 Hz, 1H), 4.33 (d, J=8.4 Hz, 2H).

LC-MS m/z (M+H): 578.7

Preparation of sodium (((3-((4-((2-amino-3-chloropyridin-4-yl)oxy)-3-fluorophenyl)carbamoyl)-1-(4-fluorophenyl)-2-oxo-1,2-dihydropyridin-4-yl)oxy) methyl)phosphonate (Compound 10, Sodium Salt)

Compound 10

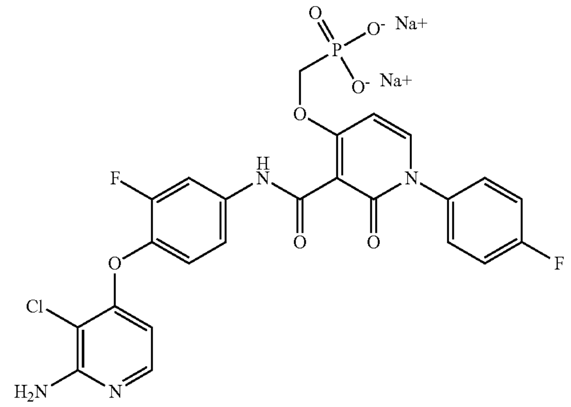

(sodium salt)

To a stirred solution of Compound-10 (140 mg, 0.24 mmol) in DM Water (12 mL) was added drop wise NaOH (17.43 mg, 0.43 mmol) in DM Water (2 mL) at RT. The reaction mixture was stirred at RT for 15 min. The $P^H$ of the reaction mixture was monitored by $P^H$ Paper, after complete addition The $P^H$ was approximately 7-8. Then the reaction mixture was lyophilized to get title compound Compound 10 (sodium salt) (140 mg, 93% yield) as off white solid.

$^1$H NMR (400 MHz, $D_2O$) δ 7.85-7.70 (m, 3H), 7.50-7.40 (m, 3H), 7.31 (t, J=8.4 Hz, 3H), 6.76 (d, J=8.0 Hz, 1H), 6.28 (d, J=5.6 Hz, 1H), 4.27 (d, J=8.8 Hz, 2H). LC-MS m/z (M+H): 578.7

Synthesis of Compound 11

Scheme: Synthesis of (3-(5-(3-((4-((2-amino-3-chloropyridin-4-yl)oxy)-3-fluorophenyl)carbamoyl)-4-ethoxy-2-oxopyridin-1 (2H)-yl)-2-fluorophenoxy) propane-1,1-diyl)bis(phosphonic acid) (Compound 11)

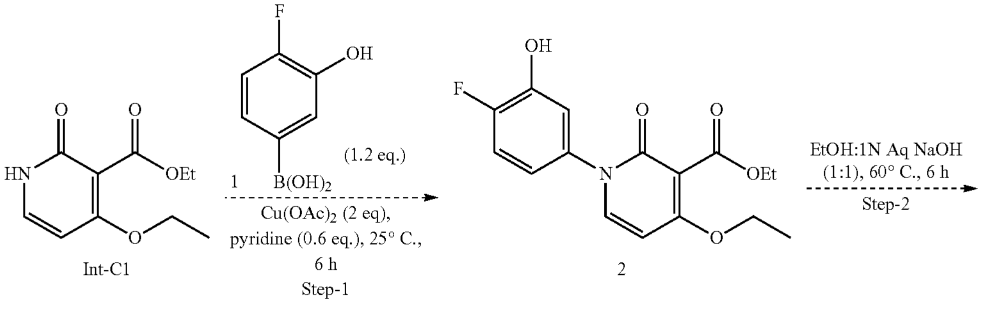

Int-C1

1

2

-continued
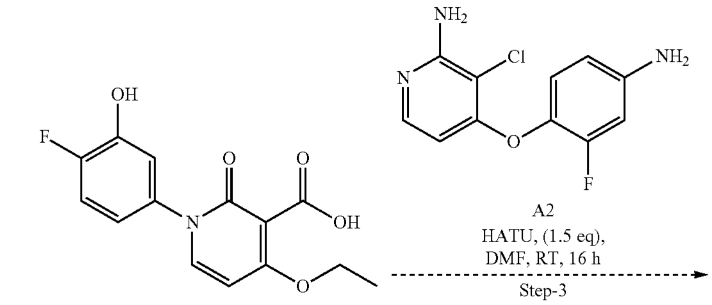
3
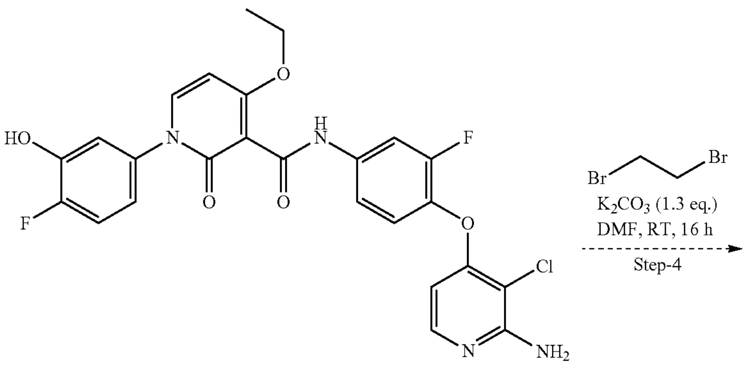
4
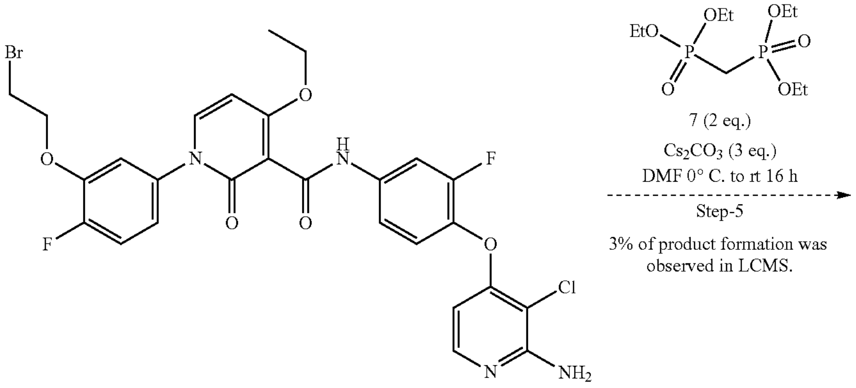
5
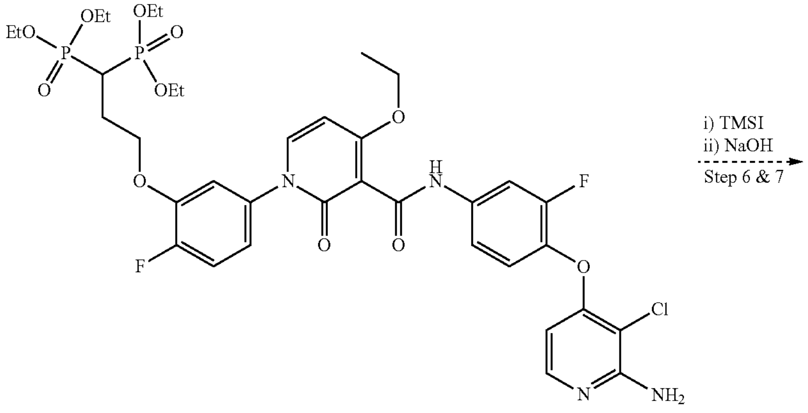
6

-continued
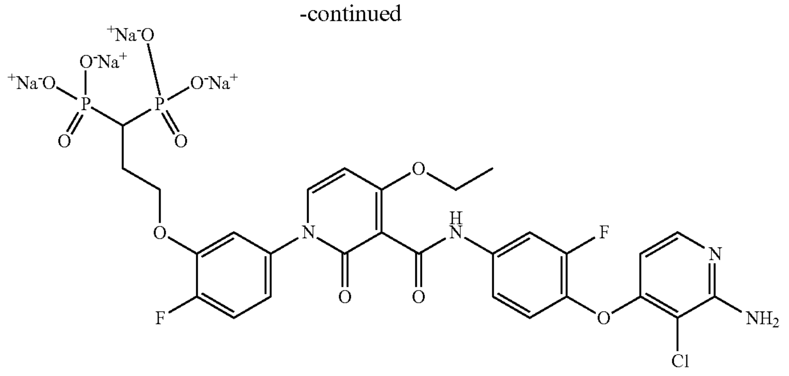
Compound 11
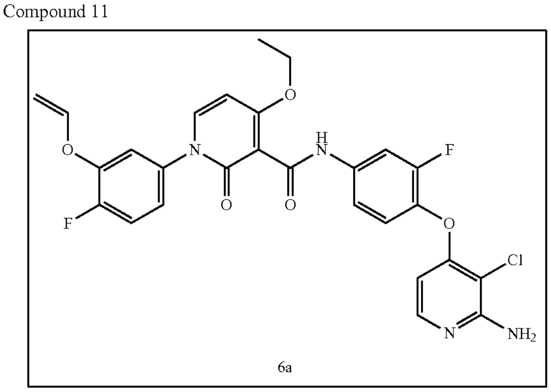
6a
Preparation of Intermediates
Preparation of Int-A2
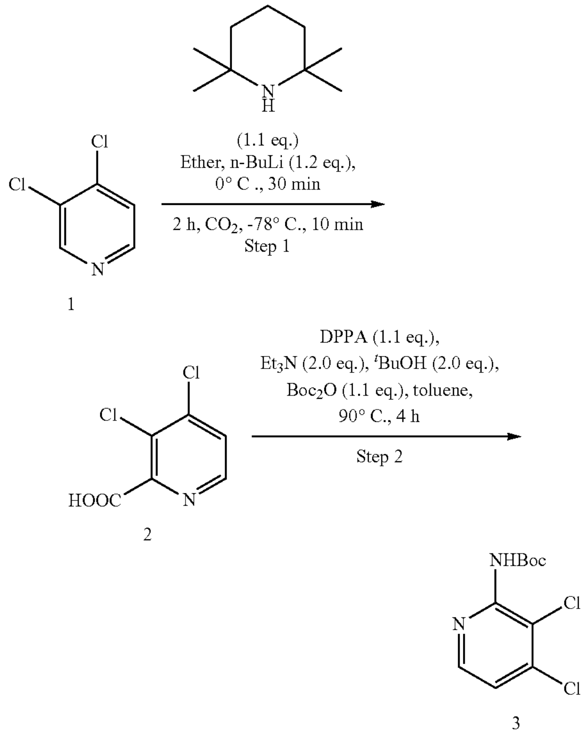
-continued
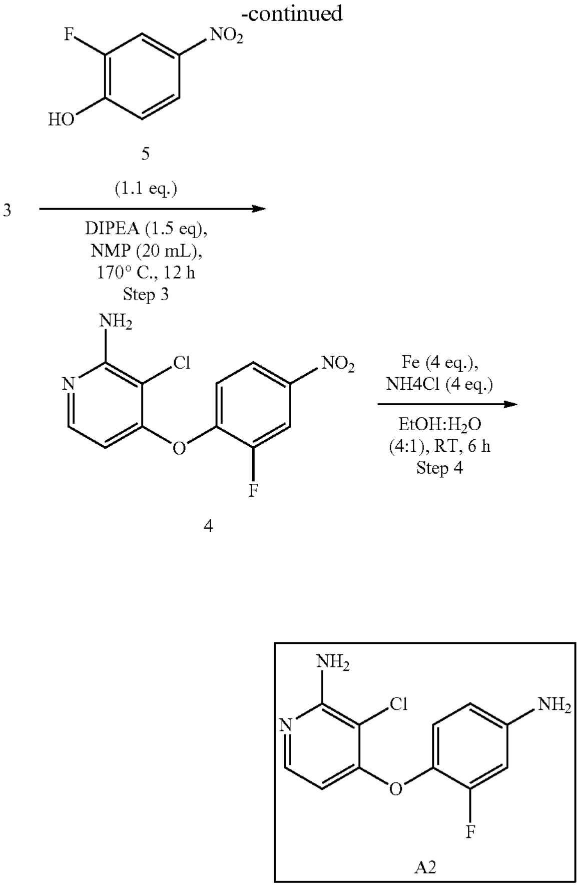

Preparation of 3,4-dichloropicolinic acid (2) (Step-1)

4

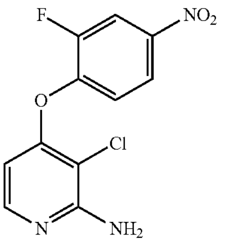

To a stirred solution of 2,2,4,4,-tetramethylpiperdine (31.6 mL, 185.82 mmol) in Diethyl ether (200 mL) was added n-BuLi (116.1 mL, 185.82 mmol) at 0° C., stirred for 30 min. The reaction mixture was cooled to −78° C., added 3,4-dichloropyridine 1 (25 g, 168.93 mmol) in ether (40 mL). The reaction mixture was stirred at −78° C. for 2 h. Then $CO_2$ gas was bubbled into the reaction mixture at −78° C. for 10 min, allowed to warm to RT. The progress of the reaction was monitored by TLC. After completion of reaction, the reaction mixture was quenched with Saturated ammonium chloride (200 mL), stirred at RT for 10 min. The reaction mixture was diluted with water (200 mL), extracted with ethyl acetate (2×200 mL). The aqueous layer was acidified with 1N HCl, extracted with ethyl acetate (2×200 mL). Organic layer was dried over anhydrous $Na_2SO_4$, concentrated under reduced pressure to get the title Compound 2 (12.7 g, 39.1% Yield) as an off-white solid.

$^1$H NMR (DMSO-$d_6$, 400 MHz) δ 14.17 (brs, 1H), δ 8.51 (d, 1H, J=5.2 Hz), 7.88 (d, 1H, J=4.8 Hz); MS(ESI$^+$) m/z 191.97 (M+H)$^+$.

Preparation of tert-butyl (3,4-dichloropyridin-2-yl) carbamate (3) (Step-2)

2

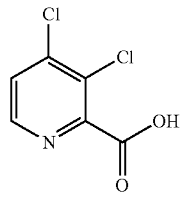

To a stirred solution of 2 (12.7 g, 66.14 mmol) in toluene (150 mL) were added TEA (18.33 mL, 132.29 mmol), Diphenylphosphoryl azide (DPPA) (16.32 mL, 72.76 mmol) at RT, stirred for 30 min., after which tert-butanol (12.73 mL, 132.29 mmol) and Boc anhydride (16.71 mL, 72.76 mmol) were added. The reaction mixture was stirred at 90° C. for 4 h, then was cooled to RT. The solution was diluted with EtOAc (100 mL), washed with 10% aqueous $Na_2CO_3$ (3×50 mL) and brain 50 mL. Organic layer was dried over anhydrous $Na_2SO_4$, concentrated under reduced pressure to get the crude compound. The crude compound was purified through flash column chromatography title Compound 3 (9 g, 51.72% Yield) as a white solid.

$^1$H NMR (DMSO-$d_6$, 400 MHz) δ 9.65 (s, 1H), δ 8.30 (d, 1H, J=5.2 Hz), 7.57 (d, 1H, J=5.2 Hz) 1.43 (s, 9H); MS(ESI$^+$) m/z 262.9 (M+H)$^+$.

Preparation of 3-chloro-4-(2-fluoro-4-nitrophenoxy) pyridin-2-amine (4) (Step-3)

3

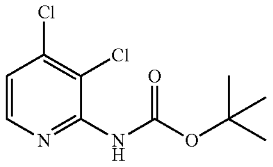

To a stirred solution of 5 (5.90 g, 37.62 mmol) in NMP (20 mL) was placed in glass pressure vessel, then added DIPEA (8.94 mL, 51.3 mmol), at RT, stirred for 30 min., after which 3 (9 g, 34.20 mmol)) was added. The reaction mixture was heated to 170° C. and the heating was continued for 12 h, then the reaction mixture was cooled to RT. The solution was diluted with EtOAc (100 mL), washed with saturated aqueous $NaHCO_3$ solution (3×30 mL). The EtOAc phase was separated washed with brain, and then dried over anhydrous $Na_2SO_4$, concentrated under reduced pressure to get the crude compound. The crude compound was purified through flash column chromatography to get the title Compound 4 (6 g, 61.98% Yield) as a solid.

$^1$H NMR (DMSO-$d_6$, 400 MHz) δ 8.39 (dd, 1H, J=10.4, 2.0 Hz), δ 8.12 (d, 1H, J=8.8 Hz), 7.87 (d, 1H, J=5.6 Hz), 7.40 (t, 1H, J=8.8 Hz), 6.60 (s, 2H), 6.28 (d, 1H, J=5.6 Hz). MS(ESI$^+$) m/z 283.9 (M+H)$^+$.

Preparation of 4-(4-amino-2-fluorophenoxy)-3-chloropyridin-2-amine (A2) (Step-4)

A2

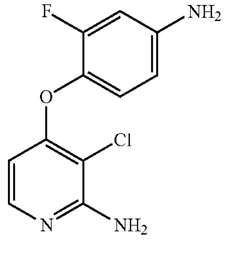

To a stirred solution of 4 (6.0 g, 21.15 mmol) in EtOH/$H_2O$ (240/60 mL) was added $NH_4Cl$ (4.52 g, 84.61 mmol) at RT, stirred for 10 min., after which Fe powder (4.72 g, 84.61 mmol) was added portion wise. The reaction mixture was stirred at RT for 6 h. The reaction mixture was filtered through celite bed. The filtrate was concentrated on rotary evaporator under reduced pressure. The resulting suspense was taken into EtOAc and water. The organic layer was extracted. The aqueous layer twice extracted with EtOAc. The EtOAc layer washed with brain, and then dried over anhydrous $Na_2SO_4$, concentrated under reduced pressure to get the crude compound. The crude compound was purified through flash column chromatography to get the title-Int-A2 (4.1 g, 76.49% Yield) as a solid.

$^1$H NMR (DMSO-$d_6$, 400 MHz) δ 7.70 (d, 1H, J=6.0 Hz), δ 6.95 (t, 1H, J=8.8 Hz), 6.48 (d, 1H, J=13.2 Hz), 6.38 (d, 1H, J=8.4 Hz), 6.31 (s, 2H), 5.83 (d, 1H, J=5.6 Hz), 5.46 (s, 2H).

MS(ESI$^+$) m/z 254.16 $(M+H)^+$.

Steps of the Main Scheme for Synthesis of Compound 11

Preparation of ethyl 4-ethoxy-1-(4-fluoro-3-hydroxyphenyl)-2-oxo-1,2-dihydropyridine-3-carboxylate (Cpd-2, Step-1)

2

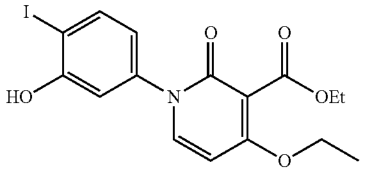

To a stirred solution of Int-C1 (4.0 g, 18.957 mmol, 1 eq.) in dichloromethane (40 mL) was added then cooled to 0° C. and added (4-fluoro-3-hydroxyphenyl) boronic acid 1 (3.5 g, 22.748 mmol, 1.2 eq.), Copper (II) acetate (6.9 g, 37.914 mmol, 2 eq.) and pyridine (0.91 mL, 11.374 mmol, 0.6 eq.). The reaction mixture was stirred at RT for 6 h. The progress of the reaction was monitored by TLC. The reaction mixture was filtered through celite and washed with dichloromethane. The reaction mixture was washed with water (2×80 mL) along washed with brine solution (80 mL), dried over anhydrous $Na_2SO_4$, and evaporated under reduced pressure. The crude material was purified by combi-flash by using ethyl acetate in hexane to obtain the title Compound-2 (2.9 g, 47% Yield) as pale yellow solid.

Rf: 0.5, Mobile Phase: 50% Ethyl acetate in hexane.

$^1$H NMR (400 MHz, DMSO-$d_6$) δ 10.28 (s, 1H), 7.76 (d, J=8.0 Hz, 1H), 7.25 (t, J=9.6 Hz, 1H), 6.92 (d, J=6.4 Hz, 1H), 6.77 (d, J=8.0 Hz, 1H), 6.39 (d, J=8.0 Hz, 1H), 4.20-4.16 (m, 4H), 1.28-1.14 (m, 6H).

LC-MS m/z (M+H): 322.10

Preparation of 4-ethoxy-1-(4-fluoro-3-hydroxyphenyl)-2-oxo-1,2-dihydropyridine-3-carboxylic acid (Cpd-3, Step-2)

3

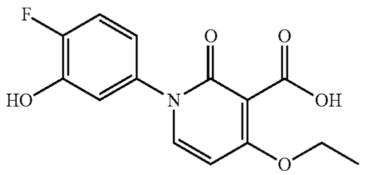

To a stirred solution of Cpd-2 (2.5 g, 7.788 mmol) in ethanol:1N aq NaOH (25:25 mL) was added at RT. The reaction mixture was stirred at 60° C. for 6 h. The Progress of the reaction was monitored by TLC. The reaction mixture was washed with ethyl acetate to remove the organic impurities. The aqueous layer $P^H$ adjust by using HCl ($P^H$=1-2) and then extracted with ethyl acetate (2×50 mL), and combined organic layer was washed with brine solution (50 mL), dried over anhydrous $Na_2SO_4$, and evaporated under reduced pressure to obtain the title Compound-3 (1.1 g, 48% Yield) as white solid.

Rf: 0.2, Mobile Phase: 5% methanol in DCM.

$^1$H NMR (400 MHz, DMSO-$d_6$) δ 13.83 (s, 1H), 10.34 (s, 1H), 7.93 (d, J=7.6 Hz, 1H), 7.28 (t, J=8.8 Hz, 1H), 6.97 (d, J=5.6 Hz, 1H), 6.83 (m, 1H), 6.56 (d, J=8.0 Hz, 1H), 4.27 (q, J=6.4 Hz, 2H), 1.32 (t, J=6.4 Hz, 3H).

LC-MS m/z (M+H): 293.9

Preparation of N-(4-((2-amino-3-chloropyridin-4-yl)oxy)-3-fluorophenyl)-4-ethoxy-1-(4-fluoro-3-hydroxyphenyl)-2-oxo-1,2-dihydropyridine-3-carboxamide (Cpd-4, Step-3)

4

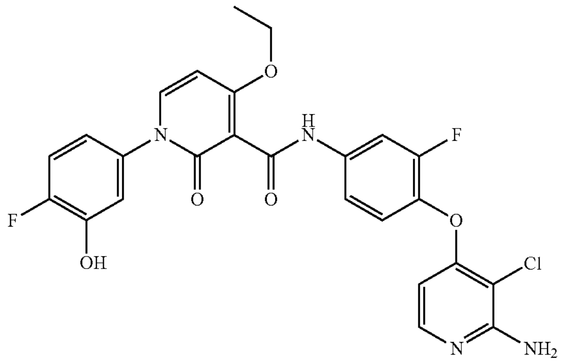

To a stirred solution of Cpd-3 (1 g, 3.412 mmol, 1 eq.) in DMF (5 mL) was added DIPEA (2.6 mL, 10.236 mmol, 3 eq.) and HATU (1.9 g, 5.119 mmol, 1.5 eq.). The reaction mixture was stirred at RT for 15 min. Then added Cpd-A2 (1.3 g, 3.412 mmol, 1 eq.) at RT, the reaction mixture was stirred at RT for 16 h. The Progress of the reaction was monitored by TLC. The reaction mixture was diluted with cold water and extracted with ethyl acetate (2×40 mL), and combined organic layer was washed with brine solution (40 mL), dried over anhydrous $Na_2SO_4$, and evaporated under reduced pressure. The crude material was purified by combi-flash chromatography by using methanol in DCM to obtain the title Compound-4 (1.1 g, 61% Yield) as white solid.

Rf: 0.5, Mobile Phase: 5% methanol in DCM.

$^1$H NMR (400 MHz, DMSO-$d_6$) δ 10.54 (s, 1H), 10.38 (s, 1H), 7.90-7.79 (m, 2H), 7.72 (d, J=5.2 Hz, 1H), 7.41 (d, J=8.0 Hz, 1H), 7.31-7.24 (m, 2H), 6.95 (d, J=6.4 Hz, 1H), 6.77 (m, 1H), 6.46 (d, J=8.0 Hz, 1H), 6.40 (s, 2H), 5.92 (d, J=4.8 Hz, 1H) 4.23-4.22 (m, 2H), 1.27 (t, J=6.8 Hz, 3H).

LC-MS m/z (M+H): 528.8

Preparation of N-(4-((2-amino-3-chloropyridin-4-yl)oxy)-3-fluorophenyl)-1-(3-(2-bromoethoxy)-4-fluorophenyl)-4-ethoxy-2-oxo-1,2-dihydropyridine-3-carboxamide (Cpd-5, Step-4)

5

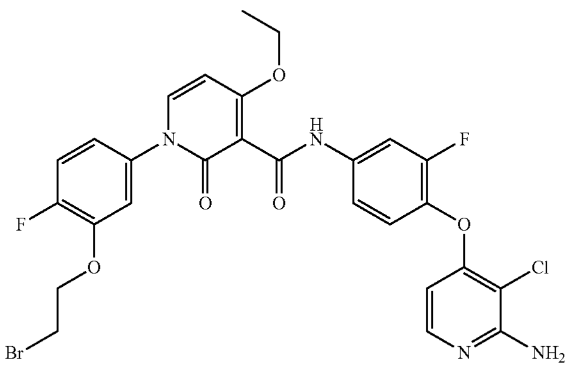

To a stirred solution of Cpd-4 (1 g, 1.893 mmol, 1 eq.) in DMF (10 mL) was added $K_2CO_3$ (312 mg, 2.271 mmol, 1.2 eq.) and 1,2 dibromoethane (0.57 mL, 9.469 mmol, Seq.) at RT under nitrogen atmosphere, the resulting reaction mixture was stirred at RT for 16 h. The progress of the reaction was monitored by TLC. The reaction mixture was quenched with ice cold water and extracted with ethyl acetate (3×30 mL), and combined organic layer was washed with brine solution (30 mL), dried over anhydrous $Na_2SO_4$, and evaporated under reduced pressure. The crude material was purified by combi-flash chromatography by using ethyl acetate in hexane to obtain the title Compound-5 (250 mg, 61%) as white solid.

Rf: 0.4, Mobile Phase: 50% ethyl acetate in hexane $^1H$ NMR (400 MHz, DMSO-$d_6$) δ 10.55 (s, 1H), 7.88-7.84 (m, 2H), 7.72 (d, J=8.8 Hz, 1H), 7.43-7.35 (m, 2H), 7.31-7.24 (m, 2H), 7.00 (m, 1H), 6.50 (d, J=7.6 Hz 1H), 6.40 (s, 2H), 5.92 (d, J=5.2 Hz, 1H) 4.41 (m, 2H), 4.25-4.23 (m, 2H), 3.83 (m, 2H) 1.28 (t, J=6.8 Hz, 3H).

LC-MS m/z (M+H): 634.6

Preparation of tetraethyl (3-(5-(3-((4-((2-amino-3-chloropyridin-4-yl)oxy)-3-fluorophenyl)carbamoyl)-4-ethoxy-2-oxopyridin-1 (2H)-yl)-2-fluorophenoxy)propane-1,1-diyl)bis(phosphonate) (Cpd-6, Step-5)

6

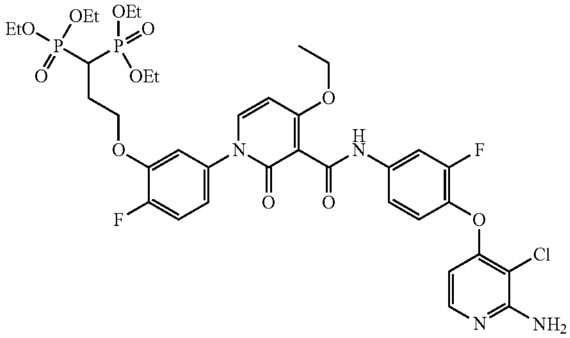

6a

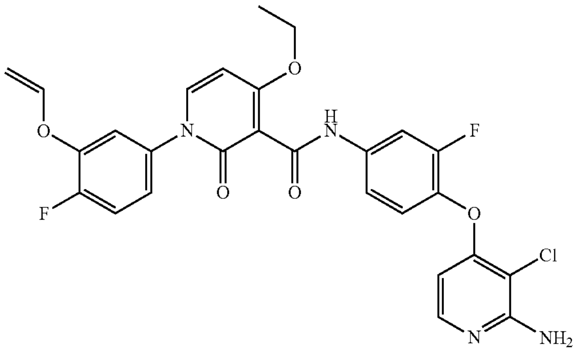

To a stirred solution of Cpd-7 (18 mg, 0.0628 mmol, 2 eq.) in DMF (4 mL) was added $Cs_2CO_3$ (15 mg, 0.0471 mmol, 1.5 eq.) at RT for 2 h. To this added Cpd-5 (20 mg, 0.0314 mmol, 1 eq.) in DMF (2 mL) at RT. The reaction mixture was stirred at RT for 16 h. The progress of the reaction was monitored by TLC and LCMS.

LC-MS Shows 3% of 6 desired product along with 35% of 6a.

LC-MS m/z (M+H): 842.87

An Alternative Plan for the Synthesis of Compound 11 is as Follows:

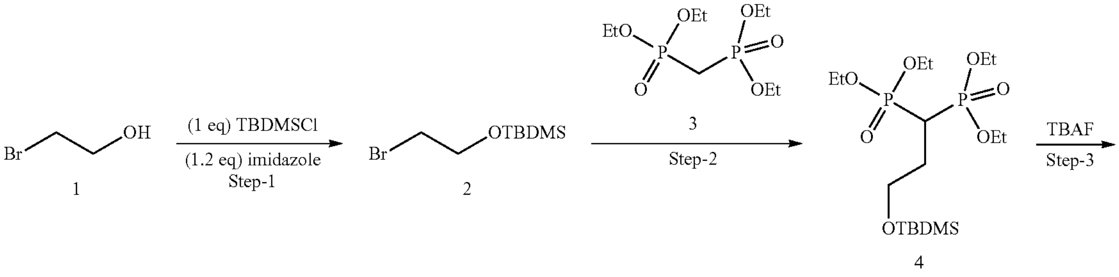

-continued
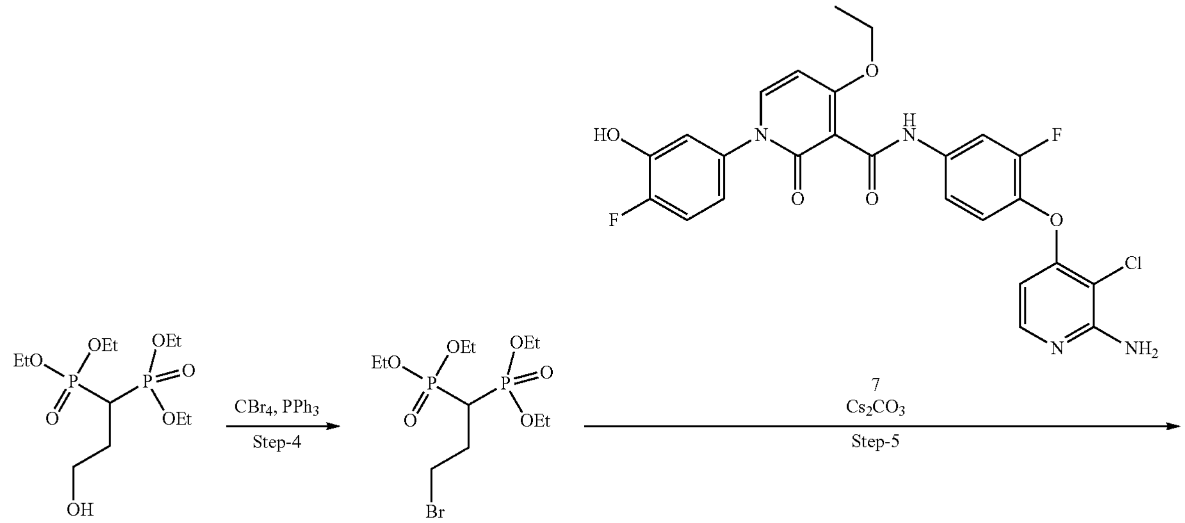
5
6
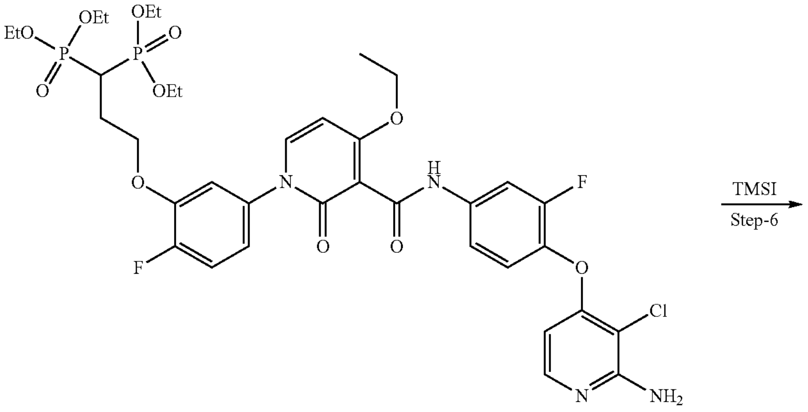
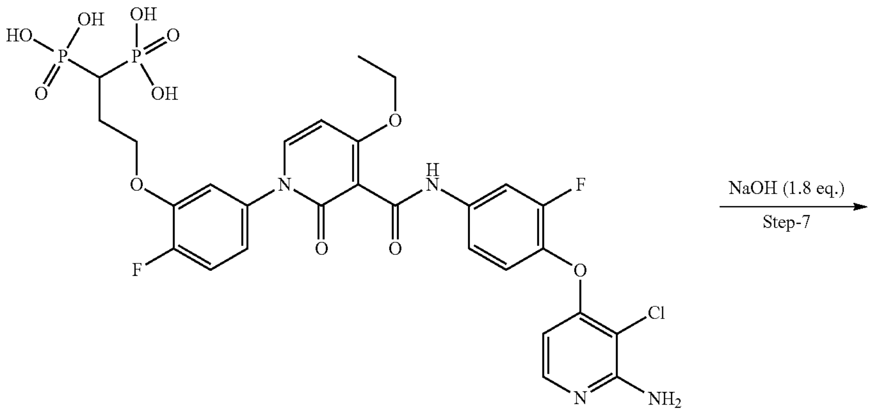

-continued
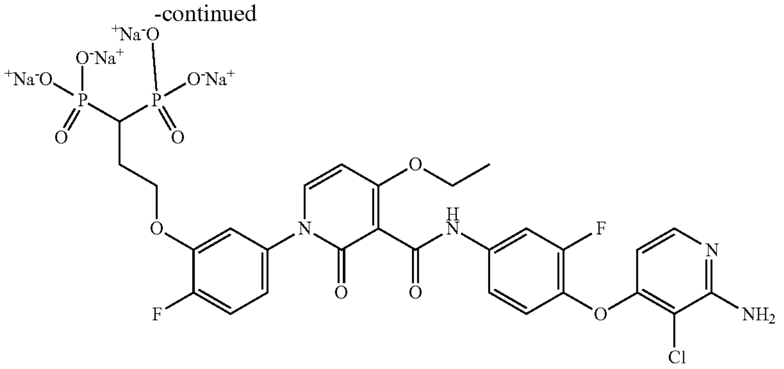
Compound 11
Synthesis of Compound 12
Scheme: Preparation of tetraethyl (3-(5-(3-((4-((2-amino-3-chloropyridin-4-yl)oxy)-3-fluorophenyl) carbamoyl)-4-ethoxy-2-oxopyridin-1 (2H)-yl)-2-fluorophenoxy)propane-1,1-diyl)bis(phosphonate) (Compound 12)
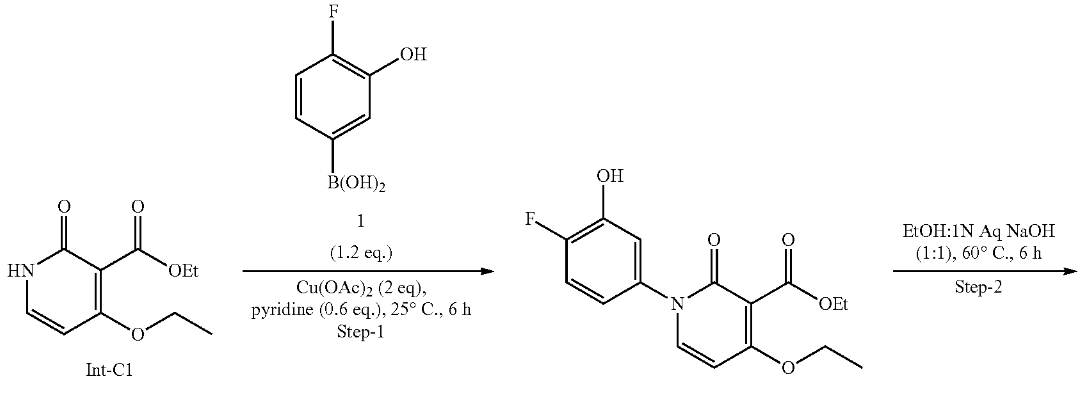
Int-C1
2
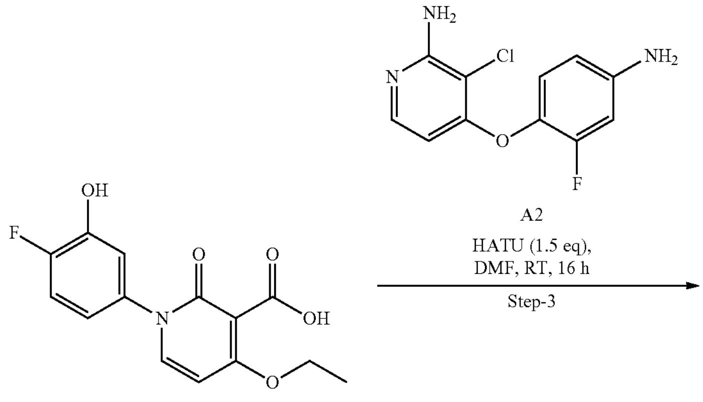
3

-continued
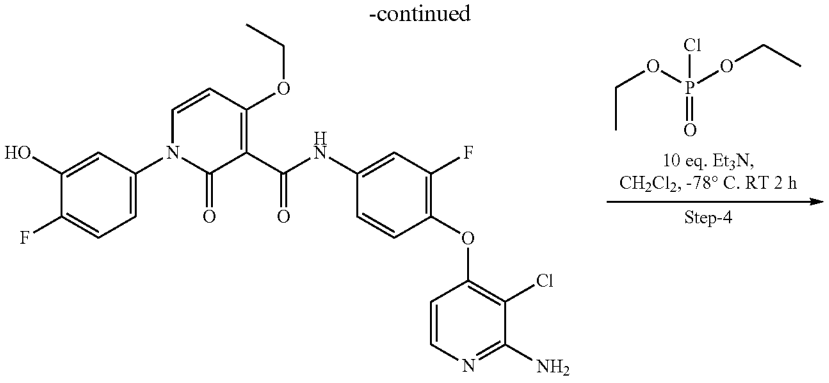
4
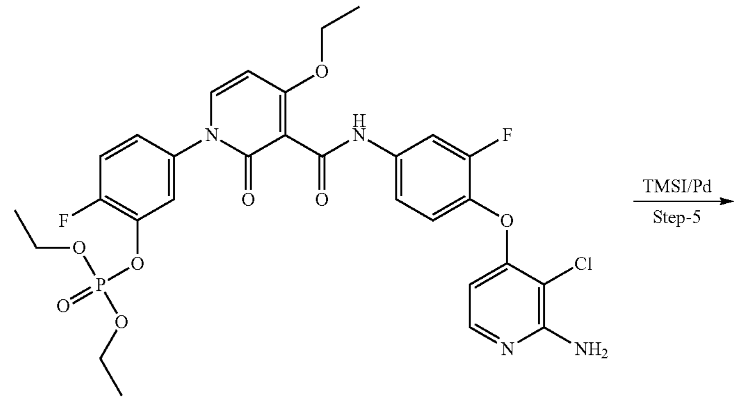
5
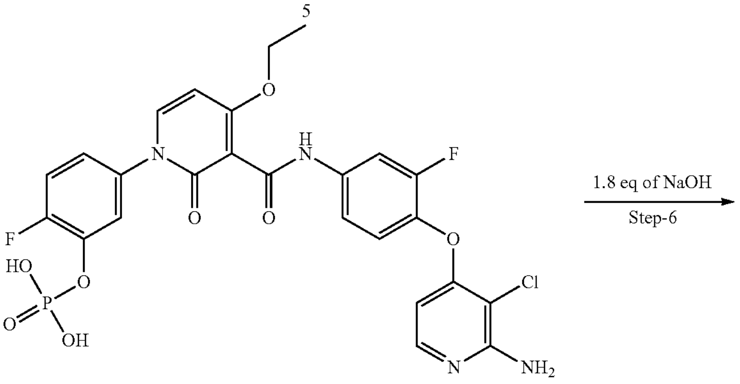
6
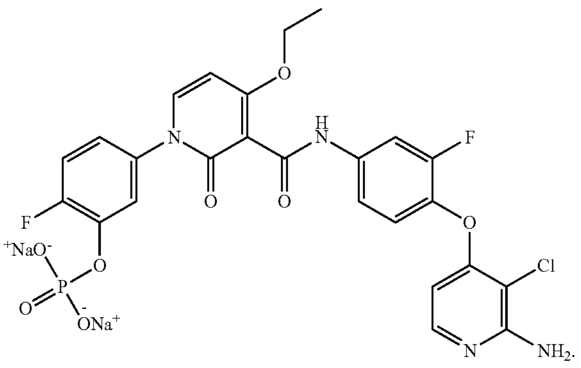
Compound 12

Preparation of ethyl 4-ethoxy-1-(4-fluoro-3-hydroxyphenyl)-2-oxo-1,2-dihydropyridine-3-carboxylate (Cpd-2, Step-1)

2

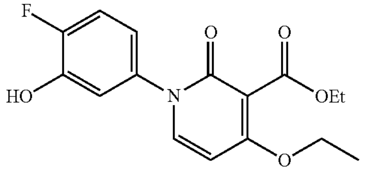

To a stirred solution of Int-C1 (4.0 g, 18.957 mmol) in dichloromethane (40 mL) was added (4-fluoro-3-hydroxyphenyl) boronic acid 1 (3.5 g, 22.748 mmol), Copper (II) acetate (6.9 g, 37.914 mmol) and pyridine (0.91 mL, 11.374 mmol). The reaction mixture was stirred at RT for 6 h in an open flask. The progress of the reaction was monitored by TLC. The reaction mixture was filtered through celite and washed with dichloromethane. The reaction mixture was washed with water (2×80 mL) along washed with brine solution (80 mL), dried over anhydrous $Na_2SO_4$, and evaporated under reduced pressure. The crude material was purified by combi-flash chromatography by using ethyl acetate in hexane to obtain the title Compound-2 (2.9 g, 47% Yield) as pale yellow solid.

Rf: 0.4, Mobile Phase: 50% ethyl acetate in hexane.

$^1$H NMR (400 MHz, DMSO-$d_6$) δ 10.28 (s, 1H), 7.76 (d, J=8.0 Hz, 1H), 7.25 (t, J=9.6 Hz, 1H), 6.92 (d, J=6.4 Hz, 1H), 6.77 (d, J=8.0 Hz, 1H), 6.39 (d, J=8.0 Hz, 1H), 4.20-4.16 (m, 4H), 1.28-1.14 (m, 6H).

LC-MS m/z (M+H): 321.9

Preparation of 4-ethoxy-1-(4-fluoro-3-hydroxyphenyl)-2-oxo-1,2-dihydropyridine-3-carboxylic acid (Cpd-3, Step-2)

3

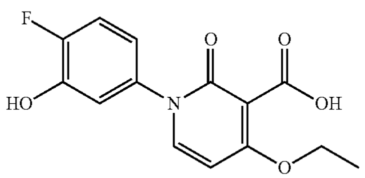

To a stirred solution of Cpd-2 (2.5 g, 7.788 mmol) in ethanol: 1 Naq NaOH (25:25 mL) was added at RT. The reaction mixture was stirred at 60° C. for 6 h. The Progress of the reaction was monitored by TLC. The reaction mixture was washed with ethyl acetate and separates the aqueous layer. The aqueous layer $P^H$ adjusted by using with HCl ($P^H$=1-2), then extracted with ethyl acetate (2×50 mL), and combined organic layer was washed with brine solution (50 mL), dried over anhydrous $Na_2SO_4$, and evaporated under reduced pressure to get the title Compound-3 (1.1 g, 48% Yield) as white solid.

Rf: 0.2, Mobile Phase: 5% methanol in DCM $^1$H NMR (400 MHz, DMSO-$d_6$) δ 13.83 (s, 1H), 10.34 (s, 1H), 7.93 (d, J=7.6 Hz, 1H), 7.28 (t, J=8.8 Hz, 1H), 6.97 (d, J=5.6 Hz, 1H), 6.83 (m, 1H), 6.56 (d, J=8.0 Hz, 1H), 4.27 (q, J=6.4 Hz, 2H), 1.32 (t, J=6.4 Hz, 3H).

LC-MS m/z (M+H): 293

Preparation of N-(4-((2-amino-3-chloropyridin-4-yl)oxy)-3-fluorophenyl)-4-ethoxy-1-(4-fluoro-3-hydroxyphenyl)-2-oxo-1,2-dihydropyridine-3-carboxamide (Cpd-4, Step-3)

4

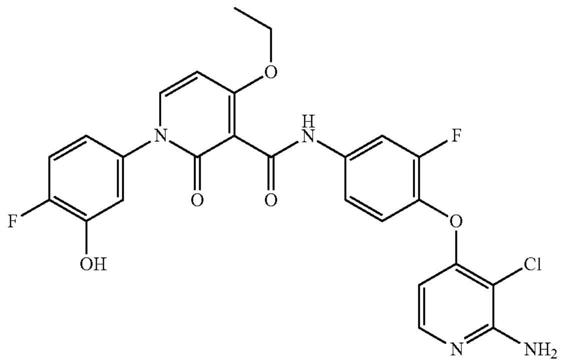

To a stirred solution of Cpd-3 (1 g, 3.412 mmol, 1 eq.) in DMF (5 mL) was added DIPEA (2.6 mL, 10.236 mmol, 3 eq.) and HATU (1.9 g, 5.119 mmol, 1.5 eq). The reaction mixture was stirred at RT for 15 min. Then added Cpd-A2 (1.3 g, 3.412 mmol, 1 eq.) at RT, the reaction mixture was stirred at RT for 16 h. The Progress of the reaction was monitored by TLC. The reaction mixture was diluted with cold water and extracted with ethyl acetate (2×40 mL), and combined organic layer was washed with brine solution (40 mL), dried over anhydrous $Na_2SO_4$, and evaporated under reduced pressure. The crude material was purified by combi-flash chromatography by using methanol in DCM to obtain the title Compound-4 (1.1 g, 61% Yield) as white solid.

Rf: 0.5, Mobile Phase: 5% methanol in DCM.

$^1$H NMR (400 MHz, DMSO-$d_6$) δ 10.54 (s, 1H), 10.38 (s, 1H), 7.90-7.79 (m, 2H), 7.72 (d, J=5.2 Hz, 1H), 7.41 (d, J=8.0 Hz, 1H), 7.31-7.24 (m, 2H), 6.95 (d, J=6.4 Hz, 1H), 6.77 (m, 1H), 6.46 (d, J=8.0 Hz, 1H), 6.40 (s, 2H), 5.92 (d, J=4.8 Hz, 1H) 4.23-4.22 (m, 2H), 1.27 (t, J=6.8 Hz, 3H).

LC-MS m/z (M+H): 528.8

Preparation of 5-(3-((4-((2-amino-3-chloropyridin-4-yl)oxy)-3-fluorophenyl)carbamoyl)-4-ethoxy-2-oxopyridin-1 (2H)-yl)-2-fluorophenyl diethyl phosphate (Cpd-5, Step-4)

5

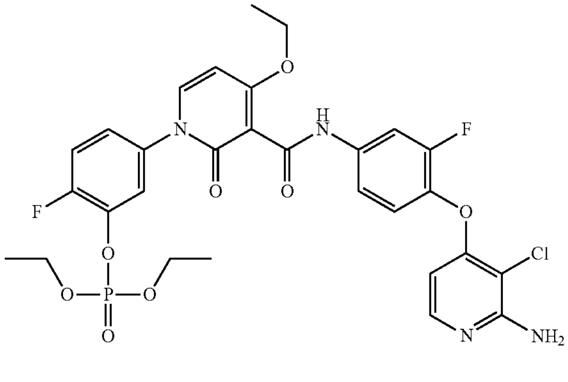

To a stirred solution of Cpd-4 (200 mg, 0.378 mmol) in DCM (5 mL) was cooled to −78° C., then added triethylamine (0.52 mL, 3.787 mmol) under nitrogen atmosphere, the resulting reaction mixture was stirred at −78° C. for 30 min. Then, diethyl chlorophosphate (81 μL 0.567 mmol) was added drop wise to reaction mixture at −78° C. The reaction mixture was stirred at RT for 2 h. The progress of the reaction was monitored by TLC. The reaction mixture was quenched with aq sodium carbonate and extracted with ethyl acetate (3×25 mL), and combined organic layer was washed with brine solution (25 mL), dried over anhydrous $Na_2SO_4$, and evaporated under reduced pressure. The crude compound was purified by Prep-HPLC and pure fractions were lyophilized to get title Compound-5 (150 mg, 60% Yield) as off white solid.

Rf: 0.3, Mobile Phase: 5% methanol in DCM.

$^1$H NMR (400 MHz, DMSO-$d_6$) δ 10.55 (s, 1H), 7.87-7.85 (m, 2H), 7.72 (d, J=5.2 Hz, 1H), 7.58-7.53 (m, 1H), 7.47 (d, J=6.0 Hz, 1H), 7.41 (d, J=8.0 Hz, 1H), 7.31-7.27 (m, 2H), 6.53 (d, 7.6 Hz, 1H), 6.40 (s, 2H), 5.92 (d, J=5.6 Hz, 1H) 4.25-4.16 (m, 6H), 1.32-1.16 (m, 9H).

LC-MS m/z (M+H): 664.92

6

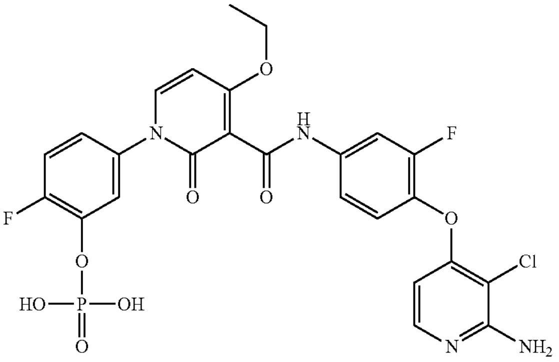

Preparation of 5-(3-((4-((2-amino-3-chloropyridin-4-yl)oxy)-3-fluorophenyl)carbamoyl)-4-ethoxy-2-oxopyridin-1 (2H)-yl)-2-fluorophenyl dihydrogen phosphate (Cpd-6, Step-5)

To a stirred solution of cpd-5 (150 mg, 0.225 mmol) in DCM (6 mL) was cooled 0° C., then added drop wise TMS-I (451.8 mg, 2.259 mmol) in DCM (2 mL) at 0° C. The reaction mixture was stirred at RT for 1 h. The progress of the reaction was monitored by TLC and LCMS. After completion of reaction, the reaction mixture was concentrated under reduced pressure to get crude compound. The crude compound was purified by Prep-HPLC and pure fractions were lyophilized to obtained title Compound-6 (45 mg, 33% Yield) as off white solid.

Rf: 0.1, Mobile Phase: 10% methanol in DCM.

$^1$H NMR (400 MHz, DMSO-$d_6$) δ 10.59 (s, 1H), 7.88-7.80 (m, 2H), 7.72 (d, J=5.2 Hz, 1H), 7.46-7.41 (m, 3H), 7.29 (t, J=8.8 Hz, 1H), 7.16 (m, 1H), 6.50 (d, J=8.0 Hz, 1H), 6.46 (s, 2H), 5.93 (d, J=6.0 Hz, 1H) 4.24-4.21 (m, 2H), 1.27 (t, J=6.8 Hz, 3H).

LC-MS m/z (M+H): 608.5

Preparation of sodium 5-(3-((4-((2-amino-3-chloropyridin-4-yl)oxy)-3-fluorophenyl)carbamoyl)-4-ethoxy-2-oxopyridin-1 (2H)-yl)-2-fluorophenyl phosphate (Compound 12)

TGN-HCl-1071

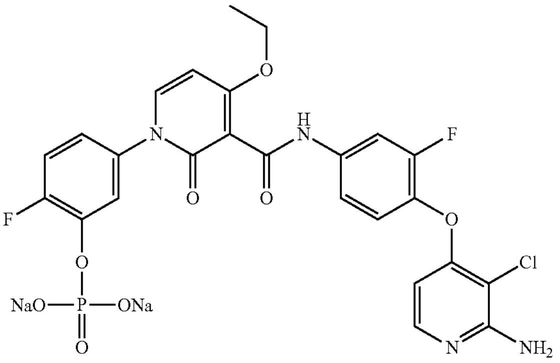

To a stirred solution of Cpd-6 (40 mg, 0.0657 mmol) in DM Water (4 mL) was added drop wise NaOH (4.7 mg, 0.118 mmol) in DM Water (1 mL) at RT. The reaction mixture was stirred at RT for 20 min. The $P^H$ of the reaction mixture was monitored by $P^H$ Paper, after complete addition The $P^H$ was approximately 7-8. Then the reaction mixture was lyophilized to get title compound Compound 12 (25 mg, 59% yield) as off white solid.

$^1$H NMR (400 MHz, $D_2O$) δ 7.86 (d, J=7.6 Hz, 1H), 7.74-7.67 (m, 2H), 7.45 (d, J=5.6 Hz, 1H), 7.34-7.27 (m, 3H), 7.06 (m, 1H), 6.63 (d, J=7.6 Hz, 1H), 6.23 (d, J=5.2 Hz, 1H), 4.32-4.31 (m, 2H), 1.37 (t. J=6.8 Hz, 3H).

LC-MS m/z (M+H): 608.7

Compound 13
Synthetic Scheme for Compound 13
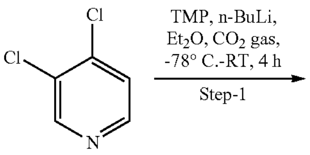
1
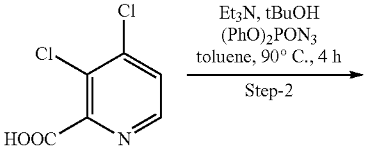
2
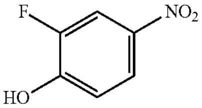
2
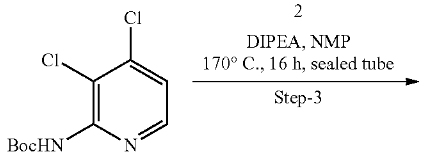
3
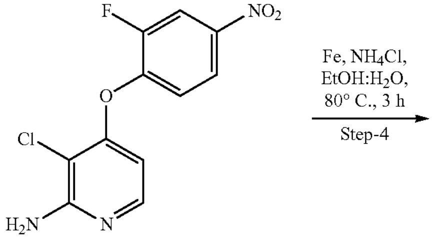
4
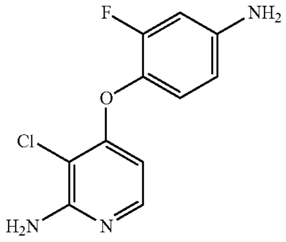
5
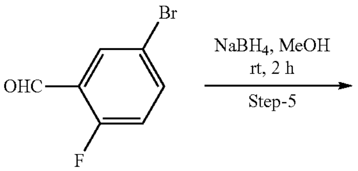
6
-continued
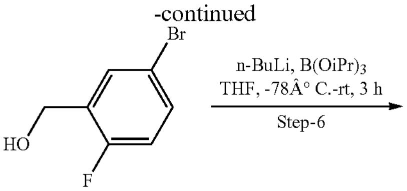
7
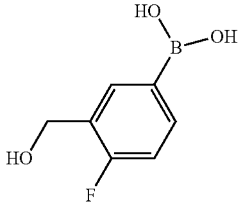
8
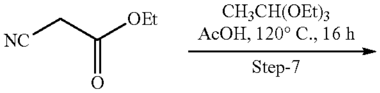
9
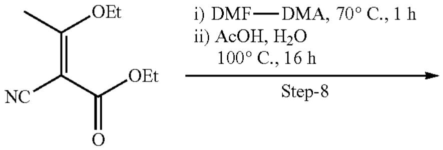
10
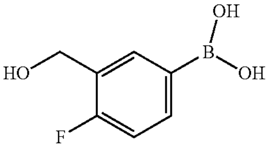
8
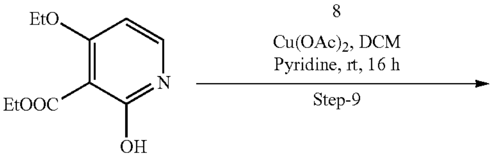
11
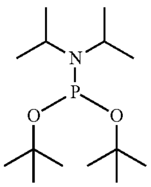
6
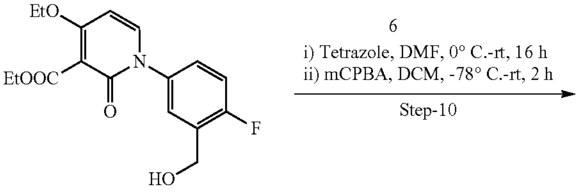
12

-continued
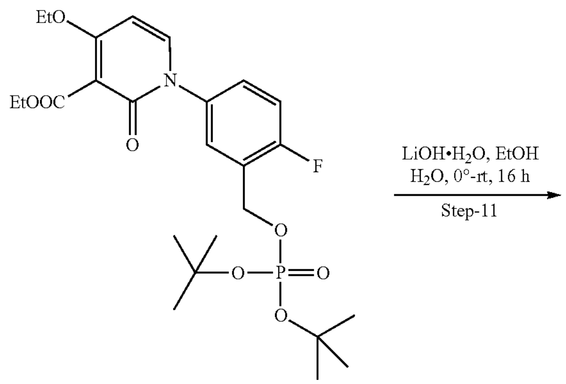
13
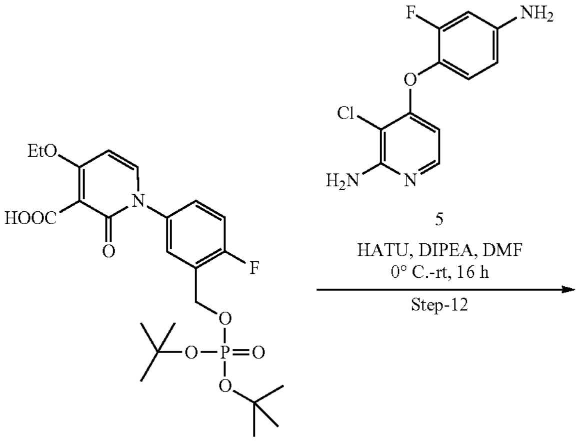
5
14
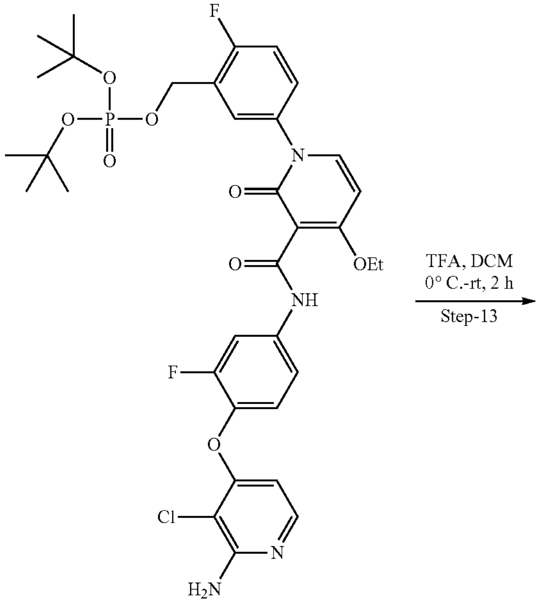
15
-continued
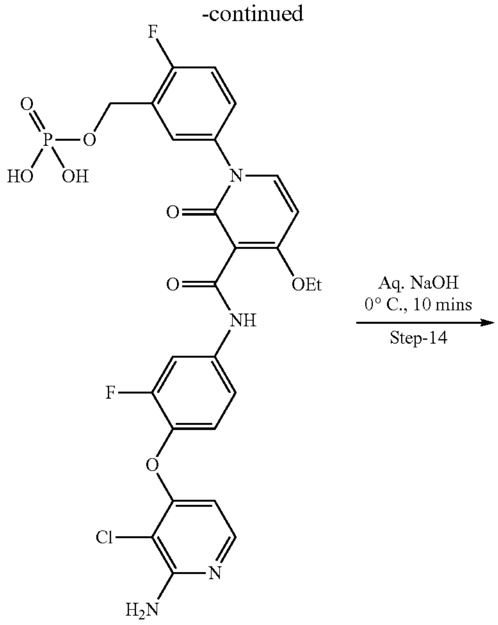
16
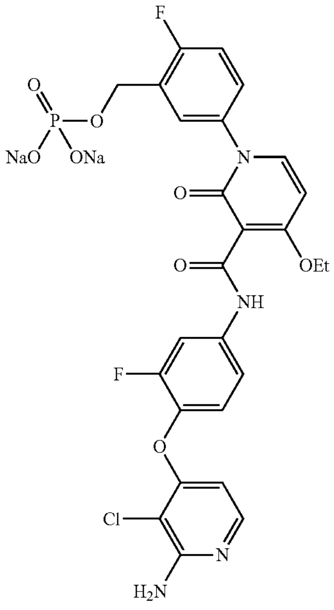
Compound 13
Synthesis of tert-butyl (3,4-dichloropyridin-2-yl)carbamate (3)
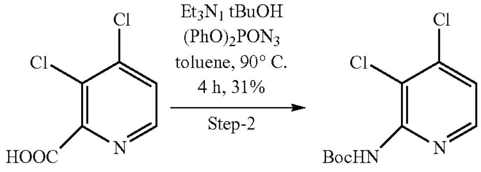
2
3
To a stirred solution of 3,4-dichloropicolinic acid (2) (7 g, 36.45 mmol, 1 eq) in toluene (84 mL) was added TEA (10.2 mL, 72.9 mmol, 2 eq), Diphenylphosphoryl azide (DPPA) (8.6 mL, 40.1 mmol, 1.1 eq) at RT and stirred for 30 min. Later added tert-butanol (7 mL, 72.9 mmol, 2 eq) and Boc anhydride (9.2 mL, 40.1 mmol. 1.1 eq) and the resulting mixture was stirred at 90° C. for 4 h. After completion of reaction by TLC, diluted with EtOAc (100 mL), washed with 10% aqueous $Na_2CO_3$ (3x50 mL), brine solution (40 mL), dried over sodium sulfate and concentrated to provide crude product. The crude was purified by silica gel (60-120 mesh) column chromatography [gradient elution with 10-15% EtOAc: Hexane] to afford tert-butyl (3,4-dichloro-pyridin-2-yl)carbamate (3) (3 g, 31% Yield) as white solid. TLC system: EtOAc/Hexane (30:70), Rf value: ~0.6; LCMS (m/z): 207 [(M−tBu)+H]$^+$. $^1$H NMR (DMSO-$d_6$, 400 MHz) δ 9.64 (s, 1H), 8.30 (d, J=5.2 Hz, 1H), 7.57 (d, J=5.2 Hz, 1H) 1.45 (s, 9H).

Synthesis of 3-chloro-4-(2-fluoro-4-nitrophenoxy) pyridin-2-amine (4)

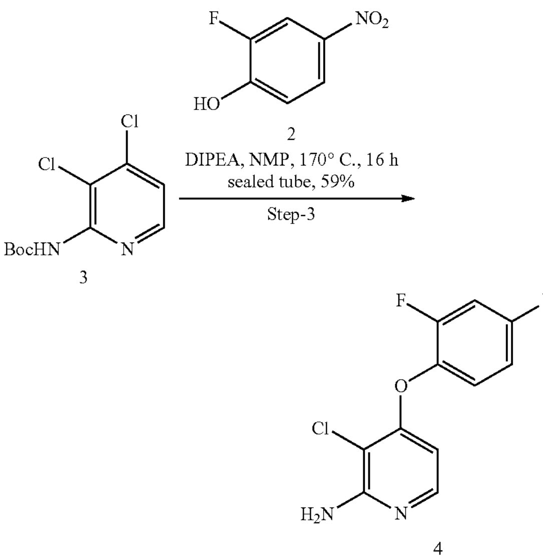

2 3 4

A solution of 2-fluoro-4-nitrophenol (1.97 g, 12.6 mmol, 1.1 eq) in NMP (6 mL) was placed in glass pressure vessel and added DIPEA (2.97 mL, 17.1 mmol, 1.5 eq) at RT, stirred for 30 min. Later added tert-butyl (3,4-dichloropyridin-2-yl)carbamate (3) (3 g, 11.4 mmol, 1 eq) and heated at 170° C. for 16 h. After completion of reaction by TLC, diluted with water and extracted with EtOAc (2x50 mL). The combined organic layer was washed with water (50 mL), saturated aq. $NaHCO_3$ solution (50 mL), brine solution (40 mL), dried over anhydrous sodium sulfate and concentrated under reduced pressure to get crude compound. Crude was purified by silica gel (60-120 mesh) column chromatography [gradient elution with 0-1% of MeOH in DCM] to afford 3-chloro-4-(2-fluoro-4-nitrophenoxy)pyridin-2-amine (4) (1.9 g, 59% Yield) as yellow color solid. TLC system: EtOAc/Hexane (50:50), Rf value: ~0.3; LCMS (m/z): 284 (M+H)$^+$. $^1$H NMR (400 MHz, DMSO-$d_6$) δ 8.40 (dd, J=10.8 Hz, 2.8 Hz, 1H), 8.15-8.12 (m, 1H), 7.88 (d, J=5.6 Hz, 1H), 7.41 (t, J=8.4 Hz, 1H), 6.60 (s, 2H), 6.29 (d, J=5.6 Hz, 1H).

Synthesis of 4-(4-amino-2-fluorophenoxy)-3-chloro-pyridin-2-amine (5)

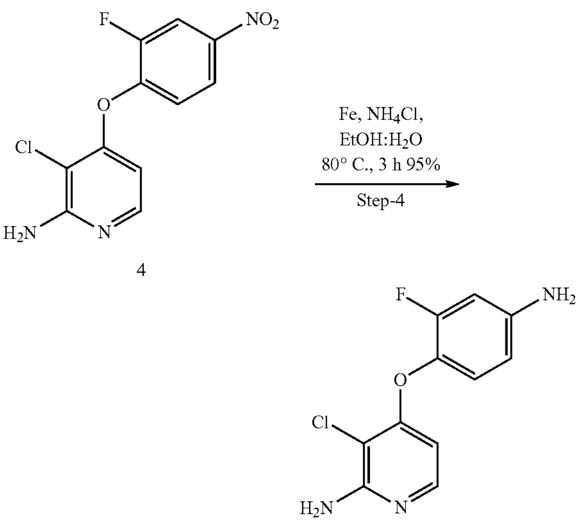

4 5

To a stirred solution of 3-chloro-4-(2-fluoro-4-nitrophenoxy)pyridin-2-amine (4) (1.9 g, 6.6 mmol, 1 eq) in EtOH/$H_2O$ (2:1) (30 mL) was added $NH_4Cl$ (1.76 g, 33 mmol, 5 eq), Fe powder (1.8 g, 33 mmol, 5 eq) was added portion wise at room temperature. The reaction mixture was stirred at 80° C. for 3 h. After completion of reaction by TLC, the reaction mixture was filtered through celite bed and washed with EtOAc (60 mL). The filtrate was washed with water (20 mL), brine solution (20 mL), dried over sodium sulfate and concentrated to provide crude product which was triturated with diethyl ether to afford 4-(4-amino-2-fluorophenoxy)-3-chloropyridin-2-amine (5) as brown solid (1.5 g, yield: 95%). TLC system EtOAc (100), Rf value: ~0.3: LCMS (m/z): 254.1 (M+H)$^+$: $^1$H NMR (400 MHz, DMSO-$d_6$) δ 7.71 (d, J=6.0 Hz, 1H), 6.96 (t, J=8.8 Hz, 1H), 6.49 (dd, J=13.2 Hz, 2.8 Hz, 1H), 6.41-6.39 (m, 1H), 6.31 (s, 2H), 5.84 (d, J=5.6 Hz, 1H), 5.45 (s, 2H).

Synthesis of (5-bromo-2-fluorophenyl) methanol (7)

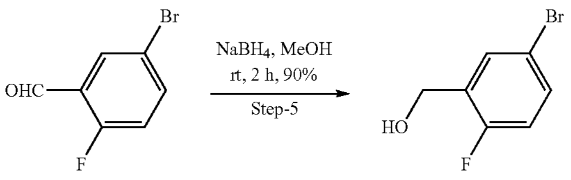

6 7

To a stirred solution of 5-bromo-2-fluorobenzaldehyde (6) (20 g, 98.5 mmol, 1.0 eq) in methanol (200 mL) at 0° C. was added $NaBH_4$ (4.49 g, 118.2 mmol, 1.2 eq). Reaction mixture was stirred at room temperature for 2 h. After completion of reaction by TLC, reaction mixture was quenched with ice cold water and extracted with EtOAc (2x200 mL). The combined organic layer was washed with water (80 mL), brine solution (80 mL), dried over sodium sulfate and concentrated to afford (5-bromo-2-fluorophenyl) methanol (7) as liquid (18 g, yield: 90%). TLC system EtOAc: Hexane: (30:70), Rf value: ~0.3; $^1$HNMR (400 MHz, $CDCl_3$) δ 7.59 (dd, J=6.4 Hz, 2.8 Hz, 1H), 7.40-7.36 (m, 1H), 6.96-6.91 (m, 1H), 4.74 (d, J=6.0 Hz, 2H), 1.85 (t, J=6.0 Hz, 1H).

Synthesis of (4-fluoro-3-(hydroxymethyl)phenyl) boronic acid (8)

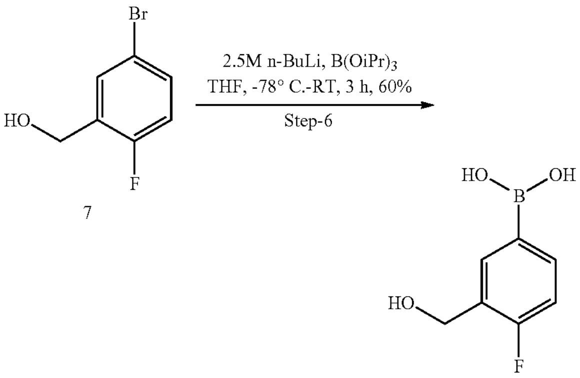

7

8

To a stirred solution of (5-bromo-2-fluorophenyl) methanol (7) (18 g, 87.8 mmol, 1.0 eq) in THF (180 mL) cooled to −78° C. was added n-BuLi (2.5 M in hexane) (77 mL, 193.16 mmol, 2.2 eq) and stirred for 40 min. Later at −78° C., added Tri isopropyl Borate (44.83 mL, 193.16 mmol, 2.2 eq) under nitrogen atmosphere. The resulting mixture was allowed to room temperature and stirred for 3 h. After completion of reaction by TLC, reaction mixture was quenched with 2N HCl and stirred for 10 mins, diluted with water, extracted with EtOAc (2×200 mL). The combined organic layer was washed with water (80 mL), brine solution (80 mL), dried over sodium sulfate and concentrated under reduced pressure. The obtained crude was purified by silica gel (60-120 mesh) column chromatography [gradient elution with 30-100% of EtOAc in Hexane] to afford (4-fluoro-3-(hydroxymethyl)phenyl) boronic acid (8) as an off white solid (9 g, yield: 60%). TLC system: EtOAc (100), Rf value: ~0.4: 1HNMR (400 MHz, DMSO-$d_6$) δ 8.03 (s, 2H), 7.91 (dd, J=8.4 Hz, 1.6 Hz, 1H), 7.74-7.70 (m, 1H), 7.10-7.06 (m, 1H), 5.19 (t, J=5.6 Hz, 1H), 4.53 (t, J=5.6 Hz, 2H).

Synthesis of ethyl 4-ethoxy-1-(4-fluoro-3-(hydroxymethyl)phenyl)-2-oxo-1,2-dihydropyridine-3-carboxylate (12)

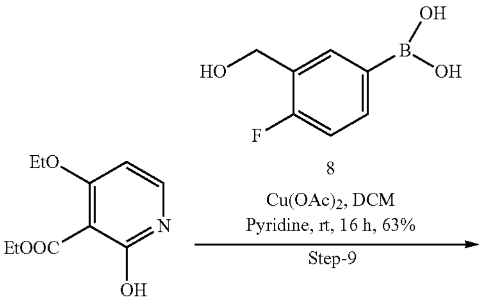

8

11

-continued

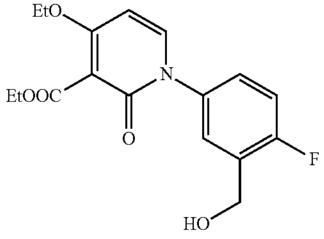

12

To a stirred solution of ethyl 4-ethoxy-2-hydroxynicotinate (11) (3 g, 14.1 mmol, 1.0 eq) in DCM (60 mL) was added (4-fluoro-3-(hydroxymethyl)phenyl) boronic acid (8) (7.1 g, 42.4 mmol, 3 eq), $Cu(OAc)_2$ (5.1 g, 28.2 mmol, 2 eq), Pyridine (7.1 g, 56.4 mmol, 4 eq) and stirred for 30 min The resulting mixture was stirred for 16 h at room temperature. After completion of reaction by TLC, reaction mixture was diluted with DCM (100 mL) and washed with water (80 mL), brine solution (50 mL), dried over sodium sulfate and concentrated under reduced pressure to provide crude material. The obtained crude was purified by silica gel (60-120 mesh) column chromatography [gradient elution with 5-10% MeOH in DCM] to afford ethyl 4-ethoxy-1-(4-fluoro-3-(hydroxymethyl)phenyl)-2-oxo-1,2-dihydropyridine-3-carboxylate (12) as white solid (3 g, yield: 63%). TLC system: MeOH/DCM (10:90), Rf value: ~0.5; $^1$HNMR (400 MHz, DMSO-$d_6$) δ 7.79 (d, J=8.0 Hz, 1H), 7.43 (dd, J=6.4 Hz, 2.0 Hz, 1H), 7.32-7.26 (m, 2H), 6.43 (d, J=8.0 Hz, 1H), 5.41 (t, J=6.0 Hz, 1H), 4.58 (d, J=6.0 Hz, 2H), 4.25-4.18 (m, 4H), 1.29 (t, J=7.2 Hz, 3H), 1.22 (t, J=7.2 Hz, 3H).

Synthesis of ethyl 1-(3-(((di-tert-butoxyphosphoryl)oxy)methyl)-4-fluorophenyl)-4-ethoxy-2-oxo-1,2-dihydropyridine-3-carboxylate (13)

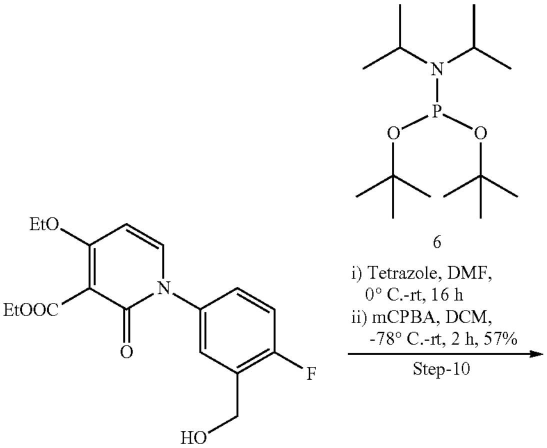

6

12

-continued

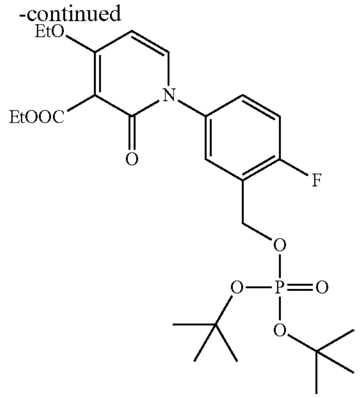

13

-continued

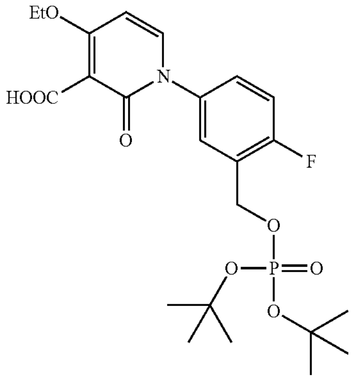

14

A solution of ethyl 4-ethoxy-1-(4-fluoro-3-(hydroxymethyl)phenyl)-2-oxo-1,2-dihydropyridine-3-carboxylate (12) (200 mg, 0.59 mmol, 1.0 eq) in DMF (4 mL) cooled to 0° C. and added 5-methyl tetrazole (396 mg, 4.72 mmol, 8.0 eq), di-tert-butyl diisopropylphosphoramidite (818 mg, 2.95 mmol, 5.0 eq). The resulting mixture was stirred at room temperature for 16 h. After completion of reaction by TLC, reaction mixture was quenched with ice-cold water and extracted with EtOAc (2×50 mL). The combined organic layer was washed with water (30 mL), brine solution (20 mL), dried over anhydrous sodium sulfate and concentrated under reduced pressure to provide crude. [The above reaction was repeated simulataneously on another 4×200 mg batches] The combined 5 batches crude was dissolved in DCM (20 mL) and cooled to −78° C. and added mCPBA (60%) (1.1 g, 6.3 mmol, 2.1 eq) and stirred at room temperature for 2 h. After completion of reaction by TLC, reaction mixture was diluted with DCM (80 mL) and washed with saturated $NaHCO_3$ (30 mL) solution, water (30 mL), brine solution (20 mL), dried over sodium sulfate and concentrated under reduced pressure to get crude. The obtained material was purified by silica gel (60-120 mesh) column chromatography [eluted with 3% MeOH in DCM] to afford ethyl 1-(3-(((di-tert-butoxyphosphoryl)oxy)methyl)-4-fluorophenyl)-4-ethoxy-2-oxo-1,2-dihydropyridine-3-carboxylate (13) as pale yellow liquid (900 mg, yield: 57%). TLC system: EtOAc (100), Rr value: ~0.5; LCMS (m/z): 416.2 $(M-2tBu+H)^+$.

Synthesis of 1-(3-(((di-tert-butoxyphosphoryl)oxy)methyl)-4-fluorophenyl)-4-ethoxy-2-oxo-1,2-dihydropyridine-3-carboxylic acid (14)

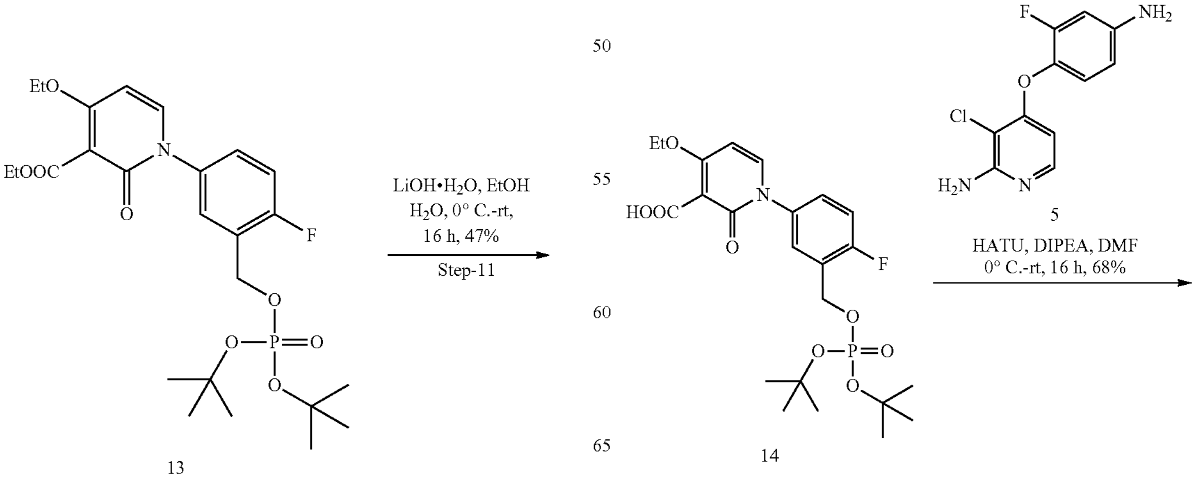

13 14 5

To a stirred solution of ethyl 1-(3-(((di-tert-butoxyphosphoryl)oxy)methyl)-4-fluorophenyl)-4-ethoxy-2-oxo-1,2-dihydropyridine-3-carboxylate (13) (900 mg, 1.70 mmol, 1.0 eq) in EtOH:$H_2O$ (2:1) (15 mL) at 0° C. was added LiOH·$H_2O$ (348 mg, 8.50 mmol, 5 eq) and the resulting mixture was stirred at room temperature for 16 h. After completion of reaction by TLC, reaction mixture was diluted with water, acidified with 1M $H_3PO_4$ solution to pH-6 and extracted with EtOAc (2×50 mL). The combined organic layer was washed with water (30 mL), brine solution (30 mL), dried over anhydrous sodium sulfate and concentrated to afford 1-(3-(((di-tert-butoxyphosphoryl)oxy)methyl)-4-fluorophenyl)-4-ethoxy-2-oxo-1,2-dihydropyridine-3-carboxylic acid (14) as gummy liquid (400 mg, yield: 47%). TLC system: MeOH: DCM: (10:90), Rf value: ~0.4, LCMS (m/z): 500.3 (M+H)+

Synthesis of 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl di-tert-butyl phosphate (15)

-continued

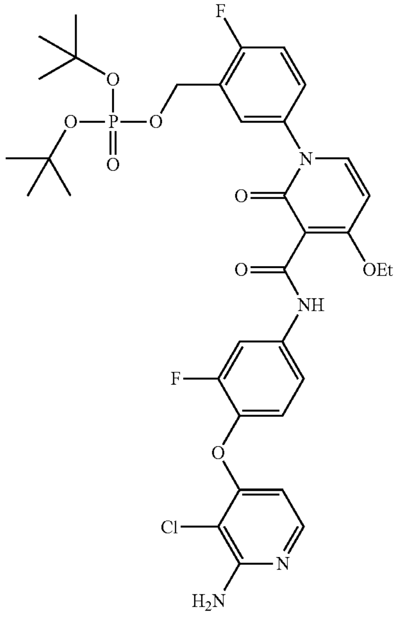

15

To a solution of 1-(3-(((di-tert-butoxyphosphoryl)oxy) methyl)-4-fluorophenyl)-4-ethoxy-2-oxo-1,2-dihydropyridine-3-carboxylic acid (14) (400 mg, 0.80 mmol, 1.0 eq) in DMF (4 mL) at 0° C. was added 4-(4-amino-2-fluorophenoxy)-3-chloropyridin-2-amine (5) (202 mg, 0.80 mmol, 1.0 eq), HATU (456 mg, 1.2 mmol, 1.5 eq), DIPEA (0.28 mL, 1.60 mmol, 2 eq). The reaction mixture was stirred at room temperature for 16 h. After completion of reaction by TLC, reaction mixture was diluted with ice cold water, resulted in precipitation and was filtered, dried under vacuum to afford residue. The obtained crude was purified by triturations with diethyl ether to afford 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl di-tert-butyl phosphate (15) as brown solid (0.4 g, 68%). TLC system: MeOH/DCM (5:95) (2 times elution), Rr value: ~0.4; LCMS (m/z): 679.4 $(M-tBu+H)^+$; 1HNMR (400 MHz, DMSO-$d_6$) δ 10.55 (s, 1H), 7.92-7.81 (m, 2H), 7.73 (d, J=6.0 Hz, 1H), 7.54-7.44 (m, 4H) 7.30 (t, J=8.8 Hz, 1H), 6.53 (d, J=8.0 Hz, 1H), 6.40 (s, 2H), 5.93 (d, J=5.6 Hz, 1H), 5.00 (d, J=7.2 Hz, 2H), 4.26 (q, J=6.8 Hz, 2H), 1.40 (s, 18H), 1.30 (t, J=6.8 Hz, 3H). $^{31}P$ NMR: δ −10.33.

Synthesis of 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl dihydrogen phosphate (16)

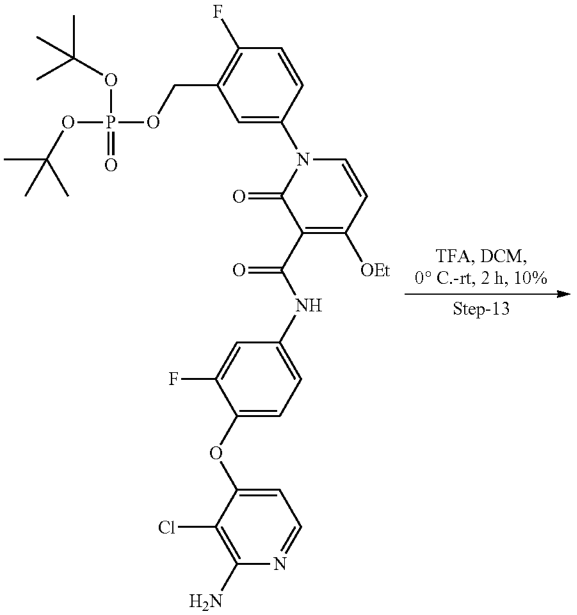

15

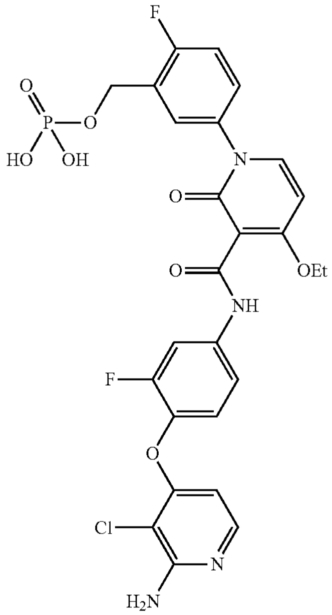

16

To a stirred solution of 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl di-tert-butyl phosphate (15) (0.4 g, 1.47 mmol, 1.0 eq) in DCM (2 mL) at 0° C. in DCM (0.2 mL), was added 10% TFA in DCM (2 mL) and allowed to reach room temperature, stirred for 2 h. After completion of reaction by TLC, distilled the volatiles to afford crude. The obtained crude was purified by Prep HPLC [0.1% TFA in $H_2O$ as buffer] to afford 5-(3-((4-((2-amino-3-chloropyridin-4-yl)oxy)-3-fluorophenyl)carbamoyl)-4- ethoxy-2-oxopyridin-1 (2H)-yl)-2-fluorobenzyl dihydrogen phosphate (16) (30 mg, yield: 10%). TLC system: MeOH/DCM (10:90), Rf value: ~0.01; LCMS (m/z): 623.3 $(M+H)^+$; $^1$HNMR (400 MHz, DMSO-$d_6$) δ 10.60 (s, 1H), 7.90 (dd, J=10.8 Hz, 2.4 Hz, 1H), 7.84 (d, J=7.6 Hz, 1H), 7.79 (d, J=6.0 Hz, 1H) 7.51-7.43 (m, 4H), 7.39-7.32 (m, 1H), 7.08-6.95 (br, 2H), 6.53 (d, J=8.0 Hz, 1H), 6.10 (d, J=6.0 Hz, 1H), 4.99 (d, J=7.2 Hz, 2H), 4.24 (q, J=7.2 Hz, 2H), 1.29 (t, J=7.2 Hz, 3H); $^{31}$P NMR: δ −1.27.

Synthesis of Sodium 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl phosphate (Compound 13)

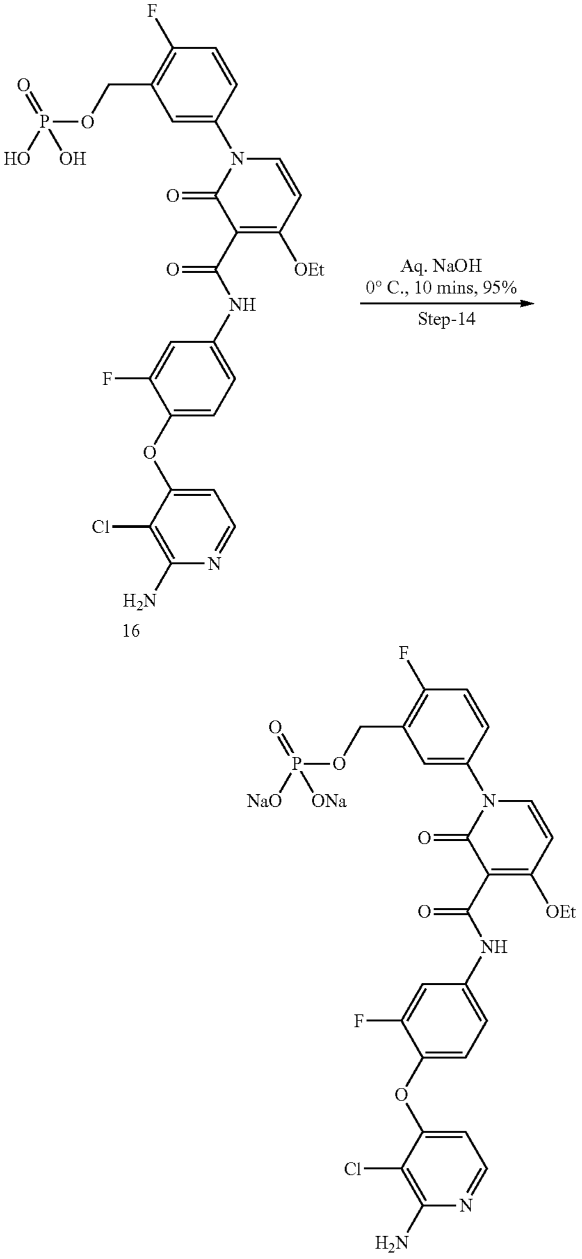

16

Compound 13

To a stirred solution of 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl dihydrogen phosphate (16) (20 mg, 0.048 mmol, 1.0 eq) cooled to 0° C. and added aq. NaOH (3.85 mg, 0.096 mmol, 2.0 eq) stirred for 10 mins at 0° C. and kept under lyophilization to afford sodium 5-(3-((4-((2-amino-3-chloropyridin-4-yl)oxy)-3-fluorophenyl)carbamoyl)-4-ethoxy-2-oxopyridin-1 (2H)-yl)-2-fluorobenzyl phosphate (Compound 13) as an off white solid (20 mg, yield: 95%). LCMS (m/z): 623.3 $(M-2Na+H)^+$: $^1$HNMR (400 MHz, DMSO-$d_6$) δ 10.77 (s, 1H), 7.90 (dd, J=13.2 Hz, 2.0 Hz, 1H), 7.79 (d, J=8.0 Hz, 1H), 7.73 (d, J=5.6 Hz, 1H), 7.56 (d, J=4.8 Hz, 1H) 7.47 (d, J=9.2 Hz, 1H), 7.31-7.25 (m, 3H), 6.48 (d, J=7.6 Hz, 1H), 6.39 (s, 2H), 5.93 (d, J=5.6 Hz, 1H), 4.78 (d, J=7.6 Hz, 2H), 4.23 (q, J=7.2 Hz, 2H), 1.28 (t, J=7.2 Hz, 3H). $^{31}$P NMR: δ −0.12.

EXAMPLES OF THE INVENTION

Example 1: Ron Tyrosine Kinase Inhibition Assay

Experimental: Biology

Ron Tyrosine Kinase Inhibition Assay Protocol:

Compounds were tested in 10 dose $IC_{50}$ mode with 3-fold serial dilution starting at 100 μM. Control compound, Staurosporine, was tested in 10 dose $IC_{50}$ mode with 4 fold serial dilution starting at 20 μM. Reactions were carried out at 10 μM ATP. Data pages include raw data, % Enzyme activity (relative to DMSO controls) and curve fits. Curve fits were performed where the enzyme activities at the highest concentration of compounds were less than 65%.

$IC_{50}$ Calculation $IC_{50}$ values may be determined using GraphPad Prism 5 software. The data may be entered as an X-Y plot into the software as percent inhibition for each concentration of the drug. The concentration values of the drug may be log transformed and the nonlinear regression may be carried out using the "sigmoidal dose-response (variable slope)" option within the GraphPad software to model the data and calculate $IC_{50}$ values. The $IC_{50}$ values reported are the concentration of drug at which 50% inhibition was reached.

Compound Activity

The ability of representative disclosed compounds to modulate various biochemical and cellular activities may be determined using the assays described above. The results are shown in the Table below.

TABLE 2

| | Compound $IC_{50}$ (nM) | | |
|---|---|---|---|
| Kinases | Compound A | Compound 1 | Staurosporine |
| RON/MST1R | 17.22 | 13390.00 | 218.10 |

Example 2: Kinase ADP-Glo Inhibition Assay

Experimental Materials

Assay Buffer 40 mM Tris-HCl pH7.5, 20 mM $MgCl_2$, 0.1 mg/mL BSA

RON Kinase Enzyme System (Promega #: V3921)

Axltide Substrate

RON Kinase Enzyme.

ADP-Glo™ Assay (Promega #: V9101)
- ATP, 10 mM
- ADP-Glo™ Reagent
- Kinase Detection Reagent 384-well white assay plates

Experimental Methods

A ten point serial dilution of compound was prepared at 5× concentration in assay buffer with the final assay concentrations starting at 30 μM, 10 μM, 3 μM, 1 μM . . . 0 μM. Enzyme, substrate, and ATP were used at 25 ng, 200 ng and 25 μM, respectively. The assay plate was set up by mixing the components in a total reaction volume of 10 μL per well. The plate was centrifuged gently for 10 seconds and incubated at room temperature (RT) for 60 minutes in the dark. The ADP-Glo Reagent and kinase detection reagent were added and incubated as recommended. The reaction was quantified by measuring luminescence on the Perkin Elmer Envision plate reader. Data was analyzed using Graphpad Prism 7 software.

TABLE 3

| Inhibitor | $IC_{50}$ (μM) |
|---|---|
| Compound 9 | 33.82 |
| Compound 1 | 13.40 |
| Compound 10 | 0.547 |
| Compound 11 | 1.274 |
| Compound 12 | 0.058 |
| Compound 13 | 2.427 |
| Compound 14 | TBD |
| Compound 15 | TBD |
| BMS-777607 | 0.018 |

FIG. 1 describes the results of this experiment for BMS-777607 (a reference compound), Compound 10 and Compound 12.

Figure 2:
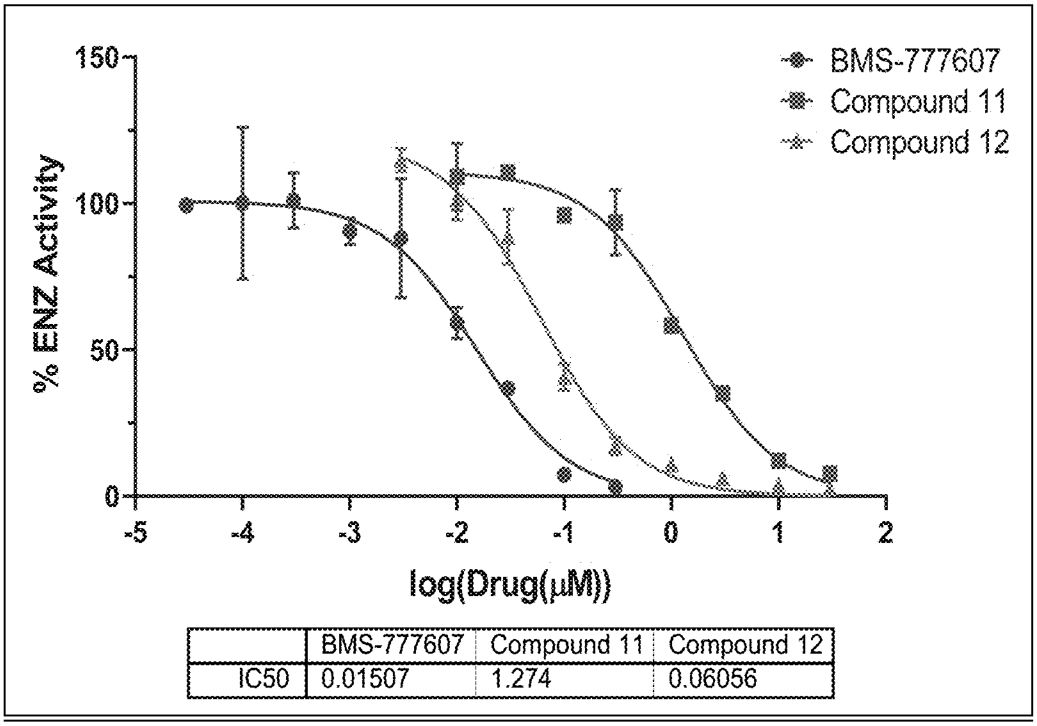
FIG. 2 is a RON kinase inhibition chart for BMS-777607, Compound 11 and Compound 12.

FIG. 2 describes the results of this experiment for BMS-777607, Compound 11 and Compound 12.

Figure 3:
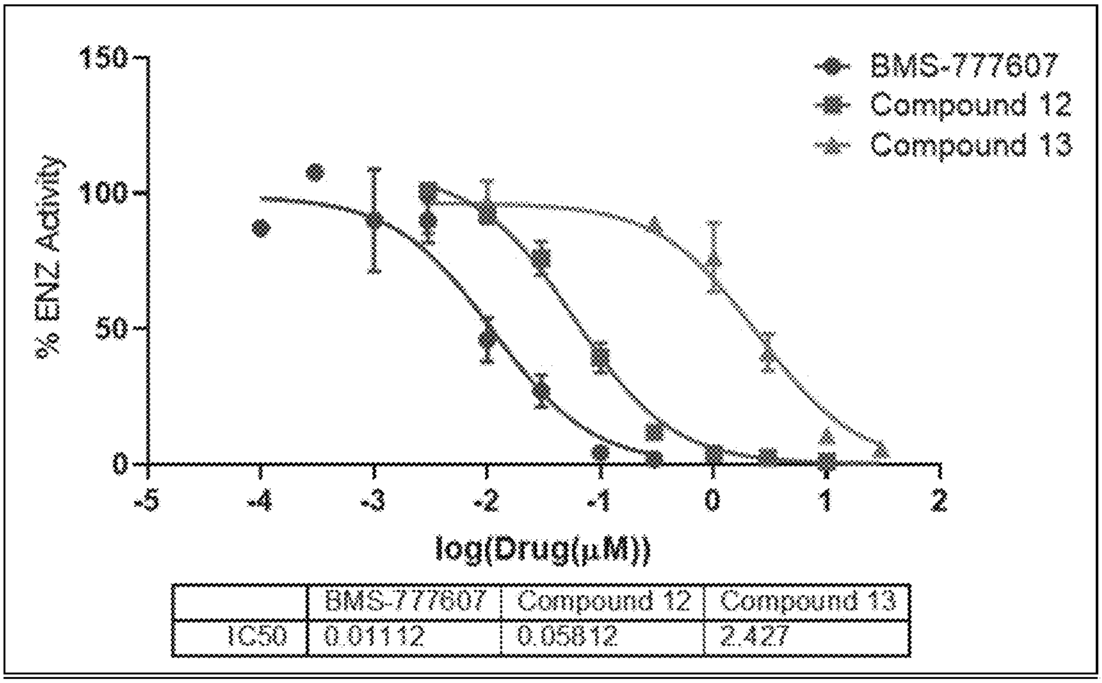
FIG. 3 is a RON kinase inhibition chart for BMS-777607, Compound 12 and Compound 13.

FIG. 3 describes the results of this experiment for BMS-777607, Compound 12 and Compound 13.

Example 3: Cell Viability Assay

Materials
- Breast Cell Lines (Treated according to ATCC guidelines)
- Cell Titer Glo (Promega Cat #G7572)
- DMSO
- 96-well White Tissue Culture Treated Plates (Perkin Elmer Cat #60005680)

Experimental Methods

Cells were seeded in a white 96-well tissue culture treated plate at a density of 1500 cells in 90 μL of media per well and allowed to settle overnight. A ten-point serial dilution of drugs was prepared at 10× concentration in media with the final assay concentrations starting at 30 μM, 10 μM, 3 μM, 1 μM, 0.3 μM . . . 0 μM. A dilution of DMSO was included as a control. The assay was set up by adding 10 μL of the corresponding drug to each well in duplicate, followed by a 72 hour incubation at 37 C, 5% $CO_2$. Cell viability was quantified by adding 90 μL of Cell Titer Glo to each well and incubating at room temperature for 10 minutes. The reaction was quantified by measuring luminescence using the Envision Plate Reader. Data was analyzed using Graphpad Prism 7 software.

Example 4: Pharmacokinetic (PK) Study of Phosphate Conjugates of BMS-777607 in Male Swiss Albino Mice

Experimental Objective

The objective of this study was to determine if phosphate conjugates of BMS-777607 accumulate in bone following a single intravenous (2 mg/kg) bolus administration into male Swiss Albino Mice. For extended time points (>24 hrs), BID dosing was done 8 hr apart. The phosphate conjugates Compound 10 and Compound 12 along with parent BMS-777607 were tested.

Experimental Methods

The study was performed using sparse design to obtain composite profile (n=3/time point) as summarized in the table 1. Blood and whole bone with marrow were collected at predetermined time points. At each time point, about 120 μL of blood was collected by retro-orbital sinus puncture into a labeled microfuge tube containing 200 mM K2EDTA solution (20 μL per mL of blood). The blood samples were processed within 30 minutes to obtain the plasma samples. At respective time points, blood samples were collected and animals were euthanized to harvest whole femur bone (bone with marrow). All plasma and bone with marrow samples were stored at −80° C.

Table 4 below demonstrates a sample PK study design

TABLE 4

Study design, blood and bone collection schedule

| Mouse | Time Points (h) | | | | | | | | | |
|---|---|---|---|---|---|---|---|---|---|---|
| No. | 0.083 | 0.25 | 0.5 | 1 | 2 | 4 | 6 | 24 | 72 | 120 |
| 1 | X | | | | X[a] | | | | | |
| 2 | X | | | | | | | | | |
| 3 | X | | | | | | | | | |
| 4 | | X | | | | X[a] | | | | |
| 5 | | X | | | | | | | | |
| 6 | | X | | | | | | | | |
| 7 | | | X | | | | X | | | X[b] |
| 8 | | | X | | | | X | | | |
| 9 | | | X | | | | X | | | |
| 10 | | | | X | | | | X[a] | | |
| 11 | | | | X | | | | | | |
| 12 | | | | X | | | | | | |
| 13 | | | | X[a] | | | | | | |
| 14 | | | | | | | | | | |
| 15 | | | | | | | | | | |
| 16 | | | | | | | | | X[b] | |
| 17 | | | | | | | | | | |
| 18 | | | | | | | | | | |

[a]Blood and whole bone with marrow was collected from each animal;
[b]Animals were dosed twice daily (8 hr apart) and blood and bone with marrow was collected from each animal The plasma and bone with bone marrow homogenate samples were analyzed using a fit-for purpose LC-MS/MS method with a lower limit of quantification (LLOQ) of 1.00 ng/mL (plasma) and 11.0 ng/g (bone). In some instances, bone marrow was separated from bone and analyzed independently. The pharmacokinetic parameters of the drugs were calculated using the non-compartmental analysis tool of validated Phoenix® WinNonlin® software (version 8.0).

Experimental Results

Results indicated that both Compound 10 and parent BMS-777607 were accumulated in the bone. The bone to plasma ratios ($AUC_{last}$) were 0.25 and 0.17 for Compound 10 and BMS-777607, respectively.

Table 5 summarizes the results of this experiment.

TABLE 5

Summary of PK parameters

| Drug | Dose | Matrix | $C_0$ (ng/mL) | $AUC_{last}$ (ng · h/mL) | $AUC_{inf}$ (h*ng · h/mL) | $V_{SS}$ (L/Kg) | CL (mL/min/kg) | $T_{1/2}$ (h) |
|---|---|---|---|---|---|---|---|---|
| Compound 10 | 2 mg/kg | Plasma | 16000 | 9830 | 9910 | 0.179 | 3.36 | 0.987 |
| Compound 10 | 2 mg/kg | Bone with Bone marrow | 1260 | 2420 | 2920 | 1.50 | 11.4 | 1.61 |
| Compound 12 | 2 mg/kg | Plasma | 4680 | 959 | 963 | 0.879 | 34.6 | 1.17 |
| Compound 12 | 2 mg/kg | Bone only | ND | ND | ND | NA | NA | NR |
| Compound 12 | 2 mg/kg | Bone marrow | ND | ND | ND | NA | NA | NR |
| BMS-777607 | 2 mg/kg | Plasma | 3610 | 1690 | 1690 | 1.42 | 19.7 | 3.42 |
| BMS-777607 | 2 mg/kg | Bone only | 26.5 | 296 | NR | NA | NA | NR |
| BMS-777607 | 2 mg/kg | Bone marrow | ND | ND | ND | NA | NA | NR |

NR: Not reportable due to inadequate elimination phase
ND: Not detected
NA: Not applicable It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions: while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage: thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition or negative modulation of Ron tyrosine kinase protein activity an appropriate dosage level will generally be about 0.01 to 500 mg per kg patient body weight per day and can be administered in single or multiple doses. Preferably, the dosage level will be about 0.1 to about 250 mg/kg per day: more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting or negatively modulating Ron tyrosine kinase activity (e.g., treatment of a disorder of uncontrolled cellular proliferation, cancer, breast cancer, metastatic breast cancer, etc) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above-mentioned pathological conditions.

It is understood that the disclosed compositions can be prepared from the disclosed compounds. It is also understood that the disclosed compositions can be employed in the disclosed methods of using.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of the invention or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above-mentioned pathological conditions.

1. Treatment Methods

The compounds disclosed herein are useful for treating, preventing, ameliorating, controlling or reducing the risk of a variety of disorders wherein the patient or subject would benefit from inhibition or negative modulation of a Ron tyrosine kinase. In one aspect, provided is a method of treating or preventing a disorder in a subject comprising the step of administering to the subject at least one disclosed compound: at least one disclosed pharmaceutical composition; and/or at least one disclosed product in a dosage and amount effective to treat the disorder in the subject.

Also provided is a method for the treatment of one or more disorders, for which Ron tyrosine kinase inhibition is predicted to be beneficial, in a subject comprising the step of administering to the subject at least one disclosed compound: at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound: at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

In one aspect, the disorder is a cancer.

It is understood that cancer refer to or describe the physiological condition in mammals that is typically characterized by unregulated cell growth. The cancer may be multi-drug resistant (MDR) or drug-sensitive. Examples of cancer include but are not limited to, osteolytic cancer, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer: bone cancer: brain and CNS cancer: choriocarcinoma: connective tissue cancer: esophageal cancer: eye cancer: cancer of the head and neck: gastric cancer; intra-epithelial neoplasm; larynx cancer: lymphoma including Hodgkin's and Non-Hodgkin's lymphoma: melanoma: myeloma: neuroblastoma: oral cavity cancer (e.g., lip, tongue, mouth, and pharynx): retinoblastoma: rhabdomyosarcoma: rectal cancer: cancer of the respiratory system: sarcoma: skin cancer: stomach cancer: testicular cancer; uterine cancer: cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma. B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In one embodiment, cancer can be a metastatic cancer, including but not limited to metastatic breast cancer, for example, bone metastasis (i.e., osteolytic metastasis). In yet another embodiment, the disorder is a bone disorder.

In one embodiment, the bone disorder comprises bone loss, osteoporosis and osteoarthritis.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The compounds are further useful in a method for the prevention, treatment, control, amelioration, or reeducation of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a Ron tyrosine kinase inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

In the treatment of conditions which require inhibition or negative modulation of Ron tyrosine kinase, an appropriate dosage level will generally be about 0.01 to 1000 mg per kg patient body weight per day which can be administered in single or multiple doses. Preferably, the dosage level will be about 0.1 to about 250 mg/kg per day: more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating Ron tyrosine kinase in at least one cell, comprising the step of contacting the at least one cell with at least one compound of the invention, in an amount effective to modulate or activate Ron tyrosine kinase activity response in the at least one cell. In a further aspect, the cell is mammalian, for example human. In a further aspect, the cell has been isolated from a subject prior to the contacting step. In a further aspect, contacting is via administration to a subject.

In one aspect, the invention relates to a method for the treatment of a disorder of uncontrolled cellular proliferation in a mammal, the method comprising the step of administering to the mammal an effective amount of least one disclosed compound or a product of a disclosed method of making a compound, or a pharmaceutically acceptable salt, isomer, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is associated with a Ron tyrosine kinase activity.

2. Manufacture of a Medicament

In one aspect, the invention relates to a method for the manufacture of a medicament for inhibition of Ron tyrosine kinase activity in a mammal comprising combining a therapeutically effective amount of a disclosed compound or product of a disclosed method with a pharmaceutically acceptable carrier or diluent.

F. Experimental

Prophetic Pharmaceutical Composition Examples

"Active ingredient" as used throughout examples relates to one or more of the compounds of the invention, or a pharmaceutically acceptable salt, isomer, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) weight indicated below | Amount necessary to yield total |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format:

diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volumen indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A phosphonate conjugate with compound A, wherein compound A has the following structural formula:

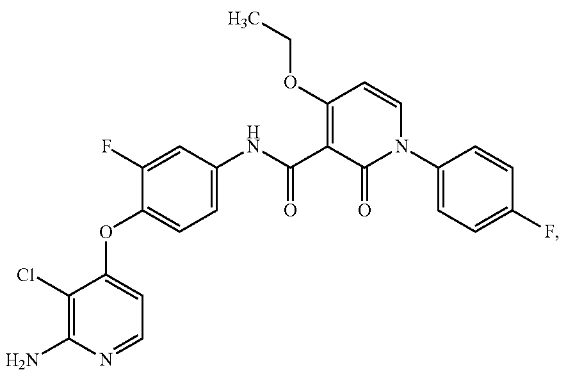 [SMILES: CCOc1ccn(-c2ccc(F)cc2)c(=O)c1C(=O)Nc1ccc(Oc2ccnc(N)c2Cl)c(F)c1]

and wherein the phosphonate is directly conjugated to compound A, and wherein said conjugate is selected from the group consisting of

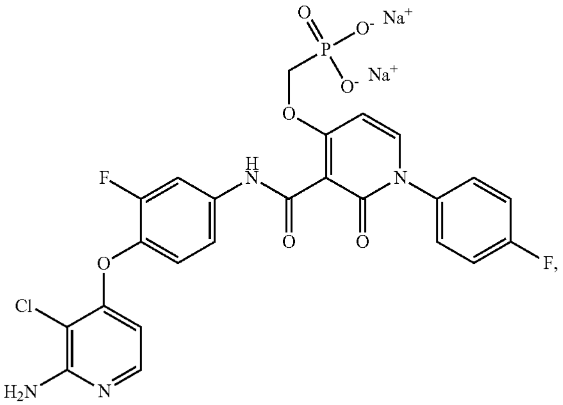

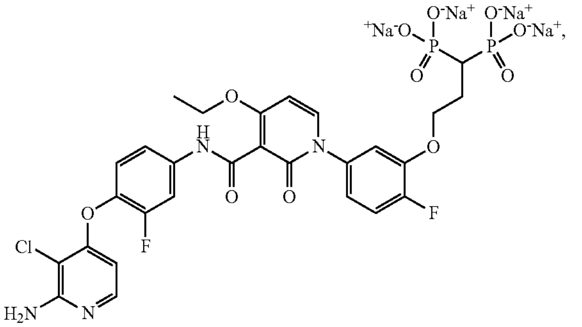

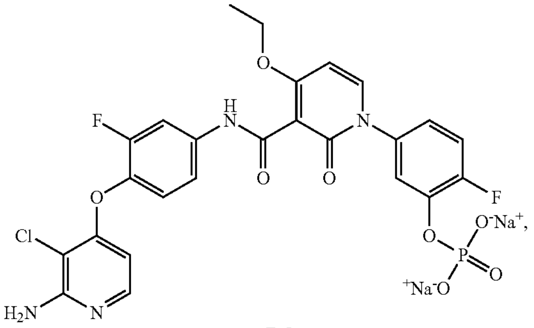

and

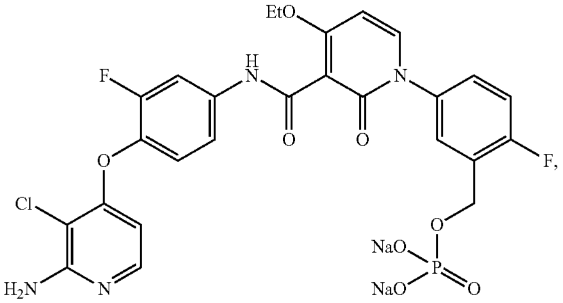

and a pharmaceutically acceptable salt or isomer thereof.

2. The compound of claim 1, wherein said compound is:

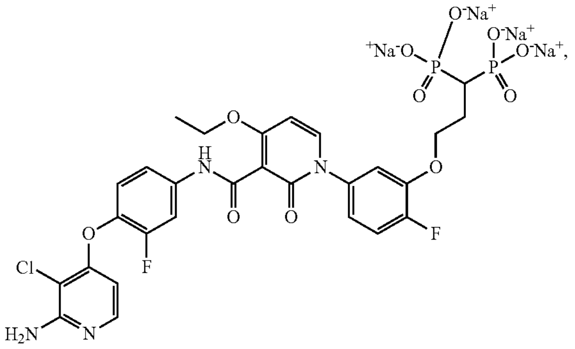

or a pharmaceutically acceptable salt, or isomer thereof.

3. A pharmaceutical composition comprising a therapeutically effective amount of a compound of claim 1 and a pharmaceutically acceptable carrier.

4. A method for the treatment of a disorder of uncontrolled cellular proliferation in a mammal, the method comprising the step of administering to the mammal an effective amount of a compound of claim 1.

5. The method of claim 4, wherein said disorder is associated with a Ron tyrosine kinase activity.

6. The method of claim 5, wherein said disorder is cancer.

7. The method of claim 6, wherein said cancer is breast cancer.

8. The method of claim 7, wherein said breast cancer is metastatic breast cancer.

9. The method of claim 8, wherein said metastatic breast cancer is bone metastatic breast cancer.

10. A method for the treatment of a bone loss disorder in a mammal, the method comprising the step of administering to the mammal an effective amount of a compound of claim 1.

11. The method of claim 10, wherein said bone loss disorder is osteoporosis.

12. The method of claim 10, wherein said bone loss disorder is osteoarthritis.

* * * * *